US011033491B2

(12) United States Patent
Tamarkin et al.

(10) Patent No.: US 11,033,491 B2
(45) Date of Patent: Jun. 15, 2021

(54) DICARBOXYLIC ACID FOAMABLE VEHICLE AND PHARMACEUTICAL COMPOSITIONS THEREOF

(71) Applicant: Foamix Pharmaceuticals Ltd., Rehovot (IL)

(72) Inventors: Dov Tamarkin, Maccabim (IL); Doron Friedman, Karmei Yosef (IL); Tal Berman, Rishon Le Ziyyon (IL); Enbal Ziv, Gedera (IL); David Schuz, Gimzu (IL)

(73) Assignee: Vyne Therapeutics Inc., Bridgewater, NJ (US)

( * ) Notice: Subject to any disclaimer, the term of this patent is extended or adjusted under 35 U.S.C. 154(b) by 0 days.

(21) Appl. No.: 17/072,243

(22) Filed: Oct. 16, 2020

(65) Prior Publication Data
US 2021/0038517 A1 Feb. 11, 2021

Related U.S. Application Data

(60) Division of application No. 15/903,275, filed on Feb. 23, 2018, now Pat. No. 10,821,077, which is a
(Continued)

(51) Int. Cl.
| | | |
|---|---|---|
| *A61K 9/00* | (2006.01) | |
| *A01N 25/16* | (2006.01) | |
| *A61K 8/34* | (2006.01) | |
| *A61K 8/42* | (2006.01) | |
| *A61K 8/92* | (2006.01) | |
| *A61K 8/73* | (2006.01) | |
| *A61Q 17/02* | (2006.01) | |
| *A61K 8/81* | (2006.01) | |
| *A61K 8/87* | (2006.01) | |
| *A61Q 19/00* | (2006.01) | |
| *A61K 8/362* | (2006.01) | |
| *A61K 8/37* | (2006.01) | |
| *A61K 8/49* | (2006.01) | |
| *A61K 8/86* | (2006.01) | |
| *A61K 8/04* | (2006.01) | |
| *A61K 9/12* | (2006.01) | |
| *A61Q 17/04* | (2006.01) | |

(Continued)

(52) U.S. Cl.
CPC ............ *A61K 9/0014* (2013.01); *A01N 25/16* (2013.01); *A61K 8/046* (2013.01); *A61K 8/34* (2013.01); *A61K 8/345* (2013.01); *A61K 8/362* (2013.01); *A61K 8/37* (2013.01); *A61K 8/42* (2013.01); *A61K 8/4993* (2013.01); *A61K 8/731* (2013.01); *A61K 8/736* (2013.01); *A61K 8/8152* (2013.01); *A61K 8/8158* (2013.01); *A61K 8/86* (2013.01); *A61K 8/87* (2013.01); *A61K 8/922* (2013.01); *A61K 9/122* (2013.01); *A61Q 17/02* (2013.01); *A61Q 17/04* (2013.01); *A61Q 19/00* (2013.01); *A61Q 19/007* (2013.01); *A61Q 19/02* (2013.01); *A61Q 19/08* (2013.01); *A61K 2800/24* (2013.01); *A61K 2800/242* (2013.01); *A61K 2800/244* (2013.01); *A61K 2800/30* (2013.01)

(58) Field of Classification Search
CPC ........ A61K 9/0014; A61K 8/362; A61K 8/37; A61K 8/4993; A61K 8/86; A61K 8/34; A61K 8/345; A61K 8/42; A61K 8/922; A61K 8/731; A61K 8/736; A61K 8/8152; A61K 8/8158; A61K 8/87; A61K 8/046; A61K 9/122; A61K 2800/24; A61K 2800/242; A61K 2800/244; A61K 2800/30; A01N 25/16; A61Q 19/007; A61Q 17/02; A61Q 17/04; A61Q 19/00; A61Q 19/02; A61Q 19/08; A61P 9/00; A61P 23/00; A61P 29/00; A61P 31/00; A61P 37/08

See application file for complete search history.

(56) References Cited

U.S. PATENT DOCUMENTS

| | | | |
|---|---|---|---|
| 1,159,250 | A | 11/1915 | Moulton |
| 1,666,684 | A | 4/1928 | Carstens |

(Continued)

FOREIGN PATENT DOCUMENTS

| | | | |
|---|---|---|---|
| AU | 198780257 | A | 9/1986 |
| AU | 782515 | B2 | 12/2005 |

(Continued)

OTHER PUBLICATIONS

"Everything but the Olive." The Olive Oil Source 1998-2016 [online]. Retrieved from the Internet: http://www.oliveoilsource.com/pageA chemical-characteristics.

(Continued)

*Primary Examiner* — Robert S Cabral
(74) *Attorney, Agent, or Firm* — Finnegan, Henderson, Farabow, Garrett & Dunner, LLP

(57) ABSTRACT

The present invention teaches a foamable pharmaceutical carrier comprising a benefit agent, selected from the group consisting of a dicarboxylic acid and a dicarboxylic acid ester; a stabilizer selected from the group consisting of at least one surface-active agent; at least one polymeric agent and mixtures thereof; a solvent selected from the group consisting of water, a hydrophilic solvent, a hydrophobic solvent, a potent solvent, a polar solvent, a silicone, an emollient, and mixtures thereof, wherein the benefit agent, stabilizer and solvent are selected to provide a composition that is substantially resistant to aging and to phase separation and or can substantially stabilize other active ingredients. The invention further relates to a foamable composition further containing a liquefied hydrocarbon gas propellant.

6 Claims, No Drawings

Related U.S. Application Data continuation of application No. 13/796,860, filed on Mar. 12, 2013, now abandoned, which is a continuation of application No. 11/825,406, filed on Jul. 5, 2007, now Pat. No. 9,265,725, which is a continuation-in-part of application No. 11/717,897, filed on Mar. 13, 2007, now Pat. No. 8,119,109, which is a continuation-in-part of application No. 11/078,902, filed on Mar. 11, 2005, now Pat. No. 9,668,972.

(60) Provisional application No. 60/818,634, filed on Jul. 5, 2006.

(51) Int. Cl.
*A61Q 19/02* (2006.01)
*A61Q 19/08* (2006.01)

(56) References Cited

U.S. PATENT DOCUMENTS

| | | |
|---|---|---|
| 1,924,972 A | 8/1933 | Beckert |
| 2,085,733 A | 7/1937 | Bird |
| 2,390,921 A | 12/1945 | Clark |
| 2,524,590 A | 10/1950 | Boe |
| 2,586,287 A | 2/1952 | Apperson |
| 2,617,754 A | 11/1952 | Neely |
| 2,767,712 A | 10/1956 | Waterman |
| 2,968,628 A | 1/1961 | Reed |
| 3,004,894 A | 10/1961 | Johnson et al. |
| 3,062,715 A | 11/1962 | Reese et al. |
| 3,067,784 A | 12/1962 | Gorman |
| 3,092,255 A | 6/1963 | Hohman |
| 3,092,555 A | 6/1963 | Horn |
| 3,141,821 A | 7/1964 | Compeau |
| 3,142,420 A | 7/1964 | Gawthrop |
| 3,144,386 A | 8/1964 | Brightenback |
| 3,149,543 A | 9/1964 | Naab |
| 3,154,075 A | 10/1964 | Weckesser |
| 3,178,352 A | 4/1965 | Erickson |
| 3,236,457 A | 2/1966 | Kennedy et al. |
| 3,244,589 A | 4/1966 | Sunnen |
| 3,252,859 A | 5/1966 | Silver |
| 3,261,695 A | 7/1966 | Sienkiewicz |
| 3,263,867 A | 8/1966 | Lehmann |
| 3,263,869 A | 8/1966 | Corsette |
| 3,298,919 A | 1/1967 | Bishop et al. |
| 3,301,444 A | 1/1967 | Wittke |
| 3,303,970 A | 2/1967 | Breslau et al. |
| 3,330,730 A | 7/1967 | Hernandez |
| 3,333,333 A | 8/1967 | Noack |
| 3,334,147 A | 8/1967 | Brunelle et al. |
| 3,342,845 A | 9/1967 | Sayigh et al. |
| 3,346,451 A | 10/1967 | Collins et al. |
| 3,366,494 A | 1/1968 | Bower et al. |
| 3,369,034 A | 2/1968 | Chalmers |
| 3,377,004 A | 4/1968 | Wittke |
| 3,383,280 A | 5/1968 | Kuehns |
| 3,384,541 A | 5/1968 | Clark et al. |
| 3,395,214 A | 7/1968 | Mummert |
| 3,395,215 A | 7/1968 | Schubert |
| 3,401,849 A | 9/1968 | Weber, III |
| 3,419,658 A | 12/1968 | Sanders |
| 3,456,052 A | 7/1969 | Gordon |
| 3,527,559 A | 9/1970 | Sliwinski |
| 3,540,448 A | 11/1970 | Sunnen |
| 3,559,890 A | 2/1971 | Brooks et al. |
| 3,561,262 A | 2/1971 | Borucki |
| 3,563,098 A | 2/1971 | Weber, III |
| 3,574,821 A | 4/1971 | Pfirrmann |
| 3,577,518 A | 5/1971 | Shepherd |
| 3,667,461 A | 6/1972 | Zamarra |
| 3,751,562 A | 8/1973 | Nichols |
| 3,770,648 A | 11/1973 | Mackles |
| 3,787,566 A | 1/1974 | Gauvreau |
| 3,819,524 A | 6/1974 | Schubert et al. |
| 3,824,303 A | 7/1974 | Lanzet et al. |
| 3,841,525 A | 10/1974 | Siegel |
| 3,849,569 A | 11/1974 | Mead |
| 3,849,580 A | 11/1974 | Weinstein et al. |
| 3,865,275 A | 2/1975 | De Nunzio |
| 3,866,800 A | 2/1975 | Schmitt |
| 3,878,118 A | 4/1975 | Watson |
| 3,882,228 A | 5/1975 | Boncey et al. |
| 3,886,084 A | 5/1975 | Vassiliades |
| 3,890,305 A | 6/1975 | Weber et al. |
| 3,912,665 A | 10/1975 | Spitzer et al. |
| 3,912,667 A | 10/1975 | Spitzer et al. |
| 3,923,970 A | 12/1975 | Breuer |
| 3,929,985 A | 12/1975 | Webb, Jr. |
| 3,952,916 A | 4/1976 | Phillips |
| 3,953,591 A | 4/1976 | Snyder |
| 3,959,160 A | 5/1976 | Horsler et al. |
| 3,962,150 A | 6/1976 | Viola |
| 3,963,833 A | 6/1976 | DeSalva et al. |
| 3,966,090 A | 6/1976 | Prussin et al. |
| 3,966,632 A | 6/1976 | Colliopoulos et al. |
| 3,970,219 A | 7/1976 | Spitzer et al. |
| 3,970,584 A | 7/1976 | Hart et al. |
| 3,993,224 A | 11/1976 | Harrison |
| 3,997,467 A | 12/1976 | Jederstrom |
| 4,001,391 A | 1/1977 | Feinstone et al. |
| 4,001,442 A | 1/1977 | Stahlberger et al. |
| 4,018,396 A | 4/1977 | Showmaker et al. |
| 4,019,657 A | 4/1977 | Spitzer et al. |
| 4,052,513 A | 10/1977 | Kaplan |
| 4,083,974 A | 4/1978 | Turi |
| 4,102,995 A | 7/1978 | Hebborn |
| 4,110,426 A | 8/1978 | Barnhurst et al. |
| 4,124,149 A | 11/1978 | Spitzer et al. |
| 4,145,411 A | 3/1979 | Mende |
| 4,151,272 A | 4/1979 | Geary et al. |
| 4,160,827 A | 7/1979 | Cho et al. |
| 4,178,373 A | 12/1979 | Klein et al. |
| 4,213,979 A | 7/1980 | Levine |
| 4,214,000 A | 7/1980 | Papa |
| 4,226,344 A | 10/1980 | Booth et al. |
| 4,229,432 A | 10/1980 | Geria |
| 4,230,701 A | 10/1980 | Holick et al. |
| 4,241,048 A | 12/1980 | Durbak et al. |
| 4,241,149 A | 12/1980 | Labes et al. |
| 4,252,787 A | 2/1981 | Sherman et al. |
| 4,254,104 A | 3/1981 | Suzuki et al. |
| 4,268,499 A | 5/1981 | Keil |
| 4,271,149 A | 6/1981 | Winicov et al. |
| 4,278,206 A | 7/1981 | Prussin |
| 4,292,250 A | 9/1981 | DeLuca et al. |
| 4,292,326 A | 9/1981 | Nazzaro-Porro et al. |
| 4,299,826 A | 11/1981 | Luedders |
| 4,305,936 A | 12/1981 | Klein |
| 4,309,995 A | 1/1982 | Sacco |
| 4,310,510 A | 1/1982 | Sherman et al. |
| 4,323,582 A | 4/1982 | Siegel et al. |
| 4,323,694 A | 4/1982 | Scala, Jr. |
| 4,325,939 A | 4/1982 | Shah |
| 4,329,990 A | 5/1982 | Sneider |
| 4,335,120 A | 6/1982 | Holick et al. |
| 4,338,211 A | 7/1982 | Stiros |
| 4,352,808 A | 10/1982 | Rane et al. |
| 4,363,806 A | 12/1982 | Bergström et al. |
| 4,385,161 A | 5/1983 | Caunt et al. |
| 4,386,104 A | 5/1983 | Nazzaro-Porro |
| 4,393,066 A | 7/1983 | Garrett et al. |
| 4,427,670 A | 1/1984 | Ofuchi et al. |
| 4,439,416 A | 3/1984 | Cordon et al. |
| 4,439,441 A | 3/1984 | Hallesy et al. |
| 4,440,320 A | 4/1984 | Wernicke |
| 4,447,486 A | 5/1984 | Hoppe et al. |
| 4,469,674 A | 9/1984 | Shah et al. |
| 4,508,705 A | 4/1985 | Chaudhuri et al. |
| 4,522,948 A | 6/1985 | Walker |
| 4,529,601 A | 7/1985 | Broberg et al. |
| 4,529,605 A | 7/1985 | Lynch et al. |
| 4,552,872 A | 11/1985 | Cooper et al. |
| 4,574,052 A | 3/1986 | Gupte et al. |

(56) References Cited

U.S. PATENT DOCUMENTS

| | | |
|---|---|---|
| 4,576,961 A | 3/1986 | Lorck et al. |
| 4,595,526 A | 6/1986 | Lai |
| 4,603,812 A | 8/1986 | Stoesser et al. |
| 4,607,101 A | 8/1986 | Bernstein |
| 4,612,193 A | 9/1986 | Gordon et al. |
| 4,627,973 A | 12/1986 | Moran et al. |
| 4,628,063 A | 12/1986 | Haines et al. |
| 4,661,340 A | 4/1987 | Nagy née Kricsfalussy et al. |
| 4,661,524 A | 4/1987 | Thomson et al. |
| 4,672,078 A | 6/1987 | Sakai et al. |
| 4,673,569 A | 6/1987 | Shernov et al. |
| 4,678,463 A | 7/1987 | Millar |
| 4,701,320 A | 10/1987 | Hasegawa et al. |
| 4,725,609 A | 2/1988 | Kull, Jr. et al. |
| 4,738,396 A | 4/1988 | Doi et al. |
| 4,741,855 A | 5/1988 | Grote et al. |
| 4,752,465 A | 6/1988 | Mackles |
| 4,770,634 A | 9/1988 | Pellico |
| 4,772,427 A | 9/1988 | Dawson |
| 4,780,309 A | 10/1988 | Geria et al. |
| 4,784,842 A | 11/1988 | London et al. |
| 4,792,062 A | 12/1988 | Goncalves |
| 4,798,682 A | 1/1989 | Ansmann |
| 4,804,674 A | 2/1989 | Curtis-Prior et al. |
| 4,806,262 A | 2/1989 | Snyder |
| 4,808,388 A | 2/1989 | Beutler et al. |
| 4,822,613 A | 4/1989 | Rodero |
| 4,822,614 A | 4/1989 | Rodero |
| 4,826,048 A | 5/1989 | Skorka et al. |
| 4,827,378 A | 5/1989 | Gillan et al. |
| 4,828,837 A | 5/1989 | Uster et al. |
| 4,836,217 A | 6/1989 | Fischer et al. |
| 4,837,019 A | 6/1989 | Georgalas et al. |
| 4,837,378 A | 6/1989 | Borgman |
| 4,844,902 A | 7/1989 | Grohe |
| 4,847,068 A | 7/1989 | Dole et al. |
| 4,849,117 A | 7/1989 | Bronner et al. |
| 4,849,211 A | 7/1989 | Schrauzer |
| 4,851,154 A | 7/1989 | Grollier et al. |
| 4,855,294 A | 8/1989 | Patel et al. |
| 4,863,900 A | 9/1989 | Pollock et al. |
| 4,867,967 A | 9/1989 | Crutcher |
| 4,873,078 A | 10/1989 | Edmundson et al. |
| 4,874,794 A | 10/1989 | Katz |
| 4,876,083 A | 10/1989 | Grollier et al. |
| 4,877,805 A | 10/1989 | Kligman |
| 4,885,282 A | 12/1989 | Thornfeldt |
| 4,897,262 A | 1/1990 | Nandagiri et al. |
| 4,902,281 A | 2/1990 | Avoy |
| 4,906,453 A | 3/1990 | Tsoucalas |
| 4,913,893 A | 4/1990 | Varco et al. |
| 4,919,934 A | 4/1990 | Deckner et al. |
| 4,933,330 A | 6/1990 | Jorgensen et al. |
| 4,950,420 A | 8/1990 | Svarz |
| 4,954,487 A | 9/1990 | Cooper et al. |
| 4,956,049 A | 9/1990 | Bernheim et al. |
| 4,957,732 A | 9/1990 | Grollier et al. |
| 4,963,351 A | 10/1990 | Weston |
| 4,965,063 A | 10/1990 | Casey et al. |
| 4,966,779 A | 10/1990 | Kirk |
| 4,970,067 A | 11/1990 | Panandiker et al. |
| 4,975,466 A | 12/1990 | Bottcher et al. |
| 4,981,367 A | 1/1991 | Brazelton |
| 4,981,677 A | 1/1991 | Thau |
| 4,981,679 A | 1/1991 | Briggs et al. |
| 4,981,845 A | 1/1991 | Pereira et al. |
| 4,985,459 A | 1/1991 | Sunshine et al. |
| 4,992,478 A | 2/1991 | Geria |
| 4,993,496 A | 2/1991 | Riedle et al. |
| 4,996,193 A | 2/1991 | Hewitt et al. |
| 5,002,540 A | 3/1991 | Brodman et al. |
| 5,002,680 A | 3/1991 | Schmidt et al. |
| 5,007,556 A | 4/1991 | Lover |
| 5,013,297 A | 5/1991 | Cattanach |
| 5,015,471 A | 5/1991 | Birtwistle et al. |
| 5,019,375 A | 5/1991 | Tanner et al. |
| 5,034,220 A | 7/1991 | Helioff et al. |
| 5,035,895 A | 7/1991 | Shibusawa et al. |
| 5,053,228 A | 10/1991 | Mori et al. |
| 5,071,648 A | 12/1991 | Rosenblatt |
| 5,071,881 A | 12/1991 | Parfondry et al. |
| 5,073,371 A | 12/1991 | Turner et al. |
| 5,082,651 A | 1/1992 | Healey et al. |
| 5,087,618 A | 2/1992 | Bodor |
| 5,089,252 A | 2/1992 | Grollier et al. |
| 5,091,111 A | 2/1992 | Neumiller |
| 5,094,853 A | 3/1992 | Hagarty |
| 5,100,917 A | 3/1992 | Flynn et al. |
| 5,104,645 A | 4/1992 | Cardin et al. |
| 5,112,359 A | 5/1992 | Murphy et al. |
| 5,114,718 A | 5/1992 | Damani |
| 5,122,519 A | 6/1992 | Ritter |
| 5,130,121 A | 7/1992 | Kopolow et al. |
| 5,133,972 A | 7/1992 | Ferrini et al. |
| 5,135,915 A | 8/1992 | Czarniecki et al. |
| 5,137,714 A | 8/1992 | Scott |
| 5,143,717 A | 9/1992 | Davis |
| 5,156,765 A | 10/1992 | Smrt |
| 5,160,665 A | 11/1992 | Owada et al. |
| 5,164,357 A | 11/1992 | Bartman et al. |
| 5,164,367 A | 11/1992 | Pickart |
| 5,167,950 A | 12/1992 | Lins |
| 5,171,577 A | 12/1992 | Griat et al. |
| 5,196,405 A | 3/1993 | Packman |
| 5,204,090 A | 4/1993 | Han |
| 5,204,093 A | 4/1993 | Victor |
| 5,208,031 A | 5/1993 | Kelly |
| 5,217,707 A | 6/1993 | Szabo et al. |
| 5,219,877 A | 6/1993 | Shah et al. |
| 5,221,530 A | 6/1993 | Janchitraponvej et al. |
| 5,221,534 A | 6/1993 | DesLauriers et al. |
| 5,221,696 A | 6/1993 | Ke et al. |
| 5,230,897 A | 7/1993 | Griffin et al. |
| 5,236,707 A | 8/1993 | Stewart, II |
| 5,252,246 A | 10/1993 | Ding et al. |
| 5,254,334 A | 10/1993 | Ramirez et al. |
| 5,262,407 A | 11/1993 | Leveque et al. |
| 5,266,592 A | 11/1993 | Grub et al. |
| 5,279,819 A | 1/1994 | Hayes |
| 5,286,475 A | 2/1994 | Louvet et al. |
| 5,294,365 A | 3/1994 | Welch et al. |
| 5,300,286 A | 4/1994 | Gee |
| 5,301,841 A | 4/1994 | Fuchs |
| 5,308,643 A | 5/1994 | Osipow et al. |
| 5,314,904 A | 5/1994 | Egidio et al. |
| 5,318,774 A | 6/1994 | Alban et al. |
| 5,322,683 A | 6/1994 | Mackles et al. |
| 5,326,557 A | 7/1994 | Glover et al. |
| 5,344,051 A | 9/1994 | Brown |
| 5,346,135 A | 9/1994 | Vincent |
| 5,352,437 A | 10/1994 | Nakagawa et al. |
| 5,369,131 A | 11/1994 | Poli et al. |
| 5,378,451 A | 1/1995 | Gorman et al. |
| 5,378,730 A | 1/1995 | Lee et al. |
| 5,380,761 A | 1/1995 | Szabo Anna Z. et al. |
| 5,384,308 A | 1/1995 | Henkin |
| 5,385,943 A | 1/1995 | Nazzaro-Porro |
| 5,389,305 A | 2/1995 | Repinec et al. |
| 5,389,676 A | 2/1995 | Michaels |
| 5,397,312 A | 3/1995 | Rademaker et al. |
| 5,398,846 A | 3/1995 | Corba et al. |
| 5,399,205 A | 3/1995 | Shinohara et al. |
| 5,411,992 A | 5/1995 | Eini et al. |
| 5,422,361 A | 6/1995 | Munayyer et al. |
| 5,429,815 A | 7/1995 | Faryniarz et al. |
| 5,435,996 A | 7/1995 | Glover et al. |
| 5,439,670 A | 8/1995 | Purewal et al. |
| 5,439,682 A | 8/1995 | Wivell et al. |
| 5,447,725 A | 9/1995 | Damani et al. |
| 5,449,520 A | 9/1995 | Frigerio et al. |
| 5,451,404 A | 9/1995 | Furman |
| 5,482,965 A | 1/1996 | Rajadhyaksha |
| 5,491,245 A | 2/1996 | Gruning et al. |
| 5,500,211 A | 3/1996 | George et al. |

(56) References Cited

U.S. PATENT DOCUMENTS

| | | |
|---|---|---|
| 5,508,033 A | 4/1996 | Briand et al. |
| 5,512,555 A | 4/1996 | Waldstreicher |
| 5,514,367 A | 5/1996 | Lentini et al. |
| 5,514,369 A | 5/1996 | Salka et al. |
| 5,520,918 A | 5/1996 | Smith |
| 5,523,078 A | 6/1996 | Baylin |
| 5,527,534 A | 6/1996 | Myhling |
| 5,527,822 A | 6/1996 | Scheiner |
| 5,529,770 A | 6/1996 | McKinzie et al. |
| 5,531,703 A | 7/1996 | Skwarek et al. |
| 5,534,261 A | 7/1996 | Rodgers et al. |
| 5,536,743 A | 7/1996 | Borgman |
| 5,540,853 A | 7/1996 | Trinh et al. |
| 5,545,401 A | 8/1996 | Shanbrom |
| 5,547,989 A | 8/1996 | Chamness |
| 5,558,872 A | 9/1996 | Jones et al. |
| 5,560,859 A | 10/1996 | Hartmann et al. |
| 5,567,420 A | 10/1996 | McEleney et al. |
| 5,576,016 A | 11/1996 | Amselem et al. |
| 5,578,315 A | 11/1996 | Chien et al. |
| 5,585,104 A | 12/1996 | Ha et al. |
| 5,589,157 A | 12/1996 | Hatfield |
| 5,589,515 A | 12/1996 | Suzuki et al. |
| 5,597,560 A | 1/1997 | Bergamini et al. |
| 5,603,940 A | 2/1997 | Candau et al. |
| 5,605,679 A | 2/1997 | Hansenne et al. |
| 5,608,119 A | 3/1997 | Amano et al. |
| 5,611,463 A | 3/1997 | Favre |
| 5,612,056 A | 3/1997 | Jenner et al. |
| 5,613,583 A | 3/1997 | Kono et al. |
| 5,613,623 A | 3/1997 | Hildebrandt |
| 5,614,171 A | 3/1997 | Clavenna et al. |
| 5,614,178 A | 3/1997 | Bloom et al. |
| 5,618,516 A | 4/1997 | Clavenna et al. |
| 5,635,469 A | 6/1997 | Fowler et al. |
| 5,641,480 A | 6/1997 | Vermeer |
| 5,643,600 A | 7/1997 | Mathur |
| 5,645,842 A | 7/1997 | Gruning et al. |
| 5,648,380 A | 7/1997 | Martin |
| 5,650,554 A | 7/1997 | Moloney |
| 5,658,575 A | 8/1997 | Ribier et al. |
| 5,658,749 A | 8/1997 | Thornton |
| 5,658,956 A | 8/1997 | Martin et al. |
| 5,663,208 A | 9/1997 | Martin |
| 5,672,634 A | 9/1997 | Tseng et al. |
| 5,679,324 A | 10/1997 | Lisboa et al. |
| 5,683,710 A | 11/1997 | Akemi et al. |
| 5,686,088 A | 11/1997 | Mitra et al. |
| 5,693,258 A | 12/1997 | Tonomura et al. |
| 5,695,551 A | 12/1997 | Buckingham et al. |
| 5,695,747 A | 12/1997 | Forestier et al. |
| 5,700,396 A | 12/1997 | Suzuki et al. |
| 5,705,472 A | 1/1998 | Hayes et al. |
| 5,716,611 A | 2/1998 | Oshlack et al. |
| 5,716,621 A | 2/1998 | Bello |
| 5,719,122 A | 2/1998 | Chiodini et al. |
| 5,719,197 A | 2/1998 | Kanios et al. |
| 5,725,872 A | 3/1998 | Stamm et al. |
| 5,725,874 A | 3/1998 | Oda |
| 5,730,964 A | 3/1998 | Waldstreicher |
| 5,733,558 A | 3/1998 | Breton et al. |
| 5,733,572 A | 3/1998 | Unger et al. |
| 5,741,509 A | 4/1998 | Kushner |
| 5,747,049 A | 5/1998 | Tominaga |
| 5,753,241 A | 5/1998 | Ribier et al. |
| 5,753,245 A | 5/1998 | Fowler et al. |
| 5,753,270 A | 5/1998 | Beauchamp et al. |
| 5,759,520 A | 6/1998 | Sachetto |
| 5,759,579 A | 6/1998 | Singh et al. |
| 5,767,104 A | 6/1998 | Bar-Shalom et al. |
| 5,773,410 A | 6/1998 | Yamamoto |
| 5,783,202 A | 7/1998 | Tomlinson et al. |
| 5,788,664 A | 8/1998 | Scalise |
| 5,792,448 A | 8/1998 | Dubief et al. |
| 5,792,922 A | 8/1998 | Moloney et al. |
| 5,797,955 A | 8/1998 | Walters |
| 5,804,546 A | 9/1998 | Hall et al. |
| 5,807,571 A | 9/1998 | List |
| 5,817,322 A | 10/1998 | Xu et al. |
| 5,824,650 A | 10/1998 | De Lacharriere et al. |
| 5,833,960 A | 11/1998 | Gers-Barlag et al. |
| 5,833,961 A | 11/1998 | Siegfried et al. |
| 5,837,270 A | 11/1998 | Burgess |
| 5,840,744 A | 11/1998 | Borgman |
| 5,840,771 A | 11/1998 | Oldham et al. |
| 5,843,411 A | 12/1998 | Hernandez et al. |
| 5,846,983 A | 12/1998 | Sandborn et al. |
| 5,849,042 A | 12/1998 | Lim et al. |
| 5,854,246 A | 12/1998 | Francois et al. |
| 5,856,452 A | 1/1999 | Moloney et al. |
| 5,858,371 A | 1/1999 | Singh et al. |
| 5,865,347 A | 2/1999 | Welschoff |
| 5,866,040 A | 2/1999 | Nakama et al. |
| 5,869,529 A | 2/1999 | Sintov et al. |
| 5,871,720 A | 2/1999 | Gutierrez et al. |
| 5,877,216 A | 3/1999 | Place et al. |
| 5,879,469 A | 3/1999 | Avram et al. |
| 5,881,493 A | 3/1999 | Restive |
| 5,885,581 A | 3/1999 | Massand |
| 5,889,028 A | 3/1999 | Sandborn et al. |
| 5,889,054 A | 3/1999 | Yu et al. |
| 5,891,458 A | 4/1999 | Britton et al. |
| 5,902,574 A | 5/1999 | Stoner et al. |
| 5,902,789 A | 5/1999 | Stoltz |
| 5,905,092 A | 5/1999 | Osborne et al. |
| 5,910,382 A | 6/1999 | Goodenough et al. |
| 5,911,981 A | 6/1999 | Dahms et al. |
| 5,912,007 A | 6/1999 | Pan et al. |
| 5,914,122 A | 6/1999 | Otterbeck et al. |
| 5,914,310 A | 6/1999 | Li et al. |
| 5,919,830 A | 7/1999 | Gopalkrishnan et al. |
| 5,922,331 A | 7/1999 | Mausner |
| 5,925,669 A | 7/1999 | Katz et al. |
| 5,939,376 A | 8/1999 | Durbut et al. |
| 5,948,682 A | 9/1999 | Moloney |
| 5,951,544 A | 9/1999 | Konwitz |
| 5,951,989 A | 9/1999 | Heymann |
| 5,951,993 A | 9/1999 | Scholz et al. |
| 5,952,373 A | 9/1999 | Lanzendorfer et al. |
| 5,952,392 A | 9/1999 | Katz et al. |
| 5,955,414 A | 9/1999 | Brown et al. |
| 5,959,161 A | 9/1999 | Kenmochi et al. |
| 5,961,957 A | 10/1999 | McAnalley |
| 5,961,998 A | 10/1999 | Arnaud et al. |
| 5,972,310 A | 10/1999 | Sachetto |
| 5,976,555 A | 11/1999 | Liu et al. |
| 5,980,904 A | 11/1999 | Leverett et al. |
| 5,990,100 A | 11/1999 | Rosenberg et al. |
| 5,993,846 A | 11/1999 | Friedman et al. |
| 6,001,341 A | 12/1999 | Genova et al. |
| 6,006,948 A | 12/1999 | Auer |
| 6,017,912 A | 1/2000 | Bussell |
| 6,019,967 A | 2/2000 | Breton et al. |
| 6,024,942 A | 2/2000 | Tanner et al. |
| 6,030,630 A | 2/2000 | Fleury et al. |
| 6,033,647 A | 3/2000 | Touzan et al. |
| 6,039,936 A | 3/2000 | Restle et al. |
| 6,042,848 A | 3/2000 | Lawyer et al. |
| 6,045,779 A | 4/2000 | Mueller et al. |
| 6,060,041 A | 5/2000 | Candau et al. |
| 6,071,536 A | 6/2000 | Suzuki et al. |
| 6,071,541 A | 6/2000 | Murad |
| 6,075,056 A | 6/2000 | Quigley, Jr. et al. |
| 6,080,394 A | 6/2000 | Lin et al. |
| 6,087,310 A | 7/2000 | Heinkel |
| 6,087,317 A | 7/2000 | Gee |
| 6,090,772 A | 7/2000 | Kaiser et al. |
| 6,093,408 A | 7/2000 | Hasenoehrl et al. |
| 6,096,756 A | 8/2000 | Crain et al. |
| 6,110,477 A | 8/2000 | Hernandez et al. |
| 6,110,966 A | 8/2000 | Pollock |
| 6,113,888 A | 9/2000 | Castro et al. |
| 6,116,466 A | 9/2000 | Gueret |
| 6,121,210 A | 9/2000 | Taylor |

(56) References Cited

U.S. PATENT DOCUMENTS

| | | |
|---|---|---|
| 6,126,920 A | 10/2000 | Jones et al. |
| 6,133,327 A | 10/2000 | Kimura et al. |
| 6,140,355 A | 10/2000 | Egidio et al. |
| 6,146,645 A | 11/2000 | Deckers et al. |
| 6,146,664 A | 11/2000 | Siddiqui |
| 6,162,834 A | 12/2000 | Sebillotte-Arnaud et al. |
| 6,165,455 A | 12/2000 | Torgerson et al. |
| 6,168,576 B1 | 1/2001 | Reynolds |
| 6,171,347 B1 | 1/2001 | Kunz et al. |
| 6,180,662 B1 | 1/2001 | Lanzendörfer et al. |
| 6,180,669 B1 | 1/2001 | Tamarkin |
| 6,183,762 B1 | 2/2001 | Deckers et al. |
| 6,186,367 B1 | 2/2001 | Harrold |
| 6,187,290 B1 | 2/2001 | Gilchrist et al. |
| 6,189,810 B1 | 2/2001 | Nerushai et al. |
| 6,190,365 B1 | 2/2001 | Abbott et al. |
| 6,204,285 B1 | 3/2001 | Fabiano et al. |
| 6,210,656 B1 | 4/2001 | Touzan et al. |
| 6,210,742 B1 | 4/2001 | Deckers et al. |
| 6,214,318 B1 | 4/2001 | Osipow et al. |
| 6,214,788 B1 | 4/2001 | Velazco et al. |
| 6,217,887 B1 | 4/2001 | Beerse et al. |
| 6,221,381 B1 | 4/2001 | Shelford et al. |
| 6,221,823 B1 | 4/2001 | Crisanti et al. |
| 6,224,888 B1 | 5/2001 | Vatter et al. |
| 6,231,837 B1 | 5/2001 | Stroud et al. |
| 6,232,315 B1 | 5/2001 | Shafer et al. |
| 6,241,971 B1 | 6/2001 | Fox et al. |
| 6,251,369 B1 | 6/2001 | Stoltz |
| 6,258,374 B1 | 7/2001 | Friess et al. |
| 6,261,544 B1 | 7/2001 | Coury et al. |
| 6,264,964 B1 | 7/2001 | Mohammadi |
| 6,270,781 B1 | 8/2001 | Gehlsen |
| 6,271,295 B1 | 8/2001 | Powell et al. |
| 6,274,150 B1 | 8/2001 | Simonnet et al. |
| 6,283,336 B1 | 9/2001 | Dwyer et al. |
| 6,284,802 B1 | 9/2001 | Bissett et al. |
| 6,287,546 B1 | 9/2001 | Reich et al. |
| 6,294,550 B1 | 9/2001 | Place et al. |
| 6,299,023 B1 | 10/2001 | Arnone |
| 6,299,032 B1 | 10/2001 | Hamilton |
| 6,299,900 B1 | 10/2001 | Reed et al. |
| 6,305,578 B1 | 10/2001 | Hildebrandt et al. |
| 6,306,841 B1 | 10/2001 | Place et al. |
| 6,308,863 B1 | 10/2001 | Harman |
| 6,319,913 B1 | 11/2001 | Mak et al. |
| 6,328,950 B1 | 12/2001 | Franzke et al. |
| 6,328,982 B1 | 12/2001 | Shiroyama et al. |
| 6,333,362 B1 | 12/2001 | Lorant |
| 6,335,022 B1 | 1/2002 | Simonnet et al. |
| 6,341,717 B2 | 1/2002 | Auer |
| 6,344,218 B1 | 2/2002 | Dodd et al. |
| 6,348,229 B1 | 2/2002 | Eini et al. |
| 6,352,727 B1 | 3/2002 | Takahashi |
| 6,355,230 B2 | 3/2002 | Gers-Barlag et al. |
| 6,358,541 B1 | 3/2002 | Goodman |
| 6,358,924 B1 | 3/2002 | Hoffmann |
| 6,364,854 B1 | 4/2002 | Ferrer et al. |
| 6,372,234 B1 | 4/2002 | Deckers et al. |
| 6,375,936 B1 | 4/2002 | Allard et al. |
| 6,375,960 B1 | 4/2002 | Simonnet et al. |
| 6,383,471 B1 | 5/2002 | Chen et al. |
| 6,395,258 B1 | 5/2002 | Steer |
| 6,395,300 B1 | 5/2002 | Straub et al. |
| 6,403,061 B1 | 6/2002 | Candau et al. |
| 6,403,069 B1 | 6/2002 | Chopra et al. |
| 6,410,036 B1 | 6/2002 | De Rosa et al. |
| 6,423,323 B2 | 7/2002 | Neubourg |
| 6,423,329 B1 | 7/2002 | Sine et al. |
| 6,428,772 B1 | 8/2002 | Singh et al. |
| 6,433,003 B1 | 8/2002 | Bobrove et al. |
| 6,433,024 B1 | 8/2002 | Popp et al. |
| 6,433,033 B1 | 8/2002 | Isobe et al. |
| 6,433,068 B1 | 8/2002 | Morrison et al. |
| 6,437,006 B1 | 8/2002 | Yoon et al. |
| 6,440,429 B1 | 8/2002 | Torizuka et al. |
| 6,447,801 B1 | 9/2002 | Salafsky et al. |
| 6,451,777 B1 | 9/2002 | Bradbury et al. |
| 6,455,076 B1 | 9/2002 | Hahn et al. |
| 6,468,989 B1 | 10/2002 | Chang et al. |
| 6,479,058 B1 | 11/2002 | McCadden |
| 6,479,060 B1 | 11/2002 | Jones et al. |
| 6,479,532 B1 | 11/2002 | Kamimura et al. |
| 6,482,810 B1 | 11/2002 | Brem et al. |
| 6,486,168 B1 | 11/2002 | Skwierczynski et al. |
| 6,488,947 B1 | 12/2002 | Bekele |
| 6,511,655 B1 | 1/2003 | Muller et al. |
| 6,514,487 B1 | 2/2003 | Barr |
| 6,524,594 B1 | 2/2003 | Santora et al. |
| 6,531,118 B1 | 3/2003 | Gonzalez et al. |
| 6,534,455 B1 | 3/2003 | Maurin et al. |
| 6,536,629 B2 | 3/2003 | van der Heijden |
| 6,544,530 B1 | 4/2003 | Friedman |
| 6,544,562 B2 | 4/2003 | Singh et al. |
| 6,547,063 B1 | 4/2003 | Zaveri et al. |
| 6,548,074 B1 | 4/2003 | Mohammadi |
| 6,551,604 B1 | 4/2003 | Beck et al. |
| 6,562,355 B1 | 5/2003 | Renault |
| 6,566,350 B2 | 5/2003 | Ono et al. |
| 6,582,679 B2 | 6/2003 | Stein et al. |
| 6,582,710 B2 | 6/2003 | Deckers et al. |
| 6,589,509 B2 | 7/2003 | Keller et al. |
| 6,596,287 B2 | 7/2003 | Deckers et al. |
| 6,599,513 B2 | 7/2003 | Deckers et al. |
| 6,607,716 B1 | 8/2003 | Smith et al. |
| 6,610,315 B2 | 8/2003 | Scholz et al. |
| 6,620,773 B1 | 9/2003 | Stork et al. |
| 6,638,981 B2 | 10/2003 | Williams et al. |
| 6,649,571 B1 | 11/2003 | Morgan |
| 6,649,574 B2 | 11/2003 | Cardis et al. |
| 6,672,483 B1 | 1/2004 | Roy |
| 6,682,726 B2 | 1/2004 | Marchesi et al. |
| 6,682,750 B2 | 1/2004 | Loeffler et al. |
| 6,691,898 B2 | 2/2004 | Hurray et al. |
| 6,706,290 B1 | 3/2004 | Kajander et al. |
| 6,709,663 B2 | 3/2004 | Espinoza |
| 6,723,309 B1 | 4/2004 | Deane |
| 6,730,288 B1 | 5/2004 | Abram |
| 6,736,860 B2 | 5/2004 | Patel et al. |
| 6,753,000 B2 | 6/2004 | Breton et al. |
| 6,753,013 B1 | 6/2004 | Didriksen et al. |
| 6,753,167 B2 | 6/2004 | Moloney et al. |
| 6,762,158 B2 | 7/2004 | Lukenbach et al. |
| 6,765,001 B2 | 7/2004 | Gans et al. |
| 6,774,114 B2 | 8/2004 | Castiel et al. |
| 6,777,591 B1 | 8/2004 | Chaudhary et al. |
| 6,790,435 B1 | 9/2004 | Ma et al. |
| 6,796,973 B1 | 9/2004 | Contente et al. |
| RE38,623 E | 10/2004 | Hernandez et al. |
| 6,811,767 B1 | 11/2004 | Bosch et al. |
| 6,834,778 B2 | 12/2004 | Jinbo et al. |
| 6,841,547 B2 | 1/2005 | Brown et al. |
| 6,843,390 B1 | 1/2005 | Bristor |
| 6,875,438 B2 | 4/2005 | Kraemer et al. |
| 6,881,271 B2 | 4/2005 | Ochiai |
| 6,890,567 B2 | 5/2005 | Nakatsu et al. |
| 6,897,195 B2 | 5/2005 | Su et al. |
| 6,902,737 B2 | 6/2005 | Quemin et al. |
| 6,911,211 B2 | 6/2005 | Eini et al. |
| 6,914,057 B1 | 7/2005 | Ryan et al. |
| 6,946,120 B2 | 9/2005 | Wai-Chiu So et al. |
| 6,946,139 B2 | 9/2005 | Henning |
| 6,951,654 B2 | 10/2005 | Malcolm et al. |
| 6,955,816 B2 | 10/2005 | Klysz |
| 6,956,062 B2 | 10/2005 | Beilfuss et al. |
| 6,958,154 B2 | 10/2005 | Andolino Brandt et al. |
| 6,967,023 B1 | 11/2005 | Eini et al. |
| 6,968,982 B1 | 11/2005 | Burns |
| 6,969,521 B1 | 11/2005 | Gonzalez et al. |
| RE38,964 E | 1/2006 | Shillington |
| 6,986,883 B2 | 1/2006 | Pellico |
| 6,994,863 B2 | 2/2006 | Eini et al. |
| 7,002,486 B2 | 2/2006 | Lawrence |
| 7,014,844 B2 | 3/2006 | Mahalingam et al. |

(56) References Cited

U.S. PATENT DOCUMENTS

| | | |
|---|---|---|
| 7,021,499 B2 | 4/2006 | Hansen et al. |
| 7,029,659 B2 | 4/2006 | Abram |
| 7,060,253 B1 | 6/2006 | Mundschenk |
| 7,078,058 B2 | 7/2006 | Jones et al. |
| 7,083,799 B1 | 8/2006 | Giacomoni |
| 7,137,536 B2 | 11/2006 | Walters et al. |
| 7,195,135 B1 | 3/2007 | Garcia |
| 7,222,802 B2 | 5/2007 | Sweeton |
| 7,225,518 B2 | 6/2007 | Eidenschink et al. |
| 7,226,230 B2 | 6/2007 | Liberatore |
| 7,235,251 B2 | 6/2007 | Hamer et al. |
| 7,252,816 B1 | 8/2007 | Angel et al. |
| 7,270,828 B2 | 9/2007 | Masuda et al. |
| 7,455,195 B2 | 11/2008 | Meketa |
| 7,497,354 B2 | 3/2009 | Decottignies et al. |
| 7,575,739 B2 | 8/2009 | Tamarkin et al. |
| 7,645,803 B2 | 1/2010 | Tamarkin et al. |
| 7,654,415 B2 | 2/2010 | van der Heijden |
| 7,682,623 B2 | 3/2010 | Eini et al. |
| 7,700,076 B2 | 4/2010 | Tamarkin et al. |
| 7,704,518 B2 | 4/2010 | Tamarkin et al. |
| 7,758,888 B2 | 7/2010 | Lapidot et al. |
| 7,793,807 B2 | 9/2010 | Goujon et al. |
| 7,820,145 B2 | 10/2010 | Tamarkin et al. |
| 7,842,791 B2 | 11/2010 | Britten et al. |
| 7,960,416 B2 | 6/2011 | Sato et al. |
| 8,114,385 B2 | 2/2012 | Tamarkin et al. |
| 8,119,106 B2 | 2/2012 | Tamarkin et al. |
| 8,119,109 B2 | 2/2012 | Tamarkin et al. |
| 8,119,150 B2 | 2/2012 | Tamarkin et al. |
| 8,158,109 B2 | 4/2012 | Abram et al. |
| 8,192,749 B2 | 6/2012 | Ashley |
| 8,211,874 B2 | 7/2012 | Theobald et al. |
| 8,343,945 B2 | 1/2013 | Tamarkin et al. |
| 8,362,091 B2 | 1/2013 | Tamarkin et al. |
| 8,435,498 B2 | 5/2013 | Tamarkin et al. |
| 8,486,374 B2 | 7/2013 | Tamarkin et al. |
| 8,486,375 B2 | 7/2013 | Tamarkin et al. |
| 8,486,376 B2 | 7/2013 | Friedman et al. |
| 8,512,718 B2 | 8/2013 | Eini et al. |
| 8,518,376 B2 | 8/2013 | Tamarkin et al. |
| 8,518,378 B2 | 8/2013 | Tamarkin et al. |
| 8,592,380 B2 | 11/2013 | Trumbore et al. |
| 8,617,100 B2 | 12/2013 | Eini et al. |
| 8,618,081 B2 | 12/2013 | Tamarkin et al. |
| 8,623,330 B2 | 1/2014 | Gurge et al. |
| 8,636,982 B2 | 1/2014 | Tamarkin et al. |
| 8,652,443 B2 | 2/2014 | Varanasi et al. |
| 8,703,105 B2 | 4/2014 | Tamarkin et al. |
| 8,709,385 B2 | 4/2014 | Tamarkin et al. |
| 8,722,021 B2 | 5/2014 | Friedman et al. |
| 8,735,377 B1 | 5/2014 | Sipos |
| 8,741,265 B2 | 6/2014 | Tamarkin et al. |
| 8,778,365 B1 | 7/2014 | Hardas et al. |
| 8,784,780 B2 | 7/2014 | Gurge et al. |
| 8,795,635 B2 | 8/2014 | Tamarkin et al. |
| 8,795,693 B2 | 8/2014 | Tamarkin et al. |
| 8,840,869 B2 | 9/2014 | Friedman et al. |
| 8,846,039 B2 | 9/2014 | Chung et al. |
| 8,859,618 B2 | 10/2014 | Palefsky et al. |
| 8,865,139 B1 | 10/2014 | Tamarkin et al. |
| 8,871,184 B2 | 10/2014 | Tamarkin et al. |
| 8,895,536 B2 | 11/2014 | Bannister et al. |
| 8,900,553 B2 | 12/2014 | Tamarkin et al. |
| 8,900,554 B2 | 12/2014 | Tamarkin et al. |
| 8,945,516 B2 | 2/2015 | Tamarkin et al. |
| 8,992,896 B2 | 3/2015 | Tamarkin et al. |
| 9,050,253 B2 | 6/2015 | Tamarkin et al. |
| 9,072,667 B2 | 7/2015 | Tamarkin et al. |
| 9,101,662 B2 | 8/2015 | Tamarkin et al. |
| 9,132,139 B2 | 9/2015 | Dhuin et al. |
| 9,161,916 B2 | 10/2015 | Tamarkin et al. |
| 9,167,813 B2 | 10/2015 | Tamarkin et al. |
| 9,192,558 B2 | 11/2015 | Chen et al. |
| 9,211,259 B2 | 12/2015 | Friedman et al. |
| 9,265,725 B2 | 2/2016 | Tamarkin et al. |
| 9,265,740 B2 | 2/2016 | Johnston et al. |
| 9,271,930 B2 | 3/2016 | At |
| 9,320,705 B2 | 4/2016 | Tamarkin et al. |
| 9,364,433 B2 | 6/2016 | Andersson et al. |
| 9,439,857 B2 | 9/2016 | Tamarkin et al. |
| 9,474,720 B2 | 10/2016 | Yamamoto |
| 9,492,412 B2 | 11/2016 | Tamarkin et al. |
| 9,539,208 B2 | 1/2017 | Tamarkin et al. |
| 9,539,266 B2 | 1/2017 | Mansouri |
| 9,549,898 B2 | 1/2017 | Tamarkin et al. |
| 9,572,775 B2 | 2/2017 | Tamarkin et al. |
| 9,592,246 B2 | 3/2017 | Salman et al. |
| 9,622,947 B2 | 4/2017 | Tamarkin et al. |
| 9,636,405 B2 | 5/2017 | Tamarkin et al. |
| 9,662,298 B2 | 5/2017 | Tamarkin et al. |
| 9,668,972 B2 | 6/2017 | Tamarkin et al. |
| 9,675,700 B2 | 6/2017 | Tamarkin et al. |
| 9,682,021 B2 | 6/2017 | Tamarkin et al. |
| 9,713,643 B2 | 7/2017 | Friedman et al. |
| 9,724,345 B2 | 8/2017 | Andersson et al. |
| 9,795,564 B2 | 10/2017 | Tamarkin et al. |
| 9,841,142 B2 | 12/2017 | Nair |
| 9,849,142 B2 | 12/2017 | Tamarkin et al. |
| 9,884,017 B2 | 2/2018 | Tamarkin et al. |
| 9,931,328 B2 | 4/2018 | Kandavilli et al. |
| 10,028,949 B2 | 7/2018 | Andersson et al. |
| 10,029,013 B2 | 7/2018 | Tamarkin et al. |
| 10,080,764 B2 | 9/2018 | Mansouri |
| 10,086,080 B2 | 10/2018 | Tamarkin et al. |
| 10,092,588 B2 | 10/2018 | Tamarkin et al. |
| 10,117,812 B2 | 11/2018 | Tamarkin et al. |
| 10,137,200 B2 | 11/2018 | Tamarkin et al. |
| 10,159,686 B2 | 12/2018 | Yamamoto |
| 10,213,384 B2 | 2/2019 | Tamarkin et al. |
| 10,213,443 B2 | 2/2019 | Salman et al. |
| 10,213,512 B2 | 2/2019 | Tamarkin et al. |
| 10,238,746 B2 | 3/2019 | Tamarkin et al. |
| 10,265,404 B2 | 4/2019 | Tamarkin et al. |
| 10,278,917 B2 | 5/2019 | Shevachman et al. |
| 10,322,085 B2 | 6/2019 | Tamarkin et al. |
| 10,322,186 B2 | 6/2019 | Tamarkin et al. |
| 10,350,166 B2 | 7/2019 | Tamarkin et al. |
| 10,350,226 B1 | 7/2019 | Atiba |
| 10,363,216 B2 | 7/2019 | Tamarkin et al. |
| 10,369,102 B2 | 8/2019 | Tamarkin et al. |
| 10,391,108 B2 | 8/2019 | Chen et al. |
| 10,398,641 B2 | 9/2019 | Tamarkin et al. |
| 10,434,046 B2 | 10/2019 | Latta et al. |
| 10,463,742 B2 | 11/2019 | Tamarkin et al. |
| 10,512,608 B2 | 12/2019 | Bommagani et al. |
| 10,517,882 B2 | 12/2019 | Tamarkin et al. |
| 10,543,298 B2 | 1/2020 | Sobral et al. |
| 10,548,890 B2 | 2/2020 | Andersson et al. |
| 10,588,858 B2 | 3/2020 | Tamarkin et al. |
| 10,653,707 B2 | 5/2020 | Mansouri |
| 10,780,046 B2 | 9/2020 | Shevachman et al. |
| 2001/0006654 A1 | 7/2001 | Cannell et al. |
| 2001/0027218 A1 | 10/2001 | Stern et al. |
| 2001/0027981 A1 | 10/2001 | Yquel |
| 2001/0033838 A1 | 10/2001 | Farmer |
| 2001/0036450 A1 | 11/2001 | Verite et al. |
| 2001/0054574 A1 | 12/2001 | Navarro |
| 2002/0004063 A1 | 1/2002 | Zhang |
| 2002/0013481 A1 | 1/2002 | Schonrock et al. |
| 2002/0015721 A1 | 2/2002 | Simonnet et al. |
| 2002/0031478 A1 | 3/2002 | Keller et al. |
| 2002/0032171 A1 | 3/2002 | Chen et al. |
| 2002/0035046 A1 | 3/2002 | Lukenbach et al. |
| 2002/0035070 A1 | 3/2002 | Gardlik et al. |
| 2002/0035087 A1 | 3/2002 | Barclay |
| 2002/0035182 A1 | 3/2002 | L'Alloret et al. |
| 2002/0039591 A1 | 4/2002 | Dahle |
| 2002/0044659 A1 | 4/2002 | Ohta |
| 2002/0045659 A1 | 4/2002 | Michelet et al. |
| 2002/0048798 A1 | 4/2002 | Avery et al. |
| 2002/0058010 A1 | 5/2002 | Picard-Lesboueyries et al. |
| 2002/0072544 A1 | 6/2002 | Miller et al. |
| 2002/0090386 A1 | 7/2002 | Halswanter et al. |

(56) References Cited

U.S. PATENT DOCUMENTS

| | | |
|---|---|---|
| 2002/0098215 A1 | 7/2002 | Douin et al. |
| 2002/0111281 A1 | 8/2002 | Vishnupad |
| 2002/0117516 A1 | 8/2002 | Lasserre et al. |
| 2002/0134376 A1 | 9/2002 | Castro et al. |
| 2002/0136755 A1 | 9/2002 | Tyrrell et al. |
| 2002/0143188 A1 | 10/2002 | Garvey et al. |
| 2002/0153390 A1 | 10/2002 | Vlodek |
| 2002/0165170 A1 | 11/2002 | Wilson et al. |
| 2002/0182162 A1 | 12/2002 | Shahinpoor et al. |
| 2002/0182234 A1 | 12/2002 | Riedel et al. |
| 2002/0187181 A1 | 12/2002 | Godbey et al. |
| 2002/0198136 A1 | 12/2002 | Mak et al. |
| 2003/0006193 A1 | 1/2003 | Ikeda et al. |
| 2003/0013692 A1 | 1/2003 | Gullans et al. |
| 2003/0017181 A1 | 1/2003 | Rood et al. |
| 2003/0031693 A1 | 2/2003 | Breton et al. |
| 2003/0053961 A1 | 3/2003 | Eccard |
| 2003/0077297 A1 | 4/2003 | Chen et al. |
| 2003/0077301 A1 | 4/2003 | Maibach et al. |
| 2003/0078172 A1 | 4/2003 | Guiramand et al. |
| 2003/0082120 A1 | 5/2003 | Milstein |
| 2003/0108502 A1 | 6/2003 | Uchida et al. |
| 2003/0114520 A1 | 6/2003 | Pereira et al. |
| 2003/0118515 A1 | 6/2003 | Jew et al. |
| 2003/0118527 A1 | 6/2003 | Jager et al. |
| 2003/0129259 A1 | 7/2003 | Mahalingam et al. |
| 2003/0130247 A1 | 7/2003 | Gans et al. |
| 2003/0148949 A1 | 8/2003 | Podolsky |
| 2003/0175232 A1 | 9/2003 | Elliott et al. |
| 2003/0175315 A1 | 9/2003 | Yoo et al. |
| 2003/0180347 A1 | 9/2003 | Young et al. |
| 2003/0185839 A1 | 10/2003 | Podolsky |
| 2003/0185861 A1 | 10/2003 | Hori et al. |
| 2003/0194379 A1 | 10/2003 | Brugger et al. |
| 2003/0195128 A1 | 10/2003 | Deckman et al. |
| 2003/0206955 A1 | 11/2003 | Sonneville-Aubrun et al. |
| 2003/0215418 A1 | 11/2003 | Asmus et al. |
| 2003/0215472 A1 | 11/2003 | Bonda et al. |
| 2003/0235597 A1 | 12/2003 | Withiam et al. |
| 2004/0002550 A1 | 1/2004 | Mecurio |
| 2004/0018228 A1 | 1/2004 | Fischell et al. |
| 2004/0028752 A1 | 2/2004 | Kamm et al. |
| 2004/0038912 A1 | 2/2004 | Michelet et al. |
| 2004/0053797 A1 | 3/2004 | Chen et al. |
| 2004/0058878 A1 | 3/2004 | Walker |
| 2004/0063787 A1 | 4/2004 | Villanueva |
| 2004/0067970 A1 | 4/2004 | Foster et al. |
| 2004/0072638 A1 | 4/2004 | Enos et al. |
| 2004/0076651 A1 | 4/2004 | Brocks et al. |
| 2004/0078896 A1 | 4/2004 | Hellyer et al. |
| 2004/0079361 A1 | 4/2004 | Clayton et al. |
| 2004/0105825 A1 | 6/2004 | Henning |
| 2004/0106688 A1 | 6/2004 | Koike et al. |
| 2004/0120917 A1 | 6/2004 | Perrier et al. |
| 2004/0127554 A1 | 7/2004 | Ghisalberti |
| 2004/0138179 A1 | 7/2004 | Goldstein et al. |
| 2004/0151671 A1 | 8/2004 | Abram et al. |
| 2004/0151756 A1 | 8/2004 | Richards et al. |
| 2004/0161447 A1 | 8/2004 | Paul |
| 2004/0184992 A1 | 9/2004 | Abram |
| 2004/0185123 A1 | 9/2004 | Mazzio et al. |
| 2004/0191196 A1 | 9/2004 | Tamarkin |
| 2004/0192754 A1 | 9/2004 | Shapira et al. |
| 2004/0195276 A1 | 10/2004 | Fuchs |
| 2004/0197276 A1 | 10/2004 | Takase et al. |
| 2004/0197295 A1 | 10/2004 | Riedel et al. |
| 2004/0198706 A1 | 10/2004 | Carrara |
| 2004/0219176 A1 | 11/2004 | Dominguez |
| 2004/0220187 A1 | 11/2004 | Stephenson et al. |
| 2004/0229813 A1 | 11/2004 | DiPiano et al. |
| 2004/0234475 A1 | 11/2004 | Lannibois-Drean et al. |
| 2004/0241099 A1 | 12/2004 | Popp et al. |
| 2004/0247531 A1 | 12/2004 | Riedel et al. |
| 2004/0258627 A1 | 12/2004 | Riedel et al. |
| 2004/0258628 A1 | 12/2004 | Riedel et al. |
| 2004/0258643 A1 | 12/2004 | Yaqub et al. |
| 2005/0002976 A1 | 1/2005 | Wu |
| 2005/0013853 A1 | 1/2005 | Gil-Ad et al. |
| 2005/0042182 A1 | 2/2005 | Arkin et al. |
| 2005/0054991 A1 | 3/2005 | Tobyn et al. |
| 2005/0069566 A1 | 3/2005 | Tamarkin et al. |
| 2005/0075407 A1 | 4/2005 | Tamarkin et al. |
| 2005/0079139 A1 | 4/2005 | Jacques et al. |
| 2005/0079228 A1 | 4/2005 | Jaiswal et al. |
| 2005/0084551 A1 | 4/2005 | Jensen et al. |
| 2005/0085843 A1 | 4/2005 | Opolski et al. |
| 2005/0100517 A1 | 5/2005 | Sanzgiri et al. |
| 2005/0101936 A1 | 5/2005 | Gonzales et al. |
| 2005/0106197 A1 | 5/2005 | Blin et al. |
| 2005/0123494 A1 | 6/2005 | Swaile et al. |
| 2005/0123496 A1 | 6/2005 | Shah et al. |
| 2005/0148552 A1 | 7/2005 | Ryan et al. |
| 2005/0153943 A1 | 7/2005 | Ashley |
| 2005/0164993 A1 | 7/2005 | Ashley |
| 2005/0186142 A1 | 8/2005 | Tamarkin et al. |
| 2005/0186147 A1 | 8/2005 | Tamarkin et al. |
| 2005/0189377 A1 | 9/2005 | Lanzendorfer et al. |
| 2005/0196414 A1 | 9/2005 | Dake et al. |
| 2005/0205086 A1 | 9/2005 | Tamarkin et al. |
| 2005/0207837 A1 | 9/2005 | Kosh et al. |
| 2005/0222090 A1 | 10/2005 | Cheng et al. |
| 2005/0232869 A1 | 10/2005 | Tamarkin et al. |
| 2005/0244354 A1 | 11/2005 | Speron |
| 2005/0245902 A1 | 11/2005 | Cornish et al. |
| 2005/0252995 A1 | 11/2005 | Westphal et al. |
| 2005/0255048 A1 | 11/2005 | Hirsh et al. |
| 2005/0258189 A1 | 11/2005 | Peterson et al. |
| 2005/0266035 A1 | 12/2005 | Healy et al. |
| 2005/0268416 A1 | 12/2005 | Sommers |
| 2005/0271596 A1 | 12/2005 | Friedman et al. |
| 2005/0276836 A1 | 12/2005 | Wilson et al. |
| 2005/0281749 A1 | 12/2005 | Willcox et al. |
| 2005/0281755 A1 | 12/2005 | Zarif et al. |
| 2005/0281766 A1 | 12/2005 | Martin et al. |
| 2005/0285912 A1 | 12/2005 | Delametter et al. |
| 2005/0287081 A1 | 12/2005 | Aust et al. |
| 2006/0008432 A1 | 1/2006 | Scarampi et al. |
| 2006/0018937 A1 | 1/2006 | Friedman et al. |
| 2006/0018938 A1 | 1/2006 | Neubourg |
| 2006/0029565 A1 | 2/2006 | Xu et al. |
| 2006/0051301 A1 | 3/2006 | Galopin et al. |
| 2006/0054634 A1 | 3/2006 | Meketa |
| 2006/0057168 A1 | 3/2006 | Larm et al. |
| 2006/0099151 A1 | 5/2006 | Neubourg |
| 2006/0108377 A1 | 5/2006 | Glynn et al. |
| 2006/0110415 A1 | 5/2006 | Gupta |
| 2006/0110418 A1 | 5/2006 | Johnson |
| 2006/0114745 A1 | 6/2006 | Ollmann et al. |
| 2006/0121073 A1 | 6/2006 | Goyal et al. |
| 2006/0140984 A1 | 6/2006 | Tamarkin et al. |
| 2006/0140990 A1 | 6/2006 | Bortz et al. |
| 2006/0160713 A1 | 7/2006 | Sekine et al. |
| 2006/0165616 A1 | 7/2006 | Brock et al. |
| 2006/0177392 A1 | 8/2006 | Walden |
| 2006/0193789 A1 | 8/2006 | Tamarkin et al. |
| 2006/0193813 A1 | 8/2006 | Simonnet |
| 2006/0204446 A1 | 9/2006 | Lulla et al. |
| 2006/0222675 A1 | 10/2006 | Sabnis et al. |
| 2006/0233721 A1 | 10/2006 | Tamarkin et al. |
| 2006/0239937 A2 | 10/2006 | Neubourg |
| 2006/0251684 A1 | 11/2006 | Annis et al. |
| 2006/0254597 A1 | 11/2006 | Thompson |
| 2006/0263323 A1 | 11/2006 | Hoang et al. |
| 2006/0269485 A1 | 11/2006 | Friedman et al. |
| 2006/0272199 A1 | 12/2006 | Licciardello et al. |
| 2006/0285912 A1 | 12/2006 | Eini et al. |
| 2006/0292080 A1 | 12/2006 | Abram et al. |
| 2007/0009607 A1 | 1/2007 | Jones |
| 2007/0010580 A1 | 1/2007 | De Paoli Ambrosi |
| 2007/0015739 A1 | 1/2007 | Walker et al. |
| 2007/0017696 A1 | 1/2007 | Lin et al. |
| 2007/0020304 A1 | 1/2007 | Tamarkin et al. |
| 2007/0027055 A1 | 2/2007 | Koivisto et al. |
| 2007/0036831 A1 | 2/2007 | Baker |

(56) References Cited

U.S. PATENT DOCUMENTS

| | | |
|---|---|---|
| 2007/0053943 A1 | 3/2007 | Wang et al. |
| 2007/0059253 A1 | 3/2007 | Popp et al. |
| 2007/0069046 A1 | 3/2007 | Eini et al. |
| 2007/0071688 A1 | 3/2007 | Illel et al. |
| 2007/0098647 A1 | 5/2007 | Neubourg |
| 2007/0111956 A1 | 5/2007 | Matsushima et al. |
| 2007/0134174 A1 | 6/2007 | Irwin et al. |
| 2007/0140998 A1 | 6/2007 | Kato et al. |
| 2007/0140999 A1 | 6/2007 | Puglia et al. |
| 2007/0141086 A1 | 6/2007 | Ohara et al. |
| 2007/0142263 A1 | 6/2007 | Stahl et al. |
| 2007/0148112 A1 | 6/2007 | Dingley et al. |
| 2007/0148194 A1 | 6/2007 | Amiji et al. |
| 2007/0154402 A1 | 7/2007 | Trumbore et al. |
| 2007/0160548 A1 | 7/2007 | Riccardi et al. |
| 2007/0166274 A1 | 7/2007 | Mazur et al. |
| 2007/0224143 A1 | 9/2007 | Konis |
| 2007/0237724 A1 | 10/2007 | Abram et al. |
| 2007/0264317 A1 | 11/2007 | Yosha et al. |
| 2007/0271235 A1 | 11/2007 | Frank et al. |
| 2007/0281999 A1 | 12/2007 | Fox et al. |
| 2007/0292355 A1 | 12/2007 | Tamarkin et al. |
| 2007/0292359 A1 | 12/2007 | Friedman et al. |
| 2007/0292461 A1 | 12/2007 | Tamarkin et al. |
| 2008/0008397 A1 | 1/2008 | Kisilev |
| 2008/0015263 A1 | 1/2008 | Bolotin et al. |
| 2008/0015271 A1 | 1/2008 | Abram et al. |
| 2008/0031907 A1 | 2/2008 | Tamarkin et al. |
| 2008/0031908 A1 | 2/2008 | Aubrun-Sonneville et al. |
| 2008/0035155 A1 | 2/2008 | Dahl |
| 2008/0044444 A1 | 2/2008 | Tamarkin et al. |
| 2008/0050317 A1 | 2/2008 | Tamarkin et al. |
| 2008/0058055 A1 | 3/2008 | LeMay et al. |
| 2008/0063682 A1 | 3/2008 | Cashman et al. |
| 2008/0069779 A1 | 3/2008 | Tamarkin et al. |
| 2008/0131378 A1 | 6/2008 | Keller et al. |
| 2008/0138293 A1 | 6/2008 | Tamarkin et al. |
| 2008/0138296 A1 | 6/2008 | Tamarkin et al. |
| 2008/0152596 A1 | 6/2008 | Friedman et al. |
| 2008/0153789 A1 | 6/2008 | Dmowski et al. |
| 2008/0166303 A1 | 7/2008 | Tamarkin et al. |
| 2008/0167376 A1 | 7/2008 | Bar-Or et al. |
| 2008/0181854 A1 | 7/2008 | Eini et al. |
| 2008/0188445 A1 | 8/2008 | Muldoon et al. |
| 2008/0188446 A1 | 8/2008 | Muldoon et al. |
| 2008/0193762 A1 | 8/2008 | Dubertret et al. |
| 2008/0206155 A1 | 8/2008 | Tamarkin et al. |
| 2008/0206161 A1 | 8/2008 | Tamarkin et al. |
| 2008/0241079 A1 | 10/2008 | Neubourg |
| 2008/0253973 A1 | 10/2008 | Tamarkin et al. |
| 2008/0255498 A1 | 10/2008 | Houle |
| 2008/0260655 A1 | 10/2008 | Tamarkin et al. |
| 2008/0292560 A1 | 11/2008 | Tamarkin et al. |
| 2008/0311167 A1 | 12/2008 | Oronsky et al. |
| 2008/0317679 A1 | 12/2008 | Tamarkin et al. |
| 2009/0017147 A1 | 1/2009 | Lintner et al. |
| 2009/0053290 A1 | 2/2009 | Sand et al. |
| 2009/0061001 A1 | 3/2009 | Hougaz |
| 2009/0093514 A1 | 4/2009 | Statham et al. |
| 2009/0130029 A1 | 5/2009 | Tamarkin et al. |
| 2009/0131488 A1 | 5/2009 | Harel et al. |
| 2009/0175799 A1 | 7/2009 | Tamarkin et al. |
| 2009/0214628 A1 | 8/2009 | De Rijk |
| 2009/0291917 A1 | 11/2009 | Akama et al. |
| 2010/0111879 A1 | 5/2010 | Tamarkin et al. |
| 2010/0221194 A1 | 9/2010 | Loupenok |
| 2010/0247449 A1 | 9/2010 | Graupe et al. |
| 2010/0286417 A1 | 11/2010 | Mendes et al. |
| 2011/0002969 A1 | 1/2011 | Serraima et al. |
| 2011/0097279 A1 | 4/2011 | Tamarkin et al. |
| 2011/0207765 A1 | 8/2011 | Van Den Bussche et al. |
| 2011/0262542 A1 | 10/2011 | Ashley |
| 2012/0064136 A1 | 3/2012 | Baker, Jr. et al. |
| 2012/0082632 A1 | 4/2012 | Phillips et al. |
| 2012/0087872 A1 | 4/2012 | Tamarkin et al. |
| 2012/0093876 A1 | 4/2012 | Ouster, III |
| 2012/0128598 A1 | 5/2012 | Trumbore et al. |
| 2012/0141384 A1 | 6/2012 | Tamarkin |
| 2012/0148503 A1 | 6/2012 | Tamarkin et al. |
| 2012/0156144 A1 | 6/2012 | Tamarkin et al. |
| 2012/0164087 A1 | 6/2012 | Carter |
| 2012/0181201 A1 | 7/2012 | Heggie |
| 2012/0237453 A1 | 9/2012 | Tamarkin et al. |
| 2013/0053353 A1 | 2/2013 | Tamarkin et al. |
| 2013/0064777 A1 | 3/2013 | Tamarkin et al. |
| 2013/0115173 A1 | 5/2013 | Trumbore et al. |
| 2013/0161351 A1 | 6/2013 | Eini et al. |
| 2013/0164225 A1 | 6/2013 | Tamarkin et al. |
| 2013/0189195 A1 | 7/2013 | Tamarkin et al. |
| 2013/0189196 A1 | 7/2013 | Tamarkin et al. |
| 2013/0251644 A1 | 9/2013 | Majhi et al. |
| 2013/0261565 A1 | 10/2013 | Wong et al. |
| 2013/0295022 A1 | 11/2013 | Friedman et al. |
| 2013/0296387 A1 | 11/2013 | Saad |
| 2014/0086848 A1 | 3/2014 | Tamarkin et al. |
| 2014/0121188 A1 | 5/2014 | Tamarkin et al. |
| 2014/0140937 A1 | 5/2014 | Gurge et al. |
| 2014/0182585 A1 | 7/2014 | Tamarkin et al. |
| 2014/0186269 A1 | 7/2014 | Tamarkin et al. |
| 2014/0221320 A1 | 8/2014 | Joks et al. |
| 2014/0228355 A1 | 8/2014 | Kortagere et al. |
| 2014/0242016 A1 | 8/2014 | Binks et al. |
| 2014/0248219 A1 | 9/2014 | Tamarkin et al. |
| 2015/0025060 A1 | 1/2015 | Tamarkin et al. |
| 2015/0098907 A1 | 4/2015 | Tamarkin et al. |
| 2015/0141381 A1 | 5/2015 | Levy et al. |
| 2015/0157586 A1 | 6/2015 | Tamarkin et al. |
| 2015/0164922 A1 | 6/2015 | Tamarkin et al. |
| 2015/0174144 A1 | 6/2015 | Bowser et al. |
| 2015/0196570 A1 | 7/2015 | Tamarkin et al. |
| 2015/0209296 A1 | 7/2015 | Yamamoto |
| 2016/0128944 A1 | 5/2016 | Chawrai et al. |
| 2016/0158261 A1 | 6/2016 | Friedman et al. |
| 2016/0213757 A1 | 7/2016 | Edelson et al. |
| 2016/0279152 A1 | 9/2016 | Chen et al. |
| 2016/0287615 A1 | 10/2016 | Chan et al. |
| 2016/0354473 A1 | 12/2016 | Tamarkin et al. |
| 2016/0361252 A1 | 12/2016 | Franke |
| 2016/0361320 A1 | 12/2016 | Zhao et al. |
| 2017/0014517 A1 | 1/2017 | Tamarkin |
| 2017/0049712 A1 | 2/2017 | Bhalani et al. |
| 2017/0119665 A1 | 5/2017 | Tamarkin et al. |
| 2017/0157175 A1 | 6/2017 | Tamarkin et al. |
| 2017/0172857 A1 | 6/2017 | Tamarkin et al. |
| 2017/0181970 A1 | 6/2017 | Tamarkin et al. |
| 2017/0216334 A1 | 8/2017 | Tamarkin et al. |
| 2017/0231909 A1 | 8/2017 | Tamarkin et al. |
| 2017/0274084 A1 | 9/2017 | Friedman et al. |
| 2017/0348418 A1 | 12/2017 | Tamarkin et al. |
| 2017/0354597 A1 | 12/2017 | Tamarkin et al. |
| 2018/0147218 A1 | 5/2018 | Tamarkin et al. |
| 2018/0214558 A1 | 8/2018 | Tamarkin et al. |
| 2018/0235984 A1 | 8/2018 | Eini et al. |
| 2019/0000980 A1 | 1/2019 | Tamarkin et al. |
| 2019/0008795 A1 | 1/2019 | Waugh |
| 2019/0021697 A1 | 1/2019 | Specht et al. |
| 2019/0022000 A1 | 1/2019 | Tamarkin et al. |
| 2019/0022001 A1 | 1/2019 | Tamarkin et al. |
| 2019/0029958 A1 | 1/2019 | Tamarkin et al. |
| 2019/0054106 A1 | 2/2019 | Tamarkin et al. |
| 2019/0076339 A1 | 3/2019 | Tamarkin et al. |
| 2019/0076451 A1 | 3/2019 | Friedman et al. |
| 2019/0091149 A1 | 3/2019 | Tamarkin et al. |
| 2019/0126027 A1 | 5/2019 | O'Neill |
| 2019/0134204 A1 | 5/2019 | Tamarkin et al. |
| 2019/0255078 A1 | 8/2019 | Chen et al. |
| 2019/0262266 A1 | 8/2019 | Moen et al. |
| 2020/0046739 A1 | 2/2020 | Chen et al. |
| 2020/0222358 A1 | 7/2020 | Sajic et al. |
| 2020/0230035 A1 | 7/2020 | Scherer et al. |
| 2020/0276458 A1 | 9/2020 | Daniels |
| 2020/0289381 A1 | 9/2020 | Neubourg |

(56) References Cited

U.S. PATENT DOCUMENTS

| | | | |
|---|---|---|---|
| 2021/0000842 A1 | 1/2021 | Eini et al. | |
| 2021/0015927 A1 | 1/2021 | Tamarkin et al. | |
| 2021/0069335 A1 | 3/2021 | Tamarkin et al. | |

FOREIGN PATENT DOCUMENTS

| | | |
|---|---|---|
| CA | 2114537 A1 | 2/1993 |
| CA | 2154438 A1 | 1/1996 |
| CA | 2422244 A1 | 9/2003 |
| CA | 2502986 A1 | 5/2004 |
| CA | 2534372 A1 | 10/2005 |
| CH | 639913 A5 | 12/1983 |
| CN | 1528326 A | 9/2004 |
| DE | 1 882 100 U | 11/1963 |
| DE | 1926796 A1 | 3/1970 |
| DE | 2 608 226 A1 | 9/1977 |
| DE | 4140474 A1 | 6/1993 |
| DE | 10009233 A1 | 8/2000 |
| DE | 10138495 A1 | 2/2003 |
| DE | 102004016710 A1 | 10/2005 |
| EP | 0 052 404 A2 | 5/1982 |
| EP | 0 156 507 A1 | 10/1985 |
| EP | 0 186 453 A2 | 7/1986 |
| EP | 0 213 827 A2 | 3/1987 |
| EP | 0 214 865 A2 | 3/1987 |
| EP | 0 270 316 A2 | 6/1988 |
| EP | 0 297 436 A2 | 1/1989 |
| EP | 0 336 812 A2 | 10/1989 |
| EP | 0 414 920 A1 | 3/1991 |
| EP | 0 211 550 B1 | 4/1991 |
| EP | 0 216 856 B1 | 7/1991 |
| EP | 0 454 102 A2 | 10/1991 |
| EP | 0 326 196 B2 | 3/1992 |
| EP | 0 484 530 A1 | 5/1992 |
| EP | 0 485 299 A1 | 5/1992 |
| EP | 0 488 089 A1 | 6/1992 |
| EP | 0 528 190 A1 | 2/1993 |
| EP | 0 552 612 A2 | 7/1993 |
| EP | 0 569 773 A2 | 11/1993 |
| EP | 0 404 376 B1 | 3/1994 |
| EP | 0 598 412 A2 | 5/1994 |
| EP | 0 391 124 B1 | 6/1995 |
| EP | 0 662 431 A2 | 7/1995 |
| EP | 0 535 327 B1 | 10/1996 |
| EP | 0 738 516 A1 | 10/1996 |
| EP | 0 757 959 A1 | 2/1997 |
| EP | 0 824 911 A2 | 2/1998 |
| EP | 0 829 259 A1 | 3/1998 |
| EP | 0 676 198 B1 | 10/1998 |
| EP | 0 979 654 A1 | 2/2000 |
| EP | 0 993 827 A1 | 4/2000 |
| EP | 1 025 836 A1 | 8/2000 |
| EP | 1 055 425 A2 | 11/2000 |
| EP | 0 506 197 B2 | 7/2001 |
| EP | 1 215 258 A2 | 6/2002 |
| EP | 1 287 813 A1 | 3/2003 |
| EP | 1 308 169 A1 | 5/2003 |
| EP | 1 375 386 A1 | 1/2004 |
| EP | 0 504 301 B1 | 3/2004 |
| EP | 1 428 521 A2 | 6/2004 |
| EP | 1 438 946 A1 | 7/2004 |
| EP | 1 189 579 B1 | 9/2004 |
| EP | 1 475 381 A1 | 11/2004 |
| EP | 1 500 385 A1 | 1/2005 |
| EP | 1 537 916 A1 | 6/2005 |
| EP | 1 600 185 A1 | 11/2005 |
| EP | 0 928 608 B1 | 3/2006 |
| EP | 1 653 932 A1 | 5/2006 |
| EP | 1 734 927 A1 | 12/2006 |
| EP | 1 758 547 A1 | 3/2007 |
| EP | 1 483 001 B1 | 11/2007 |
| EP | 1 584 324 B1 | 11/2007 |
| EP | 1 889 609 A2 | 2/2008 |
| EP | 1 902 706 A1 | 3/2008 |
| EP | 2 129 383 A1 | 12/2009 |
| EP | 2 422 768 A2 | 2/2012 |
| EP | 2 494 959 A1 | 9/2012 |
| FR | 2 456 522 A1 | 12/1980 |
| FR | 2 591 331 A1 | 6/1987 |
| FR | 2 640 942 A2 | 6/1990 |
| FR | 2 736 824 A1 | 1/1997 |
| FR | 2 774 595 A1 | 8/1999 |
| FR | 2 789 371 A1 | 8/2000 |
| FR | 2 793 479 A1 | 11/2000 |
| FR | 2 814 959 A1 | 4/2002 |
| FR | 2 833 246 A1 | 6/2003 |
| FR | 2 840 903 A1 | 12/2003 |
| FR | 2 843 373 A1 | 2/2004 |
| FR | 2 845 672 A1 | 4/2004 |
| FR | 2 848 998 A1 | 6/2004 |
| FR | 2 860 976 | 4/2005 |
| FR | 2 915 891 A1 | 11/2008 |
| GB | 808 104 A | 1/1959 |
| GB | 808 105 A | 1/1959 |
| GB | 922 930 A | 4/1963 |
| GB | 933 486 A | 8/1963 |
| GB | 998 490 A | 7/1965 |
| GB | 1 026 831 A | 4/1966 |
| GB | 1 033 299 A | 6/1966 |
| GB | 1 081 949 A | 9/1967 |
| GB | 1 121 358 A | 7/1968 |
| GB | 1 162 684 A | 8/1969 |
| GB | 1 170 152 A | 11/1969 |
| GB | 1 201 918 A | 8/1970 |
| GB | 1 347 950 A | 2/1974 |
| GB | 1 351 761 A | 5/1974 |
| GB | 1 351 762 A | 5/1974 |
| GB | 1 353 381 A | 5/1974 |
| GB | 1 376 649 A | 12/1974 |
| GB | 1 397 285 A | 6/1975 |
| GB | 1 408 036 A | 10/1975 |
| GB | 1 457 671 A | 12/1976 |
| GB | 1 489 672 A | 10/1977 |
| GB | 2 004 746 A | 4/1979 |
| GB | 1 561 423 A | 2/1980 |
| GB | 2 114 580 A | 8/1983 |
| GB | 2 166 651 A | 5/1986 |
| GB | 2 153 686 B | 7/1987 |
| GB | 2 172 298 B | 11/1988 |
| GB | 2 206 099 A | 12/1988 |
| GB | 2 337 461 A | 11/1999 |
| GB | 2 367 809 A | 4/2002 |
| GB | 2 406 330 A | 3/2005 |
| GB | 2 406 791 B | 2/2008 |
| GB | 2 474 930 A | 5/2011 |
| IL | 49491 A | 9/1979 |
| IL | 152 486 A | 5/2003 |
| JP | 55-069682 A | 5/1980 |
| JP | 56-039815 A | 4/1981 |
| JP | 57-044429 A | 3/1982 |
| JP | 60-001113 A | 1/1985 |
| JP | 61-275395 A | 12/1986 |
| JP | 62-241701 A | 10/1987 |
| JP | 63-119420 A | 5/1988 |
| JP | 01-100111 A | 4/1989 |
| JP | 01-156906 A | 6/1989 |
| JP | 02-184614 A | 7/1990 |
| JP | 02-255890 A | 10/1990 |
| JP | 03-050289 A | 3/1991 |
| JP | 04-51958 A | 2/1992 |
| JP | 04-282311 A | 10/1992 |
| JP | 04-312521 A | 11/1992 |
| JP | 05-070340 A | 3/1993 |
| JP | 05-213734 A | 8/1993 |
| JP | 06-100414 A | 4/1994 |
| JP | 06-263630 A | 9/1994 |
| JP | 06-329532 A | 11/1994 |
| JP | 07-215835 A | 8/1995 |
| JP | 08-040899 A | 2/1996 |
| JP | 08-501529 A | 2/1996 |
| JP | 08-119831 A | 5/1996 |
| JP | 08-165218 A | 6/1996 |
| JP | 08-277209 A | 10/1996 |
| JP | 09-84855 A | 3/1997 |

(56) References Cited

FOREIGN PATENT DOCUMENTS

| | | |
|---|---|---|
| JP | 09-099553 A | 4/1997 |
| JP | 09-110636 A | 4/1997 |
| JP | 10-114619 A | 5/1998 |
| JP | 10-332456 A | 12/1998 |
| JP | 11-501045 A | 1/1999 |
| JP | 11-250543 A | 9/1999 |
| JP | 2000-017174 A | 1/2000 |
| JP | 2000-080017 A | 3/2000 |
| JP | 2000-128734 A | 5/2000 |
| JP | 2000-191429 A | 7/2000 |
| JP | 2000-239140 A | 9/2000 |
| JP | 2000-351726 A | 12/2000 |
| JP | 2000-354623 A | 12/2000 |
| JP | 2001-002526 A | 1/2001 |
| JP | 2001-019606 A | 1/2001 |
| JP | 2001-072963 A | 3/2001 |
| JP | 2002-012513 A | 1/2002 |
| JP | 2002-047136 A | 2/2002 |
| JP | 2002-524490 A | 8/2002 |
| JP | 2002-302419 A | 10/2002 |
| JP | 2003-012511 A | 1/2003 |
| JP | 2003-055146 A | 2/2003 |
| JP | 2004-047136 A | 2/2004 |
| JP | 2004-250435 A | 9/2004 |
| JP | 2004-348277 A | 12/2004 |
| JP | 2005-314323 A | 11/2005 |
| JP | 2005-350378 A | 12/2005 |
| JP | 2006-008574 A | 1/2006 |
| JP | 2006-036317 A | 2/2006 |
| JP | 2006-103799 A | 4/2006 |
| JP | 2006-525145 A | 11/2006 |
| JP | 2007-131539 A2 | 5/2007 |
| JP | 2007-155667 A | 6/2007 |
| JP | 2007-326996 A | 12/2007 |
| KR | 0143232 A | 7/1998 |
| KR | 2001-003063 A | 1/2001 |
| NZ | 520014 A | 5/2005 |
| NZ | 540166 A | 6/2007 |
| RU | 2277501 C2 | 6/2006 |
| UA | 66796 C2 | 7/2001 |
| WO | WO 82/001821 A1 | 6/1982 |
| WO | WO 86/05389 A1 | 9/1986 |
| WO | WO 88/01502 A1 | 3/1988 |
| WO | WO 88/01863 A1 | 3/1988 |
| WO | WO 88/08316 A1 | 11/1988 |
| WO | WO 89/06537 A1 | 7/1989 |
| WO | WO 90/05774 A1 | 5/1990 |
| WO | WO 91/11991 A1 | 8/1991 |
| WO | WO 92/00077 A1 | 1/1992 |
| WO | WO 92/005142 A1 | 4/1992 |
| WO | WO 92/05763 A1 | 4/1992 |
| WO | WO 92/11839 A1 | 7/1992 |
| WO | WO 92/13602 A1 | 8/1992 |
| WO | WO 93/025189 A1 | 12/1993 |
| WO | WO 94/006440 A1 | 3/1994 |
| WO | WO 96/03115 A1 | 2/1996 |
| WO | WO 96/19921 A1 | 7/1996 |
| WO | WO 96/24325 A1 | 8/1996 |
| WO | WO 96/26711 A1 | 9/1996 |
| WO | WO 96/27376 A1 | 9/1996 |
| WO | WO 96/39119 A1 | 12/1996 |
| WO | WO 97/03638 A1 | 2/1997 |
| WO | WO 97/39745 A1 | 10/1997 |
| WO | WO 98/17282 A1 | 4/1998 |
| WO | WO 98/18472 A1 | 5/1998 |
| WO | WO 98/19654 A1 | 5/1998 |
| WO | WO 98/21955 A1 | 5/1998 |
| WO | WO 98/23291 A1 | 6/1998 |
| WO | WO 98/31339 A1 | 7/1998 |
| WO | WO 98/36733 A2 | 8/1998 |
| WO | WO 98/52536 A1 | 11/1998 |
| WO | WO 99/08649 A2 | 2/1999 |
| WO | WO 99/20250 A1 | 4/1999 |
| WO | WO 99/37282 A2 | 7/1999 |
| WO | WO 99/53923 A1 | 10/1999 |
| WO | WO 2000/09082 A1 | 2/2000 |
| WO | WO 2000/15193 A1 | 3/2000 |
| WO | WO 2000/23051 A1 | 4/2000 |
| WO | WO 2000/33825 A2 | 6/2000 |
| WO | WO 2000/38731 A1 | 7/2000 |
| WO | WO 2000/61076 A1 | 10/2000 |
| WO | WO 2000/62776 A1 | 10/2000 |
| WO | WO 2000/72805 A1 | 12/2000 |
| WO | WO 2000/76461 A2 | 12/2000 |
| WO | WO 2001/01949 A1 | 1/2001 |
| WO | WO 2001/05366 A1 | 1/2001 |
| WO | WO 2001/08681 A1 | 2/2001 |
| WO | WO 2001/10961 A1 | 2/2001 |
| WO | WO 2001/53198 A1 | 7/2001 |
| WO | WO 2001/54212 A1 | 7/2001 |
| WO | WO 2001/54679 A2 | 8/2001 |
| WO | WO 2001/62209 A2 | 8/2001 |
| WO | WO 2001/70242 A2 | 9/2001 |
| WO | WO 2001/76579 A1 | 10/2001 |
| WO | WO 2001/82880 A3 | 11/2001 |
| WO | WO 2001/82890 A1 | 11/2001 |
| WO | WO 2001/85102 A2 | 11/2001 |
| WO | WO 2001/85128 A2 | 11/2001 |
| WO | WO 2001/95728 A1 | 12/2001 |
| WO | WO 2002/00820 A1 | 1/2002 |
| WO | WO 2002/07685 A2 | 1/2002 |
| WO | WO 2002/15860 A1 | 2/2002 |
| WO | WO 2002/15873 A2 | 2/2002 |
| WO | WO 2002/24161 A1 | 3/2002 |
| WO | WO 2002/28435 A1 | 4/2002 |
| WO | WO 2002/41847 A1 | 5/2002 |
| WO | WO 2002/43490 A1 | 6/2002 |
| WO | WO 2002/062324 A2 | 8/2002 |
| WO | WO 2002/078667 A1 | 10/2002 |
| WO | WO 2002/087519 A2 | 11/2002 |
| WO | WO 2003/000223 A1 | 1/2003 |
| WO | WO 2003/002082 A1 | 1/2003 |
| WO | WO 2003/005985 A1 | 1/2003 |
| WO | WO 2003/013984 A1 | 2/2003 |
| WO | WO 2003/015699 A2 | 2/2003 |
| WO | WO 2003/051294 A2 | 6/2003 |
| WO | WO 2003/053292 A1 | 7/2003 |
| WO | WO 2003/055445 A2 | 7/2003 |
| WO | WO 2003/055454 A1 | 7/2003 |
| WO | WO 2003/070301 A1 | 8/2003 |
| WO | WO 2003/071995 A1 | 9/2003 |
| WO | WO 2003/075851 A2 | 9/2003 |
| WO | WO 2003/092641 A1 | 11/2003 |
| WO | WO 2003/094873 A1 | 11/2003 |
| WO | WO 2003/097002 A1 | 11/2003 |
| WO | WO 2004/017962 A2 | 3/2004 |
| WO | WO 2004/037197 A2 | 5/2004 |
| WO | WO 2004/037225 A2 | 5/2004 |
| WO | WO 2004/003284 A1 | 8/2004 |
| WO | WO 2004/064769 A2 | 8/2004 |
| WO | WO 2004/064833 A1 | 8/2004 |
| WO | WO 2004/071479 A1 | 8/2004 |
| WO | WO 2004/078158 A2 | 9/2004 |
| WO | WO 2004/078896 A1 | 9/2004 |
| WO | WO 2004/093895 A1 | 11/2004 |
| WO | WO 2004/112780 A1 | 12/2004 |
| WO | WO 2005/009416 A2 | 2/2005 |
| WO | WO 2005/011567 A2 | 2/2005 |
| WO | WO 2005/018530 A2 | 3/2005 |
| WO | WO 2005/032522 A1 | 4/2005 |
| WO | WO 2005/044219 A1 | 5/2005 |
| WO | WO 2005/063224 A1 | 7/2005 |
| WO | WO 2005/065652 A1 | 7/2005 |
| WO | WO 2005/076697 A2 | 8/2005 |
| WO | WO 2005/097068 A1 | 10/2005 |
| WO | WO 2005/102282 A1 | 11/2005 |
| WO | WO 2005/102539 A1 | 11/2005 |
| WO | WO 2005/117813 A1 | 12/2005 |
| WO | WO 2006/003481 A2 | 1/2006 |
| WO | WO 2006/010589 A2 | 2/2006 |
| WO | WO 2006/011046 A1 | 2/2006 |
| WO | WO 2006/020682 A1 | 2/2006 |
| WO | WO 2006/028339 A1 | 3/2006 |
| WO | WO 2006/031271 A2 | 3/2006 |

(56) References Cited

FOREIGN PATENT DOCUMENTS

| WO | WO 2006/045170 A2 | 5/2006 |
|---|---|---|
| WO | WO 2006/079632 A1 | 8/2006 |
| WO | WO 2006/081327 A2 | 8/2006 |
| WO | WO 2006/091229 A2 | 8/2006 |
| WO | WO 2006/100485 A1 | 9/2006 |
| WO | WO 2006/120682 A2 | 11/2006 |
| WO | WO 2006/121610 A2 | 11/2006 |
| WO | WO 2006/122158 A2 | 11/2006 |
| WO | WO 2006/129161 A2 | 12/2006 |
| WO | WO 2006/131784 A1 | 12/2006 |
| WO | WO 2007/007208 A2 | 1/2007 |
| WO | WO 2007/010494 A1 | 1/2007 |
| WO | WO 2007/012977 A2 | 2/2007 |
| WO | WO 2007/023396 A2 | 3/2007 |
| WO | WO 2007/031621 A2 | 3/2007 |
| WO | WO 2007/039825 A2 | 4/2007 |
| WO | WO 2007/050543 A2 | 5/2007 |
| WO | WO 2007/054818 A2 | 5/2007 |
| WO | WO 2007/072216 A2 | 6/2007 |
| WO | WO 2007/082698 A1 | 7/2007 |
| WO | WO 2007/085902 A2 | 8/2007 |
| WO | WO 2007/099396 A2 | 9/2007 |
| WO | WO 2007/111962 A2 | 10/2007 |
| WO | WO 2008/008397 A2 | 1/2008 |
| WO | WO 2008/010963 A2 | 1/2008 |
| WO | WO 2008/038147 A2 | 4/2008 |
| WO | WO 2008/041045 A1 | 4/2008 |
| WO | WO 2008/075207 A2 | 6/2008 |
| WO | WO 2008/087148 A2 | 7/2008 |
| WO | WO 2008/104734 A1 | 9/2008 |
| WO | WO 2008/110872 A2 | 9/2008 |
| WO | WO 2008/152444 A2 | 12/2008 |
| WO | WO 2009/007785 A2 | 1/2009 |
| WO | WO 2009/069006 A2 | 6/2009 |
| WO | WO 2009/072007 A2 | 6/2009 |
| WO | WO 2009/087578 A2 | 7/2009 |
| WO | WO 2009/090495 A2 | 7/2009 |
| WO | WO 2009/090558 A2 | 7/2009 |
| WO | WO 2009/098595 A2 | 8/2009 |
| WO | WO 2011/006026 A1 | 1/2011 |
| WO | WO 2011/013008 A2 | 2/2011 |
| WO | WO 2011/013009 A2 | 2/2011 |
| WO | WO 2011/026094 A2 | 3/2011 |
| WO | WO 2011/039637 A2 | 4/2011 |
| WO | WO 2011/039638 A2 | 4/2011 |
| WO | WO 2011/064631 A1 | 6/2011 |
| WO | WO 2011/106026 A1 | 9/2011 |
| WO | WO 2011/138678 A2 | 11/2011 |
| WO | WO 2012/100097 A2 | 7/2012 |
| WO | WO 2012/100097 A3 | 7/2012 |
| WO | WO 2013/136192 A2 | 9/2013 |
| WO | WO 2014/134394 A1 | 9/2014 |
| WO | WO 2014/134427 A1 | 9/2014 |
| WO | WO 2014/151347 A1 | 9/2014 |
| WO | WO 2014/201541 A1 | 12/2014 |
| WO | WO 2015/075640 A1 | 5/2015 |
| WO | WO 2015/114320 A1 | 8/2015 |
| WO | WO 2015/153864 A2 | 10/2015 |
| WO | WO 2016/154232 A2 | 9/2016 |
| WO | WO 2017/029647 A1 | 2/2017 |
| WO | WO 2017/030555 A1 | 2/2017 |
| WO | WO 2017/089809 A1 | 6/2017 |
| WO | WO 2019/014380 A1 | 1/2019 |
| WO | WO 2019/082090 A1 | 5/2019 |
| WO | WO 2020/089891 A1 | 5/2020 |
| WO | WO 2020/130035 A1 | 6/2020 |

OTHER PUBLICATIONS

"Suppositories?" CareCure Community, SCI Forum [online]. http://sci.rutgers.edu/forum/showthread.php?4176-Suppositories. Published: Apr. 16, 2002, 3 pages.
1058. Benzalkonium Chloride; 2350. Citric Acid; 6143. Methyl Salicylate. The Merck Index: An Encyclopedia of Chemicals, Drugs, and Biologicals. 13th Edition, 2001, pp. 181, 405-406, 1090-1091, 1556.
242. Allantoin, The Merck Index: An Encyclopedia of Chemicals, Drugs, and Biologicals. 10th edition, Merck & Co., Inc., 1983, p. 39.
Abdullah, G.Z. et al. (Jan. 2013) "Carbopol 934, 940 and Ultrez 10 as viscosity modifiers of palm olein esters based nano-scaled emulsion containing ibuprofen" Pak J Pharm Sci, 26(1):75-83.
Abrams et al., "Ciclopirox gel treatment of scalp seborrheic dermatitis," in: Shuster, S. (ed.) Hydroxy-Piridones as Antifungal Agents with Special Emphasis on Onychomycosis. Springer, Berlin, Heidelberg; 1999, Chapter 8, pp. 45-50.
Adachi, "Storage and Oxidative Stability of O/W/ Nano-emulsions," Foods Food Ingredients J. Jpn., 2004, 209(11), 1 page (Abstract).
Adisen et al., "Topical tetracycline in the treatment of acne vulgaris," J Drugs Dermatol., Oct. 2008, 7(10):953-955.
Alcohol SDA 40B, 200 Proof. Material Safety Data Sheets [online]. Retrieved from the Internet: http://www.pharmco-prod.com/pages/MSDS/SDA.sub.--40B.sub.--200.pdf, on Dec. 9, 2008. MSDS 044, Revision 2.1, Revision Date Dec. 2005, 2 pages.
Alcohol, Wikipedia, the free encyclopedia [online]. Last modified on Apr. 23, 2014. Retrieved on May 17, 2014, http://en.wikipedia.org/wiki/Alcohol, 17 pages.
Aldara™ (imiquimod) Cream. Highlights of Prescribing Information, Graceway Pharmaceuticals, LLC, Mar. 2007, 29 pages.
Allantoin, Römpp Online, retrieved on Sep. 23, 2015, https://roempp.thieme.de/roempp4.0/do/data/RD-O 1-01552, 5 pages.
Allen, The Art, Science, and Technology of Pharmaceutical Compounding, pp. 173-185 (1998).
Allen, The Art, Science, and Technology of Pharmaceutical Compounding, 2nd edition, pp. 250, 251, 263, 267-269, 287, 288, 301-305, tables 16-1 and 16-2 (2002).
Al-Mughrabi et al., "Effectiveness of Essential Oils and Their Combinations with Aluminum Starch Octenylsuccinate on Potato Storage Pathogens," TEOP, 2013, 16(1):23-31.
Ambrose et al., "In Vitro Studies of Water Activity and Bacterial Growth Inhibition of Sucrose-Polyethylene Glycol 400-Hydrogen Peroxide and Xylose-Polyethylene Glycol 400-Hydrogen Peroxide Pastes Used to Treat Infected Wounds," Antimicrobial Agents and Chemotherapy, Sep. 1991, 35(9):1799-1803.
Aminobenzoic Acid, Knovel, 2006, retrieved on Apr. 18, 2012, http://www.knovel.com/web/portal/knovel_content?p_p_id=EXT_KNOVEL_CONTENT . . . , 2 pages.
Ansel et al., Pharmaceutical Dosage Forms and Drug Delivery Systems, 7th ed., pp. 87-92, 250, 378-380, table 3.3 (1999).
Anton et al., "Water-in-oil nano-emulsion formation by the phase inversion temperature method: a novel and general concept, a new template for nanoencapsulation," Proceedings of the 33rd Annual Meeting and Exposition of the Controlled Release Society, Jul. 2006, Vienna, Austria, 2 pages.
Arct et al., "Common cosmetic hydrophilic ingredients as penetration modifiers of flavonoids," International Journal of Cosmetic Science, Dec. 2002, 24(6):357-366 (Abstract Only).
Arisan, Kozmetic ve Kisisel Bakim Urunleri Grubu, retrieved on Dec. 10, 2008, http://www.arisankimya.com/kozmetik.htm, 8 pages.
Arquad HTL8-MS, AkzoNobel Functional Applications, retrieved on Mar. 18, 2013, Retrieved from the Internet: <URL: http://sc.akzonobel.com/en/fa/Pages/product-detail.aspx?prodID=8764>, 1 page.
Aslam et al. (2015) "Emerging drugs for the treatment of acne" Expert Opin Emerging Drugs, 20:91-101.
Atopic Dermatitis/Eczema, ibabydoc.com, Copyright 2000, retrieved on Jan. 30, 2010, http://www.ibabydoc.com/online/diseaseeczema.asp 6 pages.
Attwood et al., Surfactant Systems: Their chemistry, pharmacy and biology, pp. 1-8 (1993).
Ausburger and Shangraw, "Bubble size analysis of high consistency aerosol foams and its relationship to foam rheology; Effects fo Container Emptying, Propellent Type, and Time," J. Pharma Sci, Apr. 1968, 57(4):624-631.
Austria, et al., "Stability of vitamin C derivatives in solution and topical formulations", Journal of Pharmaceutical and Biomedical Analysis, 1997, 15:795-801.

(56) References Cited

OTHER PUBLICATIONS

Barry and Badal, "Stability of minocycline, doxycycline, and tetracycline stored in agar plates and microdilution trays," Current Microbiology, 1978, 1:33-36.
Barry and Woodford, "Comparative bio-availability and activity of proprietary topical corticosteroid preparations: vasoconstrictor assays on thirty-one ointments," British J. Dermatology, 1975, 93:563-571.
Baskaran et al., "Poloxamer-188 improves capillary blood flow and tissue viability in a cutaneous burn wound," J. Surg. Res., 2001, 101(1):56-61.
Beauty Banter, "Interesting list of comedogenic ingredients!!!!!!!!!!!" QVC blog, Interesting list of comedogenic ingredients, 2014, 1-14.
Bell-Syer et al., "A systematic review of oral treatments for fungal infections of the skin of the feet," J. Dermatology. Treat., 2001, 12:69-74.
Ben-Et and Tatarsky "Application of NMR for the Determination of HLB Values of Nonionic Surfactants," Journal of the American Oil Chemists Society, Mar. 20, 1972, 49:499-500.
Bernstein and Harrison, "Effects of the Immunomodulating Agent R837 on Acute and Latent Herpes Simplex Virus Type 2 Infections," Antimicrobial Agents and Chemotherapy, Sep. 1989, 33(9):1511-1515.
Beuchat (Feb. 1983) "Influence of Water Activity on Growth, Metabolic Activities and Survival of Yeasts and Molds" *J Food Prot*, 46(2):135-141.
Blaney and Cook, "Topical use of tetracycline in the treatment of acne," Arch Dermatol, Jul. 1976, 112:971-973.
Blute et al., "Phase behaviour of alkyl glycerol ether surfactants", Physikalische Chemie/Physical Chemistry Tenside Surf. Det., 1998, 35(3):207-212.
Boehm et al., "Synthesis of high specific activity [.sup.3 H]-9-cis-retinoic acid and its application for identifying retinoids with unusual binding properties," J. Med. Chem., 1994, 37:408-414.
Bowles et al., "Protection against Minocycline Pigment Formation by Ascorbic Acid (Vitamin C)", Journal of Esthetic Dentistry, vol. 10/No. 4, pp. 182-186 (1998).
Brenes, et al., "Stability of Copigmented Anthocyanins and Ascorbic Acid in a Grape Juice Model System", J. Agric Food Chem, 2005, 53(1):49-56 (Abstract Only).
Brewer, "Gramicidin", 8 Profiles of Drug Substances, Excipients and Related Methodology, 43 pages (1979).
Brisaert, M. et al. (1996) "Investigation on the chemical stability of erythromycin in solutions using an optimization system" *Pharm World Sci*, 18(5):182-186.
Bronopol, 2-Bromo-2-Nuro-1,3-Propanediol, Chemical land, Jul. 17, 2006, retrieved on Jun. 4, 2011, http://chemicalland21.com/specialtychem/perchem/BRONOPOL.html, 4 pages.
Brown et al., "Structural dependence of flavonoid interactions with Cu2+ ions: implications for their antioxidant properties," Biochem. J., 1998, 330:1173-1178.
Buck and Guth, "Treatment of Vaginal Intraepithelial Neoplasia (Primarily Low Grade) with Imiquimod 5% Cream", Journal of Lower Genital Tract Disease, 2003, 7(3):290-293.
Bucks et al., "Bioavailability of Topically Administered Steroids: A "Mass Balance" Technique," J. Investigative Dermatology, 1988, 91(1):29-33.
Bunker and Dowd, "Alterations in Scalp Blood Flow after the Epicutaneous Application of 3% Minoxidil and 0.1% Hexyl Nicotinate in Alopecia," British Society for Investigative Dermatology, Sep. 1986, 117(5):668-669.
Burn Patients Need Vitamin D Supplements, NUTRAingredients. com, Jan. 23, 2004, retrieved on May 5, 2010, http://www.nutraingredients.com/Research/Burn-patients-need-vitamin-D-supplements, 1page.
Burton and Marshall, "Hypertrichosis due to minoxidil," British J. Dermatology, 1979, 101:593-595.
C12-15 Alkyl Benzoate, Paula's Choice Skincare, retrieved on Oct. 24, 2010, http://ww.cosmeticscop.com/cosmetic-ingredient-dictionary/definition/259/c12-15-alkyl-benzoate.aspx, 1 page.

Calvert, "Foam in Motion", Foams: Physics, Chemistry and Structure, pp. 27-37 (1989).
Campos and Silva, "Ascorbic Acid and Its Derivatives in Cosmetic Formulations", Cosmetics and Toiletries, 2000, 115(6):59-62 (Abstract Only.
Can Tuberous Sclerosis Be Prevented?, Sharecare, 2002, retrieved on Aug. 29, 2013, <URL: http://www.sharecare.com/health/autosomal-dominant-genetic-disorders/can-tuberous-sclerosis-be-prevented;jsessionid=850579B60520A907DE75930E061E60E6>, 2 pages.
Canavan et al. (2016) "Optimizing Non-Antibiotic Treatments for Patients with Acne: A Review" *Dermatol Ther*, 6:555-578.
Carapeti et al., "Topical diltiazem and bethanechol decrease anal sphincter pressure and heal anal fissures without side effects," Dis Colon Rectum, 2000, 43(10):1359-1362.
Carbowax 1000MSDS, Material Safety Data Sheet for Polyethylene glycol 1000 MSDS, last updated Nov. 6, 2008, retrieved on Dec. 13, 2008, http://www.sciencelab.com/xMSDS-Polyethylene.sub.-glycol.sub.-1000-9926-622, 6 pages.
Carelli et al., "Effect of Vehicles on Yohimbine Permeation Across Excised Hairless Mouse Skin", Pharm Acta Helv, Aug. 1978, 73(3):127-134 (Abstract Only).
Causes of Psoriasis, retrieved on Sep. 9, 2010, http://www.quickcare.org/skin/causes-of0psoriasis.html, 3 pages.
Cetearyl Alcohol, Natural Wellbeing, Copyright 2001-2012, retrieved on Apr. 10, 2014, http://www.naturalwellbeing.com/learning-center/Cetearyl_Alcohol, 3 pages.
Chebil et al., "Solubility of Flavonoids in Organic Solvents," J. Chem. Eng. Data, 2007, 52(5):1552-1556 (Abstract Only).
Chemical Characteristics, The Olive Oil Source, © 1998-2015, retrieved on Jun. 12, 2015, http://www.oliveoilsource.com/page/chemical-characteristics, 10 pages.
Cheshire and Freeman, "Disorders of Sweating," Semin Neurol, 2003, 23(4):399-406.
Chevrant-Breton et al., "Etude du Traitement Capillaire <<Bioscalin>> dans les Alopecies Diffuses de la Femme", Gazette Medicale, 1986, 93(17):75-79 (English Abstract).
Chiang et al., "Bioavailability Assessment of Topical Delivery Systems: In Vitro Delivery of Minoxidil from Prototypical Semi-Solid Formulations", Int. J. Pharm, 1989, 49(2):109-114 (Abstract Only).
Chinnian et al., "Photostability Profiles of Minoxidil Solutions", PDA J. Pharm Sci Technol., Mar.-Apr. 1996, 50(2):94-98 (English Abstract).
Chollet et al., "Development of a Topically Active Imiquimod Formulation", Pharmaceutical Development and Technology, 1999, 4(1):35-43.
Chollet et al., "The Effect of Temperatures on the Solubility of Imiquimod in Isostearic Acid", Abstract 3031, Pharmaceutical Research, Nov. 1997, 14(11 Supplemental):S475.
Chrysos et al., "Effect of nifedipine on rectoanal motility," Dis Colon Rectum, Feb. 1996, 39(2):212-216.
Clobetasol Propionate Cream and Ointment, Apr. 2006, retrieved Jul. 3, 2014, http://dailymed.nlm.nih.gov/dailymed/archives/fdaDrugInfo.cfm?archiveid=994, 7 pages.
Cloez-Tayarani et al., "Differential effect of serotonin on cytokine production in lipopolysaccharide-stimulated human peripheral blood mononuclear cells: involvement of 5-hydroxytryptamine2A receptors," Int. Immunol., 2003, 15:233-240.
Coal Tars and Coal-Tar Pitches, *Report on Carcinogens, Twelfth Edition*, 2011, 3 pages.
Coatzee et al., "Acceptability and feasibility of Micralax® applicators and of methyl cellulose gel placebo for large-scale clinical trials of vaginal microbicides," AIDS, 2001, 15:1837-1842.
Coconut Oil, Wikipedia, the free encyclopedia, retrieved on Jul. 3, 2015, https://en.wikipedia.org/wiki/Coconut_oil, 8 pages.
Codex Standard for Olive Oils and Olive Pomace Oils Codex Stan 33-1981, Adopted in 1981, recently amended 2013, 8 pages.
Cole and Gazewood, "Diagnosis and Treatment of Impetigo," American Family Physical Website, 2007, http://www.aafp.org/afp, 6 pages.

(56) References Cited

OTHER PUBLICATIONS

Colloidal Silica, W.R. Grace & Co. Enriching Lives, Everywhere™, 2011, retrieved on Jun. 4, 2011, http://www.grace.com/engineeredmaterials/materialsciences/colloidalsilica/default.aspx, 4 pages.
Communication of a Notice of Opposition in European Application No. 03772600.7, dated Jan. 13, 2015, 36 pages.
Cook and Mortenson, "Nifedipine for treatment of anal fissures," Dis Colon Rectum, 2000, 43(3):430-431.
Craig, D.Q.M. et al. (Jul. 1994) "An investigation into the structure and properties of Carbopol 934 gels using dielectric spectroscopy and oscillatory rheometry" *J Controlled Rel*, 30(3):213-223 (Abstract).
Cremophor A Grades, BASF The Chemical Company, Jan. 2008, 6 pages.
Croda Crop Care, Arlacel 165, 2011, retrieved on Aug. 3, 2015, http://www.crodapersonalcare.com/home.aspx?view=dtl&d=content&s=157&r=401&p=2578&productName=&inciname=&application=&subapplication=&productfunction=&consumerbenefit=&prodID=1926, 2 pages.
Croda Product Care Europe, Cetomacrogol 1000, 2011, retrieved on Aug. 3, 2015, http://www.crodapersonalcare.com/home.aspx?view=dtl&d=content&s=157&r=273&p=1859&productName=&inciname=&chemicaltype=&application=&subapplication=&productfunction=&consumerbenefit=&prodID=27, 1 page.
Crohn's Disease, Merck Manual Home Edition, retrieved on Jan. 16, 2013, <http://www.merckmanuals.com/home/digestive_disorders/inflammatory_bowel_diseases_ibd/crohn_disease.html?qt=crohn's disease&alt=sh>, 3 pages.
Cunha, "Minocycline versus Doxycycline in the treatment of Lyme Neuroborreliosis," Clin. Infect. Diseases, 2000, 30: 237-238.
Dacarbazine, Chemical Book, 2010, retrieved on Oct. 18, 2013, <URL: http://www.chemicalbook.com/ChemicalProductProperty_EN_CB7710656.htm>, 2 pages.
Dalby et al., "Determination of Drug Solubility in Aerosol Propellants," Pharmaceutical Research, 1991, 8(9):1206-1209.
Dawber and Rundegren, "Hypertrichosis in Females Applying Minoxidil Topical Solution and in Normal Controls", JEADV, 2003, 17:271-275.
Declaration Pursuant to 37 C.F.R. §1.132 of Dr. Mohammad Salman, dated Dec. 28, 2015, filed in U.S. Appl. No. 14/074,868.
Declaration Pursuant to 37 C.F.R. §1.132 of Dr. Mohammad Salman, dated May 19, 2016, filed in U.S. Appl. No. 14/074,868.
Declaration Pursuant to 37 C.F.R. §1.132 of Dr. Mohammad Salman, dated Jul. 19, 2016, filed in U.S. Appl. No. 14/074,868.
Denatonium Benzoate, retrieved Dec. 9, 2008, http://www.newdruginfo.com/pharmaceopeia/usp28/v28230/usp28nf23s0_m-22790.htm, 2 pages.
Dentinger, et al., "Stability of Nifedipine in an Extemporaneously Compounded Oral Solution", American Journal of Health-System Pharmacy, 2003, 60(10):1019-1022 (English Abstract).
Derivative, Merriam Webster Online Dictionary, retrieved on Jul. 5, 2008, http://www.merriam-webster.com/cgi-bin/dictionary?book=dictionary&va=derivative, 1 page.
Devos and Miller, "Antisense Oligonucleotides: Treating neurodegeneration at the Level of RNA," Neurotherapeutics, 2013, 10:486-497.
Diethyltoluamide, Wikipedia, the free encyclopedia, retrieved on Sep. 11, 2015, https://de.wikipedia.org/wiki/Diethyltoluamid, 12 pages.
Dimethylphthalate, Wikipedia, the free encyclopedia, retrieved on Sep. 11, 2015, http://de.wikipedia.org/wiki/Dimethylphthalat, 8 pages.
Disorder, American Heritage Dictionary of the English Language, 2007, retrieved on Oct. 9, 2010, http://www.credoreference.com/entry/hmdictenglang/disorder, 1 page.
Donnelly et al., Novel Delivery Systems for Transdermal and Intradermal Drug Delivery, p. 103.
Draelos, "Antiperspirants and the Hyperhidrosis Patients," Dermatologic Therapy, 2001, 14:220-224.
Durian et al., "Scaling behavior in shaving cream," The American Physical Society, Dec. 1991, 44(12):R7902-7905.
Durmortier et al., "A review of poloxamer 407 pharmaceutical and pharmacological characteristics," Pharmaceutical Res., Dec. 2006, 23(12):2709-2728.
E7023 Ethanol 200 Proof (Absolute), Sigma-Aldrich Co., © 2008, retrieved on Dec. 9, 2008, http://www.sigmaaldrich.com/catalog/ProductDetail.do?N4=E7023SIAL&N5=SEAR-CH.sub.--CONCAT.sub.--PNOBRAND.sub.--KEY&F=SPEC, 2 pages.
Ebadi et al., "Healing effect of topical nifedipine on skin wounds of diabetic rats," DARU, 2003, 11(1):19-22.
Edens et al., "Storage Stability and Safety of Active Vitamin C in a New Dual-Chamber Dispenser", Journal of Applied Cosmetology, 1999, 17(4):136-143 (English Abstract).
Edirisinghe et al., "Effect of fatty acids on endothelium-dependent relaxation in the rabbit aorta", Clin Sci, Aug. 2006, 111(2): 145-51.
Edwards, "Imiquimod in Clinical Practice," J. Am Acad Dermatol., Jul. 2000 43(1, Pt 2):S12-S17 (English Abstract).
Effendy and Maibach "Surfactants and Experimental Irritant Contact Dermatitis." Contact Dermatol., 1995, 33:217-225.
Elias and Ghadially, "The aged epidermal permeability barrier," Clinical Geriatric Medicine, Feb. 2002, 103-120.
Ellis et al., "The Treatment of Psoriasis with Liquor Carbonis Detergens," J. Invest Dermatology, 1948, 10:455-459.
Emulsifiers With HLB Values, The Herbarie, retrieved on Aug. 5, 2009, http://www.theherbarie.com/files/resources-center/formulating/Emulsifiers-.sub.--HLB.sub.--Values.pdf, 3 pages.
Esposito et al., "Nanosystems for Skin Hydration: A Comparative Study," International Journal of Cosmetic Science, 2007, 29: 39-47.
Established ("Approved") Excipients, Encyclopedia of Pharmaceutical Technology, Second Edition, © 2002, vol. 3, 2146-2147.
Ethylene Oxide Derivatives: An Essence of Every Industry, retrieved on Jul. 12, 2011, http://www.emulsifiers.in/ethylene_oxide_derivatives2.htm, 3 pages.
European Patent Application No. 03772600.7 (Patent No. 1556009): Communication of a Notice of Opposition, dated Sep. 23, 2015, 42 pages.
European Patent Application No. 03772600.7 (Patent No. 1556009): Communication of a Notice of Opposition. dated Sep. 24, 2015, 30 pages.
European Patent Application No. 03772600.7 (Patent No. 1556009): Reply of the Patent Proprietor to the Notices of Opposition, dated May 9, 2016, 134 pages.
European Patent Application No. 03772600.7 (Patent No. 1556009): Summons to Attend Oral Proceedings, dated Jun. 30, 2016, 19 pages.
European Patent Application No. 03772600.7 (Patent No. 1556009): Interlocutory Decision in Opposition Proceedings, dated Feb. 3, 2017, 54 pages.
European Patent Application No. 03772600.7 (Patent No. 1556009): Minutes of Oral Proceedings, dated Feb. 3, 2017, 6 pages.
Excessive Sweating, Merck Manual Home Edition, Oct. 2007, retrieved on Apr. 14, 2011, www.merckmanuals.com/home/print/sec18/ch206/ch206c.html, 2 pages.
Fantin et al., "Critical influence of resistance to streptogramin B-type antibiotics on activity of RP 59500 (Quinupristin-dalfopristin) in experimental endocarditis due to *Staphylococcus aureus*," Antimicrob Agents and Chemothery, Feb. 1995, 39:400-405.
Farahmand et al., "Formulation and Evaluation of a Vitamin C Multiple Emulsion", Pharmaceutical Development and Technology, May 2006, 11(2):255-261 (English Abstract).
Flick, Cosmetic and Toiletry Formulations, 2nd Edition, Copyright 1996, vol. 5, 251-309.
Floyd, "Silicone Surfactants: Applicants in the Personal Care Industry," Silicone Surfactants, 1999, Chapter 7, 181-207.
Fluhr et al., "Glycerol accelerates recovery of barrier function in vivo," Acta Derm. Venereol, 1999, 79:418-421.
Foamix Pharmaceuticals Ltd. (May 1, 2017) "Foamix Pharmaceuticals Announces Plans for Additional Phase 3 Trial for FMX101 in Moderate to Severe Acne," Press Release [online]. Retrieved from: http://www.foamix.co.il/news.asp?nodeID=564&itemID=204, on Jun. 12, 2017, 5 pages.
Foamix Pharmaceuticals, Statement: Use of Luviquat FC 370, Approved by Yohan Hazot, May 3, 2016, 3 pages.

(56) References Cited

OTHER PUBLICATIONS

Fontana, "Water Activity: Why It is Important for Food Safety," International Conference on Food Safety, Nov. 16-18, 1998, 177-185.
Fontana (Apr. 1999) "Pharmaceutical Applications for Water Activity" *Pharmaceutical Online* [online]. Retrieved from https://www.pharmaceuticalonline.com/doc/pharmaceutical-applications-for-water-activit- . . . , on Jan. 17, 2018 (4 pages).
Frankel, A.J. et al. (2010) "Coal Tar 2% Foam in Combination with a Superpotent Corticosteroid Foam for Plaque Psoriasis. Case Report and Clinical Implications" *J Clin Aesthet Dermatol*, 3(10):42-45.
Fully-Refined Paraffin Wax (FRP Wax), Industrial Raw Materials LLC, Feb. 21, 2008, retrieved on Aug. 22, 2013, <http://irmwax.com/Wax/Paraffin/fully_refined.asp> 1 page.
Gallarate et al., "On the Stability of Ascorbic Acid in Emulsified Systems for Topical and Cosmetic Use", International Journal of Pharmaceutics, 1999, 188:233-241.
Galligan et al., "Adhesive Polyurethane Liners for Anterior Restorations," J. Dent. Res., Jul.-Aug. 1968, 629-632.
Garti et al. "Sucrose Esters microemulsions," J. Molec. Liquids, 1999, 80:253-296.
Gas Gangrene, Merck Manual Home Edition, 2008, retrieved on Jan. 16, 2013, <http://www.merckmanuals.com/home/infections/bacterial_infections/gas_gangrene.html?qt=gasgangrene&alt=sh>1 page.
Gelbard et al. "Primary Pediatric Hyperhidrosis: A Review of Current Treatment Options," Pediatric Dermatology, 2008, 25(6):591-598.
Gels, UNC: The Pharmaceutics and Compounding Laboratory, retrieved on Aug. 25, 2014, http://pharmlabs.unc.edu/labs/gels/agents/htm, 4 pages.
Ghica, M.V. et al. (2011) "Design and optimization of some collagen-minocycline based hydrogels potentially applicable for the treatment of cutaneous wound infections" *Pharmazie*, 66:853-861.
Gill et al., "Adverse Drug Reactions in a Paediatric Intensive Care Unit," Acta Paediatric, 1995, 84:438-441.
Gladkikh, "Ascorbic Acid and Methods of Increasing its Stability in Drugs", Translated from Khimiko-Farmatsevticheskii Zhurnal, 1970, 4(12):37-42.
Glaser and Ballard, "Hyperhidrosis: A Comprehensive and Practical Approach to Patient Management," Expert Rev. Dermatol., Oct. 2006, 1(6):773-775.
Google Search Strategy for Minocycline Solubility, retrieved on Aug. 15, 2013, <http://www.googl.com/search?rls=com.microsoft%3Aen-us%3AIE-SearchBox&q-melocycline+solubility>, 1 page.
Graves et al., "Structure of Concentrated Nanoemulsions," The Journal of Chemical Physics, Apr. 1, 2005, 122:134703, 6 pages.
Griffin, "Calculation of HLB Values of Non-Ionic Surfactants," Journal of the Society of Cosmetic Chemists, May 14, 1954, 249-256.
Groveman et al., "Lack of Efficacy of Polysorbate 60 in the Treatment of Male Pattern Baldness", Arch Intern Med, 1985, 145:1454-1458.
Gschnait et al., "Topical Indomethacin Protects from UVB and UVA Irradiation," Arch. Dermatol. Res., 1984, 276:131-132.
Hakan et al., "The protective effect of fish oil enema in acetic acid and ethanol induced colitis," The Turkish Journal of Gastroenterology, 2000, 11(2):155-161.
Hall, "Diaper Area Hemangiomas: A Unique Set of Concerns," retrieved on Dec. 1, 2008, http://members.tripod.com/.about.Michelle.sub.--G/diaper.html, 8 pages.
Hallstar® GMS SE/AS, retrieved on Jun. 4, 2011, http://www.hallstar.com/pis.php?product=1H022, 1 page.
Hammer et al., "Anti-Microbial Activity of Essential Oils and other Plant extracts," J. Applied Microbiology, 1999, 86:985-990.
Hanasono et al., "The Effect of Silicone Gel on Basic Fibroblast Growth Factor Levels in Fibroblast Cell Culture", Arch Facial Plast Surg, vol. 6, pp. 88-23 (2004).
Handbook of Pharmaceutical Excipients 79, 85, 215, 336, 386, 443, 568, 599 (Arthur H. Kibbe ed., 2000).
Hargreaves, "Chemical Formulation, An Overview of Surfactant-Based Preparations Used in Everyday Life", The Royal Society of Chemistry, 2003, 114-115.
Harrison et al., "Effects of cytokines and R-837, a cytokine inducer, on UV-irradiation augmented recurrent genital herpes in guinea pigs", Antiviral Res., 1991, 15(4):315-322.
Harrison et al., "Modification of Immunological Responses and Clinical Disease During Topical R-837 Treatment of Genital HSV-2 Infection," Antiviral Research, 1988, 10:209-224.
Harrison et al., "Pharmacokinetics and Safety of Imiquimod 5% Cream in the Treatment of Actinic Keratoses of the Face, Scalp, or Hands and Arms", Arch. Dermatol. Res., Jun. 2004, 296(1):6-11 (English Abstract).
Harrison et al., "Posttherapy Suppression of Genital Herpes Simplex Virus (HSV) Recurrences and Enhancement of HSV-Specific T-Cell Memory by Imiquimod in Guinea Pigs", Antimicrobial Agents and Chemotherapy, Sep. 1994, 38(9):2059-2064.
Harry, "Skin Penetration," The British Journal of Dermatology and Syphilis, 1941, 53:65-82.
Hashim et al., "Tinea versicolor and visceral leishmaniasis," Int J Dermatol., Apr. 1994; 33(4):258-259 (Abstract).
haute.de, "Substance (INCI-Designation): Triethanolamine" [online]. Retrieved on Sep. 14, 2015, http://www.haut.de/service/inci/anzeige&id=I6384&query=Triethanolamine&funktio . . . ; German with English translation, 3 pages.
Haw, "The HLB System: A Time Saving Guide to Surfactant Selection," Presentation to the Midwest Chapter of the Society of Cosmetic Chemists, Mar. 9, 2004, 39 pages.
Healy et al., "Acne vulgaris", Br. Med. J., 308: 831-833, 831 (1994).
Healy, "Gelled Emollient Systems for Controlled Fragrance Release and Enhanced Product Performance," Cosmetics and toiletries, 2002, 117(2): 47-54.
Heart Failure, The Merck Manual, 2008, retrieved Oct. 9, 2010, http://www.merck.com/mmhe/sec03/ch025/ch025a.html, 12 pages.
Helmenstine, "Surfactant Definition—Chemistry Glossary Definition of Surfactant," About.com Chemistry, retrieved on Mar. 5, 2012, http://chemistry.about.com/od/chemistryglossary/g/surfactant.htm, 1 page.
Hepburn, "Cutaneous leishmaniasis," Clin Exp Dermatol, Jul. 2000, 25(5):363-370 (Abstract).
HLB Systems, Pharmcal.tripod.com, retrieved on Sep. 17, 2010, http://pharmcal.tripod.com/ch17.htm, 3 pages.
HLB-Numbers, Sigma Aldrich, 2009, retrieved on Feb. 2, 2009, http://www.sigmaaldrich.com/materials-science/micro-and-nanoelectronics/l- ithography-nanopatterning/hlb-numbers.html, 3 pages.
How to Have a Healthy Libido in Mid-life and Beyond, GreenWillowTree.com, Jan. 2001, retrieved on Jul. 28, 2012, http://www.greenwillowtree.com/Page.bok?file=libido.html, 5 pages.
Hubbe, Colloidal Silica, Mini-Encyclopedia of Papermaking Wet-End Chemistry: Additives and Ingredients, their Composition, Functions, Strategies for Use, Feb. 1, 2001, retrieved on Jun. 4, 2011, http://www4.ncsu.edu/~hubbe/CSIL.htm, 2 pages.
Human Immunodeficiency Virus Infection, Merck Manual Home Edition, 2008, retrieved on Jan. 16, 2013, <http://www.merckmanuals.com/home/infections/human_immunodeficiency_virus_hiv_infection/human_immunodeficiency_virus_infection.html?qt=human immunodeficiency virus infection&alt=sh >, 11 pages.
Hwang et al., "Isolation and identification of mosquito repellents in *Artemisia vulgaris*," J. Chem. Ecol., 1985, 11: 1297-1306.
ICI Americas Inc., "Meaning of HLB Advantages and Limitations" Chapter 1 in *The HLB System. A Time-Saving Guide to Emulsifier Selection*. Wilmington, Delaware: 1980; pp. 1-4.
Ikuta et al., "Scanning Electron Microscopic Observation of Oil/Wax/Water/Surfactant System", Journal of SCCJ, 2004, 34(4):280-291 (English Abstract).
Indomethacin, Aug. 15, 2009, retrived on Jun. 3, 2011, http://it03.net/com/oxymatrine/down/1249534834.pdf, 3 pages.
Innocenzi et al., "An Open-Label Tolerability and Effacy Study of an Aluminum Sesquichlorhydrate Topical Foam in Axillary and Palmar Primary Hyperhidrosis," Dermatologic Therapy, 2008, 21:S27-S30.

(56) References Cited

OTHER PUBLICATIONS

Izquierdo et al. "Formation and Stability of Nano-Emulsions Prepared Using the Phase Inversion Temperature Method," Langmuir, 2002, 18(1):26-30 (Abstract).
Jan, "Troubled Times: Detergent Foam," retrieved on Feb. 9, 2012, http://zetatalk.com/health/theal17c.htm, 2 pages.
Johns Hopkins on Acne https://www.hopkinsmedicine.org/health/conditions-and-diseases/acne, 6 pages, 2019.
Joseph, "Understanding foams & foaming," University of Minnesota, May 1997, http://www.aem.umn.edu/people/faculty/joseph/archive/docs/understandingfoams.pdf, 8 pages.
Kalkan et al., "The Measurement of Sweat Intensity Using a New Technique," Tr. J. of Medical Sciences, 1998, 28:515-517.
Kanamoto et al., "Pharmacokinetics of two rectal dosage forms of ketoprofen in patients after anal surgery," J Pharmacobiodyn., Mar. 1988, 11(3):141-145.
Kang et al., "Enhancement of the Stability and Skin Penetration of Vitamin C by Polyphenol", Immune Netw., Dec. 2004, 4(4):250-254 (English Abstract).
Kanicky, J.R. and D.O. Shah (2002) "Effect of Degree, Type, and Position of Unsaturation on the $pK_a$ of Long-Chain Fatty Acids" *J Colloid and Interface Science*, 256:201-207.
Karasu et al., "Practice Guideline for the Treatment of Patients with Major Depressive Disorder," Second Edition, Apr. 2000, 78 pages.
Kanwar et al., "Treatment of Melasma with Potent Topical Corticosteroids", Dermatology, 188(2):170 (1994). 188(2):170.
Kathon™ CG, Rohm and Haas Personal Care, Jun. 2006, 9 pages.
Kaur et al., "Formulation Development of Self Nanoemulsifying Drug Delivery System (SNEDDS) of Celecoxib for Improvement of Oral Bioavailability," Pharmacophore, 2013, 4(4):120-133.
Kim, "Stability of Minoxidil in Aqueous Solution", Yakhak Hoechi, 1986, 30(5):228-231 (English Abstract).
Kinnunen and Hannuksela, "Skin reactions to hexylene glycol," Contact Dermatitis, Sep. 1989, 21(3):154-158.
Kircik, L.H. and S. Kumar (Aug. 2010) "Scalp Psoriasis" *J Drugs Dermatol*, 9(8 Suppl):s101-s137.
Kircik et al., "Formulation and Profile of FMX101 4% Minocycline Topical Foam for the Treatment of Acne Vulgaris," J. Clin. Aesthet. Dermatol., 13(4): 14-21 (2020).
Kleber et al., "Practice Guideline for the Treatment of Patients with Substance Use Disorders," Aug. 2006, 276 pages.
Klucel Hydroxypropylcellulose; Chemical and Physical Properties, Hercules Limited, copyright 1986, retrieved on Aug. 25, 2014, http://legacy.library.ucsf.edu/tid/cnf81a99/pdf, 35 pages.
Knight et al., "Topical diltiazem ointment in the treatment of chronic anal fissure," Br. J. Surg., 2001, 88(4):553-556.
Koerber, "Humectants and Water Activity," Water Activity News, 2000, 8 pages.
Kolb, "Emulsifiers, emollients and solubilizers for personal care", pp. 1-9, accessed Jun. 20, 2018.
Kreuter, "Nanoparticles and microparticles for drug and vaccine delivery," J. Anat., 1996, 189:503-505.
Kucharekova et al., "Effect of a lipid-rich emollient containing ceramide 3 in experimentally induced skin barrier dysfunction," Contact Dermatitis, Jun. 2002, 46:331-338.
Kumar et al., "Application of Broad Spectrum Antiseptic Povidone Iodine as Powerful Action: A Review," Journal of Pharmaceutical Science and Technology, 2009, 1(2):48-58.
Kwak et al. "Study of Complete Transparent Nano-Emulsions which Contain Oils." IFSCC Conference, Seoul Korea, Sep. 2003, 3 pages.
Laboratory 6—Characteristics of Surfactants and Emulsions, retrieved on Jan. 29, 2010, http://web.archive.org/web/20000106225413/http://pharmacy.wilkes.edu/kibbeweb/lab7.html, 5 pages.
Lautenschlager, "A Closer Look on Natural Agents: Facts and Future Aspects," Kosmetic Konzept Kosmetische Praxis, 2006, 5:8-10.
Le Vine et al., "Components of the Goeckerman Regimen," Journal of Investigative Dermatology, 1979, 73:170-173.

Lebwohl and Ali, "Treatment of psoriasis. Part 1. Topical therapy and phototherapy," J. Am Acad Dermatol, Oct. 2001, 487-498.
Lebwohl et al., "A randomized, double-blind, placebo-controlled study of clobestasol propionate 0.05% foam in the treatment of nonscalp psoriasis," International Journal of Dermatology, 2002, 41(5): 269-274.
Lee et al., "Historical review of melanoma treatment and outcomes," Clinics in Dermatology, 2013, 31: 141-147.
Lee et al., "The Stabilization of L-Ascorbic Acid in Aqueous Solution and Water-in-Oil-in-Water Double Emulsion by Controlling pH and Electrolyte Concentration," J. Cosmet. Sci., Jan./Feb. 2004, 55:1-12.
Leive et al., "Tetracyclines of various hydrophobicities as a probe for permeability of *Escherichia coli* outer membrane," Antimicrobial Agents and Chemotherapy, 1984, 25:539-544.
Leunapon-F, Leuna-Tenside, Screenshot, retrieved on Sep. 18, 2015, http://www.leuna-tenside.de/2006_7_14_3143/2006_8_7 5750/2006_8_7 241/cas-68439-49-6, 1 page.
Leung and Robinson, "Bioadhesive Drug Delivery," American Chemical Society, 1991, Chapter 23, 350-366.
Li et al., "Solubility Behavior of Imiquimod in Alkanoic Acids", Pharmaceutical Research, Abstract 3029, Nov. 1997,14(11):S475, 2 pages.
Licking Vaginal Dryness Without a Prescription, retrieved on Dec. 14, 2008, http://www.estronaut.com/a/vag.sub.--dryness.htm, 3 pages.
Lin et al., "Ferulic acid stabilizes a solution of vitamins c and e and doubles its photoprotection of skin," J Invest Dermatol, 2005, 125:826-832.
Lippacher et al., "Liquid and Semisolid SLN Dispersions for Topical Application: Rheological Characterization," European Journal of Pharmaceutics and Biopharmaceutics, 2004, 58:561-567.
Livingstone and Hubel, "Segregation of form, color, movement, and depth: Anatomy, physiology, and perception," Science, May 1988, 240:740-749.
Lupke and Kemper, "The HET-CAM Test: An Alternative to the Draize Eye Test," FD Chem. Toxic., 1986, 24:495-196.
Lupo, "Antioxidants and Vitamins in Cosmetics", Clinics in Dermatology, 2001, 19:467-473.
Luviquat Polymer Grades, BASF The Chemical Company, May 2012, 32 pages.
Mah et al., "Irrational Use of Skin-Bleaching Products Can Delay the Diagnosis of Leprosy", International Journal of Leprosy and Other Mycobacterial Diseases, vol. 70, No. 2, pp. 119-121 (2002).
Mailer, "Chemistry and quality of olive oil," NSW Dept. of Primary Industries, Aug. 2006, Primefact 227, 1-4.
Martindale: The Complete Drug Reference, 33rd Edition, Jun. 2002, Pharmaceutical Press, pp. 1073 and 1473.
Martindale: The Complete Drug Reference, Thirty-third edition, Bath Press, London, 2002, 1073 and 1473.
Martindale: The Extra Pharmacopoeia, Twenty-eighth edition, The Pharmaceutical Press, London, 1982, 862-864.
Material Safety Data Sheet, Luvitol EHO, Caelo, Nov. 28, 2013, 4 pages.
Material Safety Data Sheet, Butane, Gas Innovations, Sep. 7, 2007, 3 pages.
Material Safety Data Sheet, Carbon Dioxide, Airgas, Feb. 11, 2016, 11 pages.
Material Safety Data Sheet, Dimethyl Ether, Airgas, May 14, 2015, 12 pages.
Material Safety Data Sheet, Hydroxyethyl Cellulose, Sigma-Aldrich, Jan. 14, 2004, http://terpconnect.umd.edu/-choi/MSDS/Sigma-Aldrich/HYDROXYETHYL%20CELLULOSE, 5 pages.
Material Safety Data Sheet, Hydroxyethyl Cellulose, Sigma-Aldrich, Jan. 2004, 5 pages.
Material Safety Data Sheet, Liquor carbonis detergens, Caelo, Nov. 28, 2013, 5 pages.
Material Safety Data Sheet, Mineral Oil, Macron Fine Chemicals, Oct. 24, 2011, 6 pages.
Material Safety Data Sheet, N-Butane, Airgas, May 7, 2015, 13 pages.
Material Safety Data Sheet, Nitrous Oxide, Airgas, Feb. 11, 2016, 11 pages.

(56) References Cited

OTHER PUBLICATIONS

Material Safety Data Sheet, Propane, Airgas, Oct. 20, 2015, 12 pages.
Material Safety Data Sheet, Science Lab.com, Polyethylene Glycol 200, MSDS, Nov. 6, 2008, 6 pages.
Material Safety Data Sheet, USP, Progesterone, Apr. 26, 2006, 5 pages.
McKetta, Encyclopedia of Chemical Processing and Design: vol. 2—Additives to Alpha, 1st Ed., pp. 214-238 (1977).
Mead, "Electrostatic Mechanisms Underlie Neomycin Block of the Cardiac Ryanodine Receptor Channel (RyR2)," Biophysical Journal, 2004, (87): 3814-3825.
The Merck Index: An Encyclopedia of Chemicals, Drugs, and Biologicals 1299-1300, 1638 (13th ed., 2001).
Messenger et al., "Minoxidil: Mechanisms of Action on Hair Growth", British Journal of Dermatology, 2004, 150:186-194.
Metronidazole (Veterinary—Systemic), The United States Pharmacopeial Convention, 2007, retrieved on Sep. 10, 2009, www.usp.org/pdf/EN/veterinary/metronidazole.pdf, 4 pages.
Metz et al., "A Phase I Study of Topical Tempol for the Prevention of Alopecia Induced by Whole Brain Radiotherapy," Clinical Cancer Research, Oct. 2004, 10:6411-6417.
Meucci et al., "Ascorbic Acid Stability in Aqueous Solutions", Acta Vitaminol Enzymol, 1985, 7(3-4):147-153 (English Abstact).
Milton, D.T. et al. (2006) "A Phase I/II Study of Weekly High-Dose Erlotinib in Previously Treated Patients With Nonsmall Cell Lung Cancer" *Cancer*, 107:1034-1041.
Mineral Oil USP, U.S. Department of Health & Human Services, Chemical Abstracts Service Registry No. 8012-95-1, 2011, 7 pages.
Minocycline (DB01017), Drug Bank, Feb. 8, 2013, retrieved on Aug. 15, 2013, <http://www.drugbank.ca/drugs/DB01017>, 10 pages.
Minocycline, Wikipedia, the free encyclopedia, retrieved on Oct. 21, 2011, http://en.wikipedia.org/wiki/Minocycline, 7 pages.
MMP Inc., International Development and Manufacturing, "Formulating specialties," retrieved on Feb. 2, 2010, http://mmpinc.com, 3 pages.
Molan, "World Wide Wounds: Honey as a topical antibacterial agent for treatment of infected wounds," Dec. 2001, retrieved May 7, 2008, http://www.worldwidewounds.com/2001/november/Molan/honey-as-topical-agent.html, 13 pages.
*Molins PLC* v. *Textron Inc.*, 48 F.3d 1172, 33 USPQ2d 1823 (Fed. Cir. 1995), 19 pages.
Morgan et al., "Enhanced Skin Permeation of Sex Hormones with Novel Topical Spray Vehicles," Journal of Pharmaceutical Sciences, Oct. 1998, 87(10):1213-1218.
Mousse, Merriam-Webster Online Dictionary, retrieved on Dec. 8, 2008, http://www.merriam-webster.com/dictionary/mousse, 2 pages.
Musial, W. and A. Kubis (2004) "Carbopols as factors buffering triethanolamine interacting with artificial skin sebum" *Polim Med*, 34(4):17-30 (Abstract).
Natural Skincare Authority, "Disodium EDTA: Cosmetic Toxin Data," 2011, retrieved on Nov. 17, 2013, http://www.natural-skincare-authority.com/DISODIUM-EDTA.html, 4 pages.
Neutrogena Clinical SPF 30 Facial Lifting Wrinkle Treatment, Apr. 28, 2010, retrieved on Sep. 11, 2010, http://www.cosmetoscope.com/2010/04/neutrogea-clinical-with-johnson-johnsons-cytomimic-techology/, 5 pages.
Neves et al., "Rheological Properties of Vaginal Hydrophilic Polymer Gels," *Current Drug Delivery*, 2009, 6:83-92.
New Nanomaterials to Deliver Anticancer Drugs to Cells Developed, Science Daily, Jun. 2007, retrieved on Oct. 14, 2013, <URL: http://www.sciencedaily.com/releases/2007/06/070607112931.htm>, 3 pages.
Nietz, "Molecular orientation at surfaces of solids," J. Phys. Chem., 1928, 32(2): 255-269.
Niram Chemicals, Chemical products—Cetostearyl Alcohol, Cetyl Alcohol, Stearyl Alcohol and Polyethylene Glycol Importer & Supplier, retrieved on Jul. 17, 2012, http://www.indiamart.com/niramchemicals/chemicals.html, 7 pages.
Novartis "Lamisil®" Product Information, T2001-29 [online]. Retrieved from: http://www.fda.gov/downloads/Drugs/DrugSafety/PostmarketDrugSafetyInformationforPatientsandProviders/ucm052213.pdf; Published: Apr. 2001, 8 pages.
O'Neil, The Merck Index an Encyclopedia of Chemicals, Drugs, and Biologicals, p. 153 (2006).
Oh et al., "Antimicrobial activity of ethanol, glycerol monolaurate or lactic acid against *Listeria moncylogenes*," Int. J. Food Microbiology, 1993, 20:239-246.
Olsen et al., "A Multicenter, Randomized, Placebo-Controlled, Double-Blind Clinical Trial of a Novel Formulation of 5% Minoxidil Topical Foam Versus Placebo in the Treatment of Androgenetic Alopecia in Men", J. Am. Acad Dermatol, Nov. 2007, 57:767-774.
Olux Prescribing Information (2013).
OM-Cinnamate, MakingCosmetics.com, retrieved on Sep. 26, 2009, http://www.makingcosmetics.com/sunscreens/OM-Cinnamate-p102.html, 1 page.
Omega-9 Fatty Acids (Oleic Acid), Orthomolecular.org, Dec. 2004, retrieved on Aug. 15, 2014, http://orthomolecular.org/nutrients/omega9.html, 1 page.
Optimization of Nano-Emulsions Production by Microfluidization, European Food Research and Technology. Sep. 2007, 22:5-6 (English Abstract).
Oranje et al., "Topical retapamulin ointment, 1%, versus sodium fusidate ointment, 2%, for impetigo: a randomized, observer-blinded, noninferiority study," Dermatology, 2007, 215(4):331-340.
Osborne and Henke, "Skin Penetration Enhancers Cited in the Technical Literature," Pharm. Technology, Nov. 1997, 21(11):58-86.
Padhi et al., "Phospho-olivines as positive-electrode materials for rechargeable lithium batteries," J. Electrochemical Soc., Apr. 1997, 144(4): 1188-1194.
Padi and Kulkarni, "Minocycline prevents the development of neuropathic pain, but not acute pain: possible anti-inflammatory and antioxidant mechanisms," Eur J. Pharmacol, 2008, 601:79-87.
Pakpayat et al., "Formulation of Ascorbic Acid Microemulsions with Alkyl Polyglycosides", European Journal of Pharmaceutics and Biopharmaceutics, 2009, 72:444-452.
Palamaras and Kyriakis, "Calcium antagonists in dermatology: a review of the evidence and research-based studies," Derm. Online Journal, 2005, 11(2):8.
Pantaris et al., "The lauric (coconut and palmkernal) oils", Vegetable Oils in Food Technology, Chemistry and Technology of Oils and Fats, pp. 157-202 (2002).
Passi et al., "Lipophilic antioxidants in human sebum and aging," Free Radical Research, 2002,36(4):471-477.
Pharmaceutical Benefits Advisory Committee (PBAC) of Australia. PBAC Public Summary Document—Nov. 2014 Meeting (5 pages).
Pendergrass et al., "The shape and dimension of the human vagina as seen in three-dimensional vinyl polysiloxane casts," Gynecol Obstet. Invest., 1996, 42(3):178-82 (Abstract).
Penreco, "Intelligent Gel Technology Product Specifications," Rev. Jun. 2016 (2 pages).
Permethrin (Insecticide), Wildpro, retrieved on Jun. 4, 2015, http://wildpro.twycrosszoo.org/S/00Chem/ChComplex/perm.htm, 5 pages.
Perotti et al., "Topical Nifedipine With Lidocaine Ointment vs. Active Control for Treatment of Chronic Anal Fissure," Dis Colon Rectum, 2002, 45(11):1468-1475.
Polystyrene, Wikipedia the free encyclopedia, retrieved Apr. 21, 2014, http://web.archive.org/web/20060312210423/http://en.wikipedia.org/wiki/Polystyrene, 4 pages.
PPG-40-PEG-60 Lanolin Oil, Environmental Working Group, 2010, retrieved on May 19, 2010, http://www.cosmeticsdatabase.com/ingredient/722972/PPG-40-PEG-60_Lanolin_Oil/?ingred06=722972., 3 pages.
Prevent, The American Heritage Dictionary of the English Language, 2007, retrieved on Oct. 9, 2010, http://www.credoreference.com/entry/hmdictenglang/prevent, 1 page.
Product Data Sheet for Meclocycline, bioaustralis fine chemicals, Jun. 28, 2013, 1 page.
Promius™ Pharma LLC (2012) Scytera™ (coal tar) Foam, 2%. Product Information Sheet, 1 page.

(56) References Cited

OTHER PUBLICATIONS

Prud'Homme et al., Foams: theory, measurements and applications, Marcel Dekker, Inc., 1996, 327-328.
Purcell, "Natural Jojoba Oil Versus Dryness and Free Radicals," Cosmetics and Toiletries Manufacture Worldwide, 1988, 4 pages.
Purdy et al., "Transfusion-transmitted malaria: unpreventable by current donor exclusion guidelines?" Transfusion, Mar. 2004, 44:464.
Raschke et al., "Topical Activity of Ascorbic Acid: From In Vitro Optimization to In Vivo Efficacy", Skin Pharmacology and Physiology, Jul./Aug. 2004, 17(4):200-206 (Abstract).
Ravet et al., "Electroactivity of natural and sythetic triphylite," J. Power Sources, 2001, 97-98: 503-507.
Raymond, "Iodine as an Aerial Disinfectant," J. Hygiene, May 1946, 44(5):359-361.
Reaction Rate, Wikipedia, the free encyclopedia, retrieved on Dec. 18, 2011, en.wikipedia.org/wiki/Reaction_rate, 6 pages.
Receptacle, Merriam Webster, retrieved on Jul. 12, 2011, http://www.merriam-webster.com/dictionary/receptacle, 1 page.
Refina, "Viscosity Guide for Paints, Petroleum & Food Products," accessed Mar. 4, 2015, http://www.refina.co.uk/webpdfs/info_docs/Viscosity_guide_chart.pdf, 2 pages.
Regulation (EC) No. 2003/2003 of the European Parliament and of the Council, Official Journal of the European Union, Oct. 13, 2003, 2 pages.
Repa et al. "All-trans-retinol is a ligand for the retinoic acid receptors," Proc. Natl. Acad Sci, USA, Aug. 1993, 90: 7293-7297.
Reregistration Eligibility Decision for Pyrethrins, EPA, Jun. 7, 2006, 108 pages.
Richwald, "Imiquimod", Drugs Today, 1999, 35(7):497 (Abstract).
Rieger and Rhien, "Emulsifier Selection/HLB," Surfactants in Cosmetics, 129, 1997.
Rohstoffinformationen, Hoffmann Mineral, 2008, 8 pages (with English translation).
Rosacea, Clinuvel Pharmaceuticals, 2010, retrieved on Sep. 9, 2010, http://clinuvel.com/skin-conditions/common-skin-conditions/rosacea#h0-6-prevention, 5 pages.
Rowe et al., "Glyceryl Monooleate," Handbook of Pharmaceutical Excipients, 2011, 10 pages, retrieved on Dec. 19, 2011, http://www.medicinescomplete.com/mc/excipients/current/1001938996.htm?q=glyceryl%20monooleate&t=search&ss=text&p=1# hit.
Rowe et al., "Octyldodecanol," Handbook of Pharmaceutical Excipients, 2011, 9 pages, retrieved on Dec. 19, 2011, URL:http://www.medicinescomplete.com/mc/excipients/current/1001942450.htm?q=octyldodecanol&t=search&ss=text&p=1# hit.
Rowe et al., "Sucrose Palmitate," Handbook of Pharmaceutical Excipients, 2011, 11 pages, retrieved on Dec. 19, 2011, URL:http://www.medicinescomplete.com/mc/excipients/current/EXP-TD-c46-mn0001.htm?q=sucrose%20stearate&t=search&ss=text&p=1# hit.
Rowe et al., "Sucrose Stearate," Handbook of Pharmaceutical Excipients, 2011, 11 pages, retrieved on Dec. 19, 2011, URL:http://www.medicinescomplete.com/mc/excipients/current/EXP-TD-cll-mnOOOI-mnOOOI.htm?q=sucrose%20stearate&t=search&ss=text&p=3# hit.
RSES (Oil in Refrigerator Systems, Service Application Manual, 2009).
Rutledge, "Some corrections to the record on insect repellents and attractants," J. Am. Mosquito Control Assoc, Dec. 1988, 4(4): 414-425.
Sakai et al., "Characterization of the physical properties of the stratum corneum by a new tactile sensor," Skin Research and Technology, Aug. 2000, 6:128-134.
Sanders et al., "Stabilization of Aerosol Emulsions and Foams," J. Soc. Cosmet. Chem., 1970, 21:377-391.
Sarkar et al., "A Comparative Study of 20% Azelaic Acid Cream Monotherapy versus a Sequential Therapy in the Treatment of Melasma in Dark-Skinned Patients", Dermatology, 205(3): 249-54 (2002).
Sarpotdar, P.P. et al. (Jan. 1986) "Effect of Polyethylene Glycol 400 on the Penetration of Drugs Through Human Cadaver Skin In Vitro" *J Pharma Sci*, 75(1):26-28.

Savin et al., "Tinea versicolor treated with terbinafine 1% solution," Int J. Dermatol, Nov. 1999; 38(11): 863-865.
Schaefer, "Silicone Surfactants," Tenside Surf. Det., 1990, 27(3): 154-158.
Schmidt, "Malassezia furfur: a fungus belonging to the physiological skin flora and its relevance in skin disorders," Cutis, Jan. 1997, 59(1):21-24 (Abstract).
Schmolka, "A review of block polymer surfactants," Journal of the American Oil Chemists Society, Mar. 1977, 54: 110-116.
Schott, "Rheology," Remington's Pharmaceutical Sciences, 17th Edition, 1985, 330-345.
Schutze, "Iodine and Sodium Hypochlorite as Wound Disinfectants," The British Medical Journal, 1915, 921-922.
Sciarra, "Aerosol Technology," *Kirk-Othmer Encyclopedia of Chemical Technology*, Jul. 2012, 20 pages.
Sciarra et al., "Aerosols", Remington: The Science and Practice of Pharmacy, pp. 963-966 (2000).
Scientific Discussion for the Approval of Aldara, EMEA, 2005, 10 pages.
Scott, "A Practical Guide to Equipment Selection and Operating Techniques," Pharmaceutical Dosage Forms: Disperse Systems, vol. 3, Copyright 1998, 291-362.
Scully et al., "Cancers of the oral mucosa treatment and management," Medscape Drugs, Diseases and Procedures, Apr. 20, 2012, retrieved on Oct. 12, 2013, <http://emedicine.medscape.com/article/1075729-treatment>, 10 pages.
Seborrheic Dermatitis, retrieved on Sep. 9, 2010, http://www.cumc.columbia.edu/student/health/pdf/R-S/Seborrhea%20Dermatitis.pdf, 2 pages.
Security Datasheet, Luvitol EHO, Cetearyloctanoat, Nov. 27, 2013, 10 pages.
Sehgal, "Ciclopirox: a new topical pyrodonium antimycotic agent: A double-blind study in superficial dermatomycoses," *British Journal of Dermatology*, 1976, 95:83-88.
Sharp, "Oil," Dictionary of Chemistry, Copyright 1990, 286.
Shear et al., "Pharmacoeconomic analysis of topical treatments for tinea infections," Pharmacoeconomics, Mar. 1995, 7(3):251-267.
Shear, Vocabulary.com, retrieved on Aug. 23, 2013, <URL: https://www.vocabulary.com/dictionary/shear>, 3 pages.
Sheer, Vocabulary.com, retrieved on Aug. 23, 2013, https://www.vocabulary.com/dictionary/sheer, 3 pages.
Shemer, A. et al. (2016) "Topical minocycline foam for moderate to severe acne vulgaris: Phase 2 randomized double-blind, vehicle-controlled study results" *J Am Acad Dermatol*, 74(6):1251-1252.
Sheu et al., "Effect of Tocopheryl Polyethylene Glycol Succinate on the Percutaneous Penetration of Minoxidil from Water/Ethanol/Polyethylene Glycol 400 Solutions," Drug Dev. Ind. Pharm., Jun. 2006, 32(5):595-607 (Abstract).
Shim et al., "Transdermal Delivery of Mixnoxidil with Block Copolymer Nanoparticles," J. Control Release, Jul. 2004, 97(3):477-484 (Abstract).
Shrestha et al., "Forming properties of monoglycerol fatty acid esters in nonpolar oil systems," *Langmuir*, 2006, 22: 8337-8345.
Sigma-Aldrich. http://www.sigmaaldrich.com/catalog/product/sial/p1754?lang=en® ion=. Published:Mar. 5, 2014.
Sigma Aldrich, "Surfactants Classified by HLB Numbers" 2017 [online]. Retrieved from the Internet: www.sigmaaldrich.com/materials-science/material-science-products.html?TablePage=22686648, on Jul. 8, 2017 (3 pages).
Silicone, Oxford Dictionaries Online, retrieved on Apr. 19, 2011, http://www.oxforddictionaries.com/definition/silicone?view=uk, 1 page.
Simoni et al., "Retinoic acid and analogs as potent inducers of differentiation and apoptosis. New promising chemopreventive and chemotherapeutic agents in oncology," Pure Appl Chem., 2001, 73(9):1437-1444.
Simovic et al., "The influence of Processing Variables on Performance of O/W Emulsion Gels Based on Polymeric Emulsifier (Pemulen® TR-2NF)," International Journal of Cosmetic Science, Dec. 2001, 21(2)119-125 (Abstract).
Smith, "Hydroxy acids and skin again," Soap Cosmetics Chemical Specialties, Sep. 1993, 69(9):54-59.

(56) References Cited

OTHER PUBLICATIONS

Smith, "Sore Nipples," Breastfeeding Mom's Sore Nipples / Breastfeeding Basics, retrieved on Feb. 8, 2012, http://breastfeedingbasics.com/articles/sore-nipples, 9 pages.
Softemul-165: Product Data Sheet, Mohini Organics PVT LTD, retrieved Apr. 10, 2014, http://www.mohiniorganics.com/Softemul165.html#, 1 page.
Solans et al., "Overview of basic aspects of microemulsions," Industrial Applications of Microemulsions, New York, 1997, 1-17.
Solodyn® (Minocycline HCl, USP) Prescribing Information; revised Jun. 2016, 2 pages.
Sonneville-Aubrun et al., "Nanoemulsions: A New Vehicle for Skincare Products," Advances in Colloid and Interface Science, 2004, 108-109:145-149.
Spa Collections, AG & Co. Essential oil workshop, retrieved on Jan. 31, 2010, http://www.agworkshop.com/p3.asp, 1 page.
Squillante et al., "Codiffusion of propylene glycol and dimethyl isosorbide in hairless mouse skin," European J. Pharm. Biopharm., 1998, 46:265-271.
Squire and Goode, "A randomized, single-blind, single-centre clinical trial to evaluate comparative clinical efficacy of shampoos containing ciclopirox olamine (1.5%) and salicylic acid (3%), or ketoconazole (2%, Nizoral) for the treatment of dandruff/seborrhoeic dermatitis," Dermatolog Treat., Jun. 2002, 13(2):51-60 (Abstract).
Sreenivasa et al., "Preparation and Evaluation of Minoxidil Gels for Topical Application in Alopecia," Indian Journal of Pharmaceutical Sciences, 2006, 68(4):432-436.
Sreenivasan, B. et al. (1956)"Studies on Castor Oil. I. Fatty Acid Composition of Castor Oil" *J Am Oil Chem Soc*, 33:61-66.
Stehle et al., "Uptake of minoxidil from a new foam formulation devoid of propylene glycol to hamster ear hair follicles," J. Invest. Dermatol., 2005, 124(4): A101 (Abstract).
Sugisaka et al., "The Physicochemical Properties of Imiquimod, the First Imidazoquinoline Immune Response Modifier", Pharmaceutical Research, Nov. 1997, 14(11):S475, Abstract 3030.
*Sun Pharmaceutical Industries Ltd.* v. *Eli Lilly and Co.*, 611 F.3d 1381, 95 USPQ2d 1797 (Fed. Cir. 2010),7 pages.
Sung, J.H. et al. (2010) "Gel characterisation and in vivo evaluation of minocycline-loaded wound dressing with enhanced wound healing using polyvinyl alcohol and chitosan" *Intl J Pharmaceut*, 392:232-240.
Surfactant, Wikipedia, the free encyclopedia, retrieved on Oct. 24, 2010, http://en.wikipedia.org/wiki/Surfactant, 7 pages.
Tadros, "Surfactants in Nano-Emulsions." Applied Surfactants: Principles and Applications, 2005, 285-308.
Tamarkin, D. (2013) "Foam: A Unique Delivery Vehicle for Topically Applied Formulations" in: *Formulating Topical Applications—a Practical Guide*. Dayan N, Ed., Carol Stream, IL: CT Books, Chapter 9, pp. 233-260.
Tan et al., "Effect of Carbopol and PolyvinYlpyrrolidone on the Mechanical, Rheological, and Release Properties of Bioadhesive Polyethylene Glycol Gels," AAPS PharmSciTech, 2000; 1(3) Article 24, 10 pages.
Tanhehco, "Potassium Channel Modulators as Anti-Inflammatory Agents", Expert Opinion on Therapeutic Patents, Jul. 2001, 11(7):1137-1145 (Abstract).
Tarumoto et al., "Studies on toxicity of hydrocortisone 17-butyrate 21-propionate-1. Acute toxicity of hydrocortisone 17-butyrate 21-propionate and its analogues in mice, rats and dogs (author's transl)," J Toxicol Sci., Jul. 1981, 6:1-16 (Abstract).
Tata et al., "Penetration of Minoxidil from Ethanol Propylene Glycol Solutions: Effect of Application Volume on Occlusion," Journal of Pharmaceutical Sciences, Jun. 1995, 84(6):688-691.
Tata et al., "Relative Influence of Ethanol and Propylene Glycol Cosolvents on Deposition of Minoxidil into the Skin," Journal of Pharmaceutical Sciences, Jul. 1994, 83(10):1508-1510.
Tavss et al., "Anionic detergent-induced skin irritation and anionic detergent-induced pH rise of bovine serum albumin," *J. Soc. Cosmet. Chem.*, Jul./Aug. 1988, 39:267-272.

TCI America, Safety Data Sheet; Product Name: Squalane. Product Code: H0096 [online]. Retrieved from: https://www.spectrumchemical.com/MSDS/TCI-H0096.pdf. Revised: Oct. 6, 2014, 5 pages.
Tea Tree Oil, LookChem, Chemical Abstract No. 68647-73-4, 2012, 2 pages.
Tenjarla, "Microemulsions: An Overview and Pharmaceutical Applications", Crit. Rev. Ther. Drug Carrier Sys., 16(5): 461-521 (1999).
The HLB System—A Time-Saving Guide to Emulsifier Selection, ICI Americas Inc., Mar. 1980, 1-22.
The United States Pharmacopeia: The National Formulary, USP23/NF18, US Pharmacopoeia, Jan. 1995, p. 10-14.
Third Party Submission in Published Patent Application, U.S. Appl. No. 12/014,088, Feb. 4, 2009, 4 pages.
Thorgeirsdottir et al., "Antimicrobial activity of monocaprin: a monoglyceride with potential use as a denture disinfectant," Acta Odontologica Scandinavica, Feb. 2006, 64:21-26 (Abstract only).
Tirumala et al., "Abstract: D28.00011: Enhanced order in thinfilms of Pluronic (A-B-A) and Brij (A-B) Block copolymers blended with poly (acrylic acid)," Session D28: Block Copolymer Thin Films, Mar. 13, 2006, 1 page, Abstract.
Tjulandin, S. et al. (2013) "Phase I, dose-finding study of AZD8931, an inhibitor of EGFR (erbB1), HER2 (erbB2) and HER3 (erbB3) signaling, in patients with advanced solid tumors" *Invest New Drugs*, 32(1):145-153.
Todd et al., "Volatile Silicone Fluids for Cosmetic Formulations," Cosmetics and Toiletries, Jan. 1976, 91:27-32.
Torma et al., "Biologic activities of retinoic acid and 3,4-Didehydroretinoic acid in human keratinocytes are similar and correlate with receptor affinities and transactivation properties," J. Invest. Dermatology, 1994, 102: 49-54.
Torres-Rodriguez, "New topical antifungal drugs," Arch Med Res., Winter 1993, 24(4): 371-375 (Abstract).
Toxicology and Carcinogenesis Studies of T-Butyl Alcohol (CAS No. 75-65-0) in F344/N Rats and B6C3F1 Mice (Drinking Water Studies), May 1995, retrieved on Dec. 9, 2008, http://ntp.niehs.nih.gob/?objectid-=0709F73D-A849-80CA-5FB784E866B576D1, 4 pages.
Trofatter, "Imiqimod in clinical practice", European Journal of Dermatology, Oct./Nov. 1998, 8(7 Supp.):17-19 (Abstract).
Tsai et al., "Drug and Vehicle Deposition from Topical Applications: Use of In Vitro Mass Balance Technique with Minoxidil Solutions", J. Pharm. Sci., Aug. 1992, 81(8):736-743 (Abstract).
Tsai et al., "Effect of Minoxidil Concentration on the Deposition of Drug and Vehicle into the Skin," International Journal of Pharmaceutics, 1993, 96(1-3):111-117 (Abstract).
Tsai et al., "Influence of Application Time and Formulation Reapplication on the Delivery of Minoxidil through Hairless Mouse Skin as Measured in Franz Diffusion Cells," Skin Pharmacol., 1994, 7:270-277.
Tyring, "Immune-Response Modifiers: A New Paradigm in the Treatment of Human Papillomavirus," Current Therapeutic Research, Sep. 2000, 61(9):584-596 (Abstract).
Tzen et al. "Surface Structure and Properties of Plant Seed Oil Bodies," Department of Botany and Plant Sciences, University of California, Riverside, California 92521, Apr. 15, 1992, 9 pages.
Tzen et al., "Lipids, proteins and structure of seed oil bodies from diverse species," Plant Physiol., 1993, 101:267-276.
U.S. Final Office Action for U.S. Appl. No. 11/430,437, Tamarkin et al., dated Dec. 16, 2008, 24 pages.
U.S. Office Action for U.S. Appl. No. 11/430,437, Tamarkin et al., dated May 9, 2008, 27 pages.
U.S. Office Action from U.S. Appl. No. 11/430,599, dated Jul. 28, 2008, 59 pages.
Uner et al., "Skin Moisturizing Effect and Skin Penetration of Ascorbyl Palmitate Entrapped in Solid Lipid Nanoparticles (SLN) and Nanostructured Lipid Carriers (NLC) Incorporated into Hydrogel," Pharmazie, 2005, 60:751-755.
United States Standards for Grades of Olive Oil and Olive-Pomace Oil, United States Dept. of Agriculture, Oct. 25, 2010, 21 pages.
Valenta, "Effects of Penetration Enhancers on the In-vitro Percutaneous Absorption of Progesterone," J. Pharm. Pharmacol., 1997, 49: 955-959.
Van Cutsem et al., "The anti-inflammatory effects of ketoconazole," J. Am. Acad. Dermatol., Aug. 1991, 25(2):257-261.

(56) References Cited

OTHER PUBLICATIONS

Van Slyke, "On the measurement of buffer values and on the relationship of buffer value to the dissociation constant of the buffer and the concentration and reaction of the buffer solution," J. Biol. Chem., 1922, 52:525-570.

Vera et al., "Scattering optics of Foam," Applied Optics, Aug. 20, 2001, 40(24):4210-4214.

Veron et al., "Stability of Minoxidil Topical Formulations", Ciencia Pharmaceutica, 1992, 2(6):411-414 (Abstract).

Versagel® M Series, Mineral Oil Moisturizing Gels. Product Bulletin, retrieved from https://archive.org/web/, as archived Oct. 15, 2006, 3 pages.

View of NCT01171326 on Dec. 7, 2010, ClinicalTrials.gov archive, Dec. 7, 2010, retrieved on Sep. 9, 2013, http://clinicaltrials.gov/archive/NCT01171326/2010_12_07, 4 pages.

View of NCT01362010 on Jun. 9, 2011, ClinicalTrials.gov archive, Jun. 9, 2011, retrieved on Sep. 9, 2013, < http://clinicaltrials.gov/archive/NCT01362010/2011_06_09>, 3 pages.

Walstra, "Principles of Foam Formation and Stability", Foams: Physics, Chemistry and Structure, pp. 1-15 (1989).

Wang and Chen, "Preparation and surface active properties of biodegradable dextrin derivative surfactants," Colloids and Surfaces A: Physicochemical and Engineering Aspects, 2006, 281(1-3):190-193.

Water Jel Technologies, "Material Safety Data Sheet for Neomycin Antibiotic Ointment," Dec. 1, 2004, 7 pages.

WebMD (2014) "Psoriasis Health Center" [online]. Retrieved Apr. 13, 2015; retrieved from the Internet: http://www.webmd.com/skin-problems-and-treatments/psoriasis/psoriasis-symptoms, 3 pages.

WebMD (2014) "Understanding Rosacea—the Basics" [online]. Retrieved Apr. 13, 2015; retrieved from the Internet: http://www.webmd.com/skin-problems-and-treatments/understanding-rosacea-basics (5 pages).

Weindl et al., "Hyaluronic acid in the treatment and prevention of skin diseases: molecular biological, pharmaceutical and clinical aspects," Skin Pharmacology and Physiology, 2004, 17: 207-213.

Wenninger et al., "International Cosmetic Ingredient Dictionary and Handbook," The Cosmetic, Toiletry, and Fragrance Association, Washington, DC., 1997, vol. 1, 4 pages.

Wermuth, "Similarity in drugs: reflections on analogue design," Drug Discovery Today, Apr. 2006, 11(7/8):348-354.

What Is CP Serum, Skin Biology, retrieved on Dec. 1, 2008, http://web.archive.org/web/20030810230608/http://www.skinbio.com/cpserum.- html, 21 pages.

What Is TSC?, Tuberous Sclerosis Alliance, Jan. 1, 2005, retrieved on Feb. 6, 2014, http://www.tsalliance.org.pages.aspx?content=2, 3 pages.

Williams et al., "Acne vulgaris," Lancet, 2012, 379:361-372.

Williams et al., "Scale up of an olive/water cream containing 40% diethylene glycol monoethyl ether," Dev. Ind. Pharm., 2000, 26(1):71-77.

Williams et al., "Urea analogues in propylene glycol as penetration enhancers in human skin," International Journal of Pharmaceutics, 1989, 36, 43-50.

Wormser et al., "Protective effect of povidone-iodine ointment against skin lesions induced by sulphur and nitrogen mustards and by non-mustard vesicants," Arch. Toxicol., 1997, 71, 165-170.

Wormser, "Early topical treatment with providone-iodine ointment reduces, and sometimes prevents, skin damage following heat stimulus," Letter to the Editor, Burns, 1998, 24:383.

Wrightson, W.R. et al. (1998) "Analysis of minocycline by high-performance liquid chromatography in tissue and serum" *J Chromatography B*, 706:358-361.

Wu et al., "Interaction of Fatty Acid Monolayers with Cobalt Nanoparticles," Nano Letters, 2004, 4(2):383-386.

Yamada et al., "Candesartan, an angiotensin II receptor antagonist, suppresses pancreatic inflammation and fibrosis in rats," J. Pharmacol. Exp. Ther., 2003, 307(1):17-23.

Zeichner, J.A. (2010) "Use of Topical Coal Tar Foam for the Treatment of Psoriasis in Difficult-to-treat Areas" *J Clin Aesthet Dermatol*, 3(9):37-40.

Zinc Oxide, Knovel, 2006, retrieved on Apr. 18, 2012, http://www.knovel.com/web/portal/knovel_content?p_p_id=EXT_KNOVEL_CONTENT . . . , 2 pages.

Ziolkowsky, "Moderne Aerosolschaume in der Kosmetik (Modern Aerosol Foams in Chemical and Marketing Aspects)" Seifen-Ole-Fette-Wachse, Aug. 1986, 112(13): 427-429 (with English translation).

Clark, "Acne causes and clinical features," Clinical Pharmacist, 2009, vol. 1, pp. 163-167.

DICARBOXYLIC ACID FOAMABLE VEHICLE AND PHARMACEUTICAL COMPOSITIONS THEREOF

CROSS REFERENCE TO RELATED APPLICATIONS

This application is a divisional application of U.S. patent application Ser. No. 15/903,275, filed on Feb. 23, 2018, which is a continuation application of U.S. patent application Ser. No. 13/796,860, filed on Mar. 12, 2013, which is a continuation application of U.S. patent application Ser. No. 11/825,406, filed on Jul. 5, 2007, which issued as U.S. Pat. No. 9,265,725, claims benefit under 35 U.S.C. § 119(e) of U.S. Provisional Patent Application No. 60/818,634, filed on Jul. 5, 2006; application Ser. No. 11/825,406 is a continuation-in-part of U.S. patent application Ser. No. 11/717,897, filed on Mar. 13, 2007, which issued as U.S. Pat. No. 8,119,109; application Ser. No. 11/717,897 is a continuation-in-part of U.S. patent application Ser. No. 11/078,902, filed on Mar. 11, 2005, which issued as U.S. Pat. No. 9,668,972; all of which are incorporated herein by reference in their entirety.

BACKGROUND OF THE INVENTION

This invention relates to foamable pharmaceutical and cosmetic compositions.

External topical administration is an important route for the administration of drugs in disease treatment. Many groups of drugs, including, for example, antibiotic, antifungal, anti-inflammatory, anesthetic, analgesic, anti-allergic, corticosteroid, retinoid and anti-proliferative medications are preferably administered in hydrophobic media, namely ointment. However, ointments often form an impermeable barrier, so that metabolic products and excreta from the wounds to which they are applied are not easily removed or drained away. Furthermore, it is difficult for the active drug dissolved in the carrier to pass through the white petrolatum barrier layer into the wound tissue, so the efficacy of the drug is reduced. In addition, ointments and creams often do not create an environment for promoting respiration of the wound tissue and it is not favorable to the normal respiration of the skin. An additional disadvantage of petroleum jelly-based products relates to the greasy feeling left following their topical application onto the skin, mucosal membranes and wounds.

Foams are considered a more convenient vehicle for topical delivery of active agents. There are several types of topical foams, including aqueous foams, such as commonly available shaving foams; hydroalcoholic foams, emulsion-based foams, comprising oil and water components, and oleaginous foams, which consist of high oil content. In skin therapy, oil containing foams are preferred, since oil contributes to skin protection and moisturization, which improve the therapeutic effect of the formulation.

Dicarboxylic acids are known to possess therapeutic properties. Dicarboxylic acids, and their mercapto, ester and salt derivatives have been used in the treatment of a variety of skin disorders and/or conditions.

Azelaic acid (AZA) is a naturally occurring nine carbon straight chain molecule with two terminal carboxyl groups. AZA is an anti-keratinizing agent, displaying antiproliferative effects on keratinocytes and modulating the early and terminal phases of epidermal differentiation. AZA is a competitive inhibitor of the reduction of testosterone to dihydrotestosterone, and as such is supposed to reduce the production of sebum in the sebaceous gland. Furthermore, recent investigations have demonstrated that AZA and sebacic acid also have anti-bacterial and anti-fungal properties. Structure-activity relationship studies have revealed that these effects are retained when the dicarboxylic acid has a backbone of about 6 to about 14 carbons.

Dicarboxylic acid esters are also known to contribute to the skin penetration of an active agent. Enhancing effects on skin penetration of methyl nicotinate have been observed with dibutyl adipate and dioctyl adipate. Diisopropyl sebacate also markedly enhances the skin penetration of the erythromycin. The skin penetration enhancing properties of mono- or di-esters of dicarboxylic acid, including dibutyl adipate, diethyl sebacate, diisopropyl dimerate, diisopropyl adipate, diisopropyl sebacate and dioctyl succinate have been recognized.

There remains an unmet need for improved, easy to use, stable oil-containing foam formulations, containing oils, which effectively deliver and/or deposit various benefit agents into and onto the skin and/or other target sites and are relatively non-irritating and thus suitable for use by people having sensitive skin and eyes.

SUMMARY

The present invention relates to aqueous and non aqueous stable compositions comprising a dicarboxylic acid or ester derivative thereof in which the dicarboxylic acid or ester derivative is a stabilizing emollient and or has a therapeutic effect.

There is provided a pharmaceutical or cosmetic composition comprising:
   a. a beneficially or therapeutically effective concentration of at least one benefit agent, selected from the group consisting of
      i. a dicarboxylic acid; and
      ii. a dicarboxylic acid ester;
   b. a stabilizer selected from the group consisting of at least one surface-active agent; at least one polymeric agent and mixtures thereof; and
   c. a solvent selected from the group consisting of water; a hydrophilic solvent; a hydrophobic solvent; a potent solvent; a polar solvent, a silicone, an emollient, and mixtures thereof;
   wherein the benefit agent is an emollient solvent and or a pharmaceutical or cosmetic agent;
   wherein the polymeric agent is about 0.01% to about 5% by weight and is selected from the group consisting of a bioadhesive agent, a gelling agent, a film forming agent and a phase change agent;
   wherein the benefit agent, stabilizer and solvent are selected to provide a composition that is substantially resistant to aging and to phase separation and or can substantially stabilize other active ingredients; and
   wherein if the composition is contained in a pressurized container and further comprises a liquefied hydrocarbon gas propellant at a concentration of about 3% to about 25% by weight of the total composition it is substantially flowable and provides a foam upon release.

There is also provided a foamable composition as described above wherein the composition is contained in a pressurized container and further comprises a liquefied hydrocarbon gas propellant at a concentration of about 3% to about 25% by weight of the total composition, is substantially flowable and provides a foam upon release and wherein the benefit agent, stabilizer and solvent are selected to generate a breakable foam of good to excellent quality.

There is also provided a therapeutic composition comprising:
  a. a therapeutically effective amount of an active agent;
  b. a beneficially or therapeutically effective concentration of at least one benefit agent, selected from the group consisting of
      i. a dicarboxylic acid; and
      ii. a dicarboxylic acid ester;
  c. a stabilizer selected from the group consisting of at least one surface-active agent; at least one polymeric agent and mixtures thereof; and
  d. a solvent selected from the group consisting of water; a hydrophilic solvent; a hydrophobic solvent; a potent solvent; a polar solvent, a silicone, an emollient, and mixtures thereof;
wherein the benefit agent is an emollient solvent and or a pharmaceutical or cosmetic agent;
wherein the polymeric agent is about 0.01% to about 5% by weight and is selected from the group consisting of a bioadhesive agent, a gelling agent, a film forming agent and a phase change agent;
wherein the benefit agent, stabilizer and solvent are selected to provide a composition that is substantially resistant to aging and to phase separation and or can substantially stabilize other active ingredients; and
wherein if the composition is contained in a pressurized container and further comprises a liquefied hydrocarbon gas propellant at a concentration of about 3% to about 25% by weight of the total composition it is substantially flowable and provides a foam upon release.

There is also provided a method of treating a disorder of a mammalian subject, comprising:
administering a foamable therapeutic composition to a target site, the composition comprising:
  e. a therapeutically effective amount of an active agent;
  f. a beneficially or therapeutically effective concentration of at least one benefit agent, selected from the group consisting of
      i. a dicarboxylic acid; and
      ii. a dicarboxylic acid ester;
  g. a stabilizer selected from the group consisting of at least one surface-active agent; at least one polymeric agent and mixtures thereof.
  h. a solvent selected from the group consisting of water; a hydrophilic solvent; a hydrophobic solvent; a potent solvent; a polar solvent, a silicone, an emollient, and mixtures thereof;
wherein the benefit agent is an emollient solvent and or a pharmaceutical or cosmetic agent;
wherein the polymeric agent is about 0.01% to about 5% by weight and is selected from the group consisting of a bioadhesive agent, a gelling agent, a film forming agent and a phase change agent;
wherein the benefit agent, stabilizer and solvent are selected to provide a composition that is substantially resistant to aging and to phase separation and or can substantially stabilize other active ingredients; and
wherein if the composition is contained in a pressurized container and further comprises a liquefied hydrocarbon gas propellant at a concentration of about 3% to about 25% by weight of the total composition it is substantially flowable and provides a foam upon release.

There is also provided a pharmaceutical or cosmetic non aqueous composition comprising:
  a. a beneficially or therapeutically effective concentration of at least one benefit agent, selected from the group consisting of
      i. a dicarboxylic acid; and
      ii. a dicarboxylic acid ester;
  b. a stabilizer selected from the group consisting of at least one surface-active agent; at least one polymeric agent and mixtures thereof; and
  c. a solvent selected from the group consisting of a hydrophilic solvent; a hydrophobic solvent; a potent solvent; a polar solvent, a silicone, an emollient, and mixtures thereof;
wherein the benefit agent is an emollient solvent and or a pharmaceutical or cosmetic agent;
wherein the polymeric agent is about 0.01% to about 5% by weight and is selected from the group consisting of a bioadhesive agent, a gelling agent, a film forming agent and a phase change agent;
wherein the benefit agent, stabilizer and solvent are selected to provide a composition that is substantially resistant to aging and to phase separation and or can substantially stabilize other active ingredients; and
wherein if the composition is contained in a pressurized container and further comprises a liquefied hydrocarbon gas propellant at a concentration of about 3% to about 25% by weight of the total composition it is substantially flowable and provides a foam upon release.

There is also provided a therapeutic composition comprising:
  a. a therapeutically effective amount of an active agent wherein the active agent is substantially insoluble in water;
  b. a beneficially or therapeutically effective concentration of at least one benefit agent, comprising a dicarboxylic acid ester in which the active agent is substantially soluble;
  c. a stabilizer selected from the group consisting of at least one surface-active agent; at least one polymeric agent and mixtures thereof; and
  d. a solvent selected from the group consisting of water; a hydrophilic solvent; a hydrophobic solvent; a potent solvent; a polar solvent, a silicone, an emollient, and mixtures thereof;
wherein the benefit agent is an emollient solvent and or a pharmaceutical or cosmetic agent;
wherein the polymeric agent is about 0.01% to about 5% by weight and is selected from the group consisting of a bioadhesive agent, a gelling agent, a film forming agent and a phase change agent;
wherein the benefit agent, stabilizer and solvent are selected to provide a composition that is substantially resistant to aging and to phase separation and or can substantially stabilize other active ingredients; and
wherein if the composition is contained in a pressurized container and further comprises a liquefied hydrocarbon gas propellant at a concentration of about 3% to about 25% by weight of the total composition it is substantially flowable and provides a foam upon release.

There is also provided a foamable composition comprising:
  a. a liquid dicarboxylic acid ester, said ester having emollient properties;
  b. a stabilizer selected from the group consisting of at least one surface-active agent; at least one polymeric agent and mixtures thereof.
  c. an active agent, said active agent soluble in or having enhanced penetration due to the dicarboxylic acid;
wherein the composition is contained in a pressurized container and further comprises a liquefied hydrocarbon gas propellant at a concentration of about 3% to about 25% by weight of the total composition it is substantially flowable and provides a foam upon release.

There is also provided a foamable composition comprising:
- a. a beneficially or therapeutically effective concentration of at least one benefit agent, selected from the group consisting of
  - i. a dicarboxylic acid; and
  - ii. a dicarboxylic acid ester;
- b. an ester-based or ether-based surfactant;
- c. a solvent selected from the group consisting of a hydrophilic solvent; a hydrophobic solvent; a potent solvent; a polar solvent, a silicone, an emollient, and mixtures thereof;

wherein the composition is substantially free of polymeric material, and wherein the composition is contained in a pressurized container and further comprises a liquefied hydrocarbon gas propellant at a concentration of about 3% to about 25% by weight of the total composition it is substantially flowable and provides a foam upon release.

There is also provided a pharmaceutical or cosmetic composition comprising:
- a. a beneficially or therapeutically effective concentration of at least one benefit agent, selected from the group consisting of
  - i. a dicarboxylic acid; and
  - ii. a dicarboxylic acid ester;
- b. a stabilizer selected from the group consisting of at least one surface-active agent; at least one polymeric agent and mixtures thereof; and
- c. a solvent selected from the group consisting of a hydrophilic solvent; a hydrophobic solvent; a potent solvent; a polar solvent, a silicone, an emollient, and mixtures thereof;

wherein the composition is substantially free of water; and wherein the composition is contained in a pressurized container and further comprises a liquefied hydrocarbon gas propellant at a concentration of about 3% to about 25% by weight of the total composition it is substantially flowable and provides a foam upon release.

There is also provided a formulation of any of the compositions described above wherein the composition is in a non foam state.

There is also provided a formulation of any of the compositions described above for use in the manufacture of a medicament.

DETAILED DESCRIPTION

The present invention relates to a composition comprising a benefit agent, selected from the group consisting of (i) a dicarboxylic acid; and (ii) a dicarboxylic acid ester for use as vehicle composition.

According to one or more embodiments of the present invention, the composition includes:
- a. a benefit agent, selected from the group consisting of
  - i. a dicarboxylic acid; and
  - ii. a dicarboxylic acid ester;
- b. a surface-active agent;
- c. about 0.01% to about 5% by weight of at least one polymeric agent selected from the group consisting of a bioadhesive agent, a gelling agent, a film forming agent and a phase change agent; and
- d. water.

The present invention further relates to a foamable composition including:
- a. a benefit agent, selected from the group consisting of
  - i. a dicarboxylic acid; and
  - ii. a dicarboxylic acid ester;
- b. a surface-active agent;
- c. about 0.01% to about 5% by weight of at least one polymeric agent selected from the group consisting of a bioadhesive agent, a gelling agent, a film forming agent and a phase change agent;
- d. water; and
- e. liquefied hydrocarbon gas propellant at a concentration of about 3% to about 25% by weight of the total composition.

In one or more embodiments there is provided a pharmaceutical or cosmetic composition comprising:
- a. a beneficially or therapeutically effective concentration of at least one benefit agent, selected from the group consisting of
  - i. a dicarboxylic acid; and
  - ii. a dicarboxylic acid ester;
- b. a stabilizer selected from the group consisting of at least one surface-active agent; at least one polymeric agent and mixtures thereof.
- c. a solvent selected from the group consisting of water; a hydrophilic solvent; a hydrophobic solvent; a potent solvent; a polar solvent, a silicone, an emollient, and mixtures thereof;

wherein the benefit agent is an emollient solvent and or a pharmaceutical or cosmetic agent wherein the polymeric agent is about 0.01% to about 5% by weight and is selected from the group consisting of a bioadhesive agent, a gelling agent, a film forming agent and a phase change agent;

wherein the benefit agent, stabilizer and solvent are selected to provide a composition that is substantially resistant to aging and to phase separation and or can substantially stabilize other active ingredients;

wherein if the composition is contained in a pressurized container and further comprises a liquefied hydrocarbon gas propellant at a concentration of about 3% to about 25% by weight of the total composition it is substantially flowable and provides a foam upon release.

In one or more embodiments there is provided a foamable composition which produces a foam upon release and wherein the benefit agent, stabilizer and solvent are selected to generate a breakable foam of good to excellent quality.

In one or more embodiments there is provided a composition wherein the benefit agent, stabilizer and solvent are selected to generate an emulsion that is substantially resistant to phase reversal.

In one or more embodiments there is provided a composition wherein, the benefit agent, stabilizer and solvent are selected to generate a single phase.

In one or more embodiments there is provided a composition wherein, the benefit agent, stabilizer and solvent are selected to generate a substantially uniform suspension of benefit agent crystals.

In one or more embodiments there is provided a composition, wherein the breakable foam comprises micro or nano particles, crystals or bodies.

In one or more embodiments there is provided a composition, which is substantially resistant to one or more Freeze-Thaw cycles (FTC).

In one or more embodiments there is provided a composition wherein the surface-active agent is a solid, a liquid or a mixture thereof.

In one or more embodiments there is provided a composition wherein the surface active agent is selected from the group consisting of a polysorbate, polyoxyethylene (20) sorbitan monostearate, polyoxyethylene (20) sorbitan monooleate, a polyoxyethylene fatty acid ester, Myrj 45, Myrj 49, Myrj 52 and Myrj 59; a polyoxyethylene alkylyl ether, polyoxyethylene cetyl ether, polyoxyethylene palmityl ether, polyethylene oxide hexadecyl ether, polyethylene glycol cetyl ether, brij 38, brij 52, brij 56 and brij W1, a sucrose ester, a partial ester of sorbitol, sorbitan monolaurate, sorbitan monolaurate a monoglyceride, a diglyceride, isoceteth-20, a sucrose ester, or selected from the group consisting of steareth 2, glyceryl monostearate/PEG 100 stearate, Glyceryl Stearate, Steareth-21, peg 40 stearate, polysorbate 60, polysorbate 80, sorbitan stearate, laureth 4, Sorbitan monooleate, ceteareth 20, steareth 20, ceteth 20, Macrogol Cetostearyl Ether, ceteth 2, PEG-30 Dipolyhydroxystearate, sucrose distearate, polyoxyethylene (100) stearate, PEG 100 stearate, laureth 4, cetomacrogol ether, Cetearyl alcohol, Cetearyl glucoside, Oleyl alcohol, Steareth-2, Diisopropyl adipate, Capric/caprilic triglicerides, Polysorbate 20; Montanov 68 (CETEARYL ALCOHOL (and) CETEARYL GLUCOSIDE), Sharonmix 824 (a liquid blend of methyl paraben, ethyl paraben and propyl paraben—in phenoxyethanol), Simusol 165 (Glyceryl stearate and PEG-100 stearate). Methyl glucose sequistearate, Peg 30 dipolyhydroxystearate, sucrose stearic acid esters, sorbitan laureth, sorbitan stearate and mixtures thereof.

In one or more embodiments there is provided a composition wherein the surface active agent comprises at least one ester based surfactant or at least one ether based surfactant.

In one or more embodiments there is provided a composition wherein the surface active agent is reduced about in proportion to the increase in dicarboxylic ester.

In one or more embodiments there is provided a composition wherein the stabilizer is not a polymeric agent.

In one or more embodiments there is provided a composition wherein the surface active agent comprises a non-ionic surfactant that does not contain a polyoxyethylene (POE) moiety.

In one or more embodiments there is provided a composition wherein the surface active agent is selected from the group consisting of a non-ethoxylated sorbitan ester, a glycerol fatty acid ester, a sucrose ester and an alkyl polyglycoside or is selected from the group consisting of sorbitan monopalmitate, sorbitan monostearate, sorbitan tristearate, sorbitan monooleate, sorbitan trioleate, sorbitan monolaurate, sorbitan sesquioleate, glycerol monostearate, glycerol monooleate, sucrose stearate, sucrose distearate, sucrose palmitate sucrose laurate and lauryl diglucoside.

In one or more embodiments there is provided a composition wherein the polymeric agent is selected from the group consisting of carbopol 934, pemulen TR2, klucel EF, xanthan gum, methocel A4M, and carboxy methyl cellulose or selected from the group consisting of locust bean gum, sodium alginate, sodium caseinate, egg albumin, gelatin agar, carrageenin gum, sodium alginate, xanthan gum, quince seed extract, tragacanth gum, guar gum, cationic guars, hydroxypropyl guar gum, starch, an amine-bearing polymer, chitosan, alginic acid, hyaluronic acid, a chemically modified starch, a carboxyvinyl polymer, polyvinylpyrrolidone, polyvinyl alcohol, a polyacrylic acid polymer, a polymethacrylic acid polymer, polyvinyl acetate, a polyvinyl chloride polymer, a polyvinylidene chloride polymer, methylcellulose, hydroxypropyl cellulose, hydroxypropyl methylcellulose, hydroxyethyl cellulose, hydroxy propylmethyl cellulose, methylhydroxyethylcellulose, methylhydroxypropylcellulose, hydroxyethylcarboxymethylcellulose, carboxymethyl cellulose, carboxymethylcellulose carboxymethylhydroxyethylcellulose, a cationic cellulose aluminum starch octenylsuccinate (ASOS), PEG 1000, PEG 4000, PEG 6000 and PEG 8000.

In one or more embodiments there is provided a composition wherein the polymeric agent is a derivatized polymer.

In one or more embodiments there is provided a composition wherein the derivatized polymer is a polymeric emulsifier.

In one or more embodiments there is provided a composition wherein the benefit agent is selected from the group consisting of diisopropyl adipate, dimethyl sebacate, dioctyl malate, diethyl sebacate, azelaic acid and TU-2100.

In one or more embodiments there is provided a composition wherein, further comprising an additional active agent.

In one or more embodiments there is provided a composition wherein the dicarboxylic acid has the molecular formula HOOC—$(CH_2)_n$—COOH; and wherein n is in the range between 0 and 32.

In one or more embodiments there is provided a composition wherein n is in the range between 4 and 10.

In one or more embodiments there is provided a composition wherein the dicarboxylic acid is selected from the group consisting of oxalic acid, malonic acid, succinic acid, glutaric acid, adipic acid, pimelic acid, suberic acid, azelaic acid, sebacic acid and dodecanedioic acid, maleic acid and fumaric acid.

In one or more embodiments there is provided a composition wherein the dicarboxylic acid is selected from the group consisting of adipic acid, azelaic acid and sebacic acid.

In one or more embodiments there is provided a composition wherein further containing a foam adjuvant selected from the group consisting of a fatty alcohol having 15 or more carbons in their carbon chain; a fatty acid having 16 or more carbons in their carbon chain; fatty alcohols, derived from beeswax and including a mixture of alcohols, a majority of which has at least 20 carbon atoms in their carbon chain; a fatty alcohol having at least one double bond; a fatty acid having at least one double bond; a branched fatty alcohol; a branched fatty acid and a fatty acid substituted with a hydroxyl group.

In one or more embodiments there is provided a composition wherein further containing at least one organic carrier selected from the group consisting of a hydrophobic organic carrier, an emollient and mixtures thereof, at a concentration of about 2% to about 50% by weight.

In one or more embodiments there is provided a composition wherein the dicarboxylic acid or dicarboxylic acid ester is in a concentration between about 0.1% and about 60%.

In one or more embodiments there is provided a composition wherein the dicarboxylic acid is azelaic acid, and wherein the concentration of azelaic acid is between 5% and 25%.

In one or more embodiments there is provided a composition wherein the pH of the composition is below the first pKa of the dicarboxylic acid.

In one or more embodiments there is provided a composition wherein the pH of the composition is between the first and second pKa of the dicarboxylic acid.

In one or more embodiments there is provided a composition wherein the pH of the composition is above the second pKa of the dicarboxylic acid.

In one or more embodiments there is provided a composition wherein the dicarboxylic acid is azelaic acid the pH of the composition is below 5.3.

In one or more embodiments there is provided a composition wherein the dicarboxylic acid is azelaic acid the pH of the composition is between about 4.5 and about 5.3.

In one or more embodiments there is provided a composition wherein the dicarboxylic acid ester is selected from the group consisting of a mono ester of said dicarboxylic acid, and a diester of the dicarboxylic acid.

In one or more embodiments there is provided a composition wherein the alcohol moiety of the dicarboxylic acid ester is selected from the group consisting of an alkyl alcohol, an aryl alcohol, methyl alcohol, ethyl alcohol, propyl alcohol, isopropyl alcohol, butyl alcohol, isobutyl alcohol, t-butyl alcohol, pentyl alcohol, hexyl alcohol, octyl alcohol, decyl alcohol, capryl alcohol, phenol and benzyl alcohol.

In one or more embodiments there is provided a composition wherein the alcohol moiety of the dicarboxylic acid ester is a biologically active alcohol.

In one or more embodiments there is provided a composition wherein the biologically active alcohol is selected from the group consisting of a hydroxyalkylbenzoate, salicylic acid, a dihydroxybenzene, hydroxytoluene, an alpha-hydroxy acid, retinol, a vitamin A derivative, a steroid, vitamin E, a vitamin E derivative, vitamin D and a vitamin D derivative.

In one or more embodiments there is provided a composition wherein the dicarboxylic acid ester is selected from the group consisting of diisobutyl adipate, diisopropyl adipate, diisopropyl sebacate, diisosteary dimer dilinoleate, diisostearyl fumerate, diisopropyl dimerate, diethyl adipate, diethyl sebacate, diethylhexyl adipate, diethylhexyl malate, dioctyl malate, diethyl succinate, and dioctyl sebacate.

In one or more embodiments there is provided a composition wherein the dicarboxylic acid ester is diisopropyl adipate, in an amount from about 0.1% to about 60%

In one or more embodiments there is provided a composition wherein the organic carrier is selected from the group consisting of mineral oil, triglycerides, medium chain triglyceride (MCT) oil, capric/caprylic triglyceride, alkyl esters of fatty acids such as isopropyl palmitate, isopropyl myristate, isopropyl isostearate, poly propylene glycol 15-stearly ether, octyl palmitate, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, ricinoleate, isopropyl lanolate, pentaerythrityl tetrastearate, neopentylglycol dicaprylate/dicaprate, isononyl isononanoate, isotridecyl isononanoate, myristyl myristate, triisocetyl citrate, octyl dodecanol, maleated soybean oil, unsaturated or polyunsaturated oils, such as olive oil, corn oil, soybean oil, canola oil, cottonseed oil, coconut oil, sesame oil, sunflower oil, borage seed oil, syzigium aromaticum oil, hempseed oil, herring oil, codliver oil, salmon oil, flaxseed oil, wheat germ oil, evening primrose oils; essential oils; and silicone oils, such as dimethicone, cyclomethicone, polyalkyl siloxane, polyaryl siloxane, polyalkylaryl siloxane, a polyether siloxane copolymer and a poly(dimethylsiloxane)-(diphenyl-siloxane) copolymer.

In one or more embodiments there is provided a composition wherein the organic carrier comprises a polypropylene glycol alkyl ether.

In one or more embodiments there is provided a composition further containing at least one polar solvent.

In one or more embodiments there is provided a composition wherein the polar solvent is selected from the group consisting of dimethyl isosorbide, glycerol, propylene glycol, hexylene glycol, diethylene glycol, propylene glycol n-alkanols, terpenes, di-terpenes, tri-terpenes, limonene, terpene-ol, 1-menthol, dioxolane, ethylene glycol, other glycols, oleyl alcohol, alpha-hydroxy acids, such as lactic acid and glycolic acid, sulfoxides, such as dimethylsulfoxide (DMSO), dimethylformanide, methyl dodecyl sulfoxide, dimethylacetamide, azone (1-dodecylazacycloheptan-2-one), 2-(n-nonyl)-1,3-dioxolane, alkanols, such as dialkylamino acetates, and admixtures thereof.

In one or more embodiments there is provided a composition wherein the organic carrier is capric/caprylic triglyceride and wherein the dicarboxylic acid is azelaic acid.

In one or more embodiments there is provided a composition wherein the polar solvent is selected from the group consisting of dimethyl isosorbide, glycerol, propylene glycol, hexylene glycol, terpene-ol, oleyl alcohol, lactic acid and glycolic acid wherein the dicarboxylic acid is azelaic acid.

In one or more embodiments there is provided a composition wherein the organic carrier is capric/caprylic triglyceride.

In one or more embodiments there is provided a composition wherein the organic solvent comprises at least one organic carrier, selected from the group capric/caprylic triglyceride, a polypropylene glycol alkyl ether an ester of a fatty acid and mineral oil and wherein the dicarboxylic acid ester is diisopropyl adipate.

In one or more embodiments there is provided a composition further comprising a polar solvent, selected from the group consisting of dimethyl isosorbide, glycerol, propylene glycol, hexylene glycol, terpene-ol, oleyl alcohol, lactic acid and glycolic acid.

In one or more embodiments there is provided a composition wherein the benefit agent, stabilizer and solvent are selected to generate an emulsion that can produce a substantially strong and closed packed barrier between the oil and the water phases whilst maintaining a fluid constitution In one or more embodiments there is provided a composition further comprising an additional component selected from the group consisting of a modulating agent, a polar solvent, an anti perspirant, an anti-static agent, a buffering agent, a bulking agent, a chelating agent, a colorant, a conditioner, a deodorant, a diluent, a dye, an emollient, fragrance, a humectant, an occlusive agent, a penetration enhancer, a perfuming agent, a permeation enhancer, a pH-adjusting agent, a preservative, a skin penetration enhancer, a sunscreen, a sun blocking agent, a sunless tanning agent, and a vitamin.

In one or more embodiments there is provided a composition wherein the organic carrier is selected from the group consisting of PPG 15-stearyl ether, isopropyl myristate and medium chain triglyceride oil and capric/caprylic triglyceride and the benefit agent is a solid at ambient temperature.

In one or more embodiments there is provided a therapeutic composition comprising therapeutically effective amount of an active agent; and a beneficially or therapeutically effective concentration of at least one benefit agent, selected from the group consisting of:
 i. a dicarboxylic acid; and
 ii. a dicarboxylic acid ester
wherein the active agent is selected from the group consisting of active herbal extracts, acaricides, age spot and keratose removing agents, allergen, analgesics, local anesthetics, antiacne agents, antiallergic agents, antiaging agents, antibacterials, antibiotics, antiburn agents, anticancer agents, antidandruff agents, antidepressants, antidermatitis agents, antiedemics, antihistamines, antihelminths, antihyperkeratolyte agents, antiinflammatory agents, antiirritants, antilipemics, antimicrobials, antimycotics, antiproliferative agents, antioxidants, anti-wrinkle agents, antipruritics, antipsoriatic agents, antirosacea agents antiseborrheic agents, antiseptic, antiswelling agents, antiviral agents, antiyeast agents, astringents, topical cardiovascular agents, chemotherapeutic agents, corticosteroids, dicarboxylic acids, disinfectants, fungicides, hair growth regulators, hormones, hydroxy acids, immunosuppressants, immunoregulating agents, insecticides, insect repellents, keratolytic agents, lactams, metals, metal oxides, mitocides, neuropeptides, non-steroidal anti-inflammatory agents, oxidizing agents, pediculicides, photodynamic therapy agents, retinoids, sanatives, scabicides, self tanning agents, skin whitening agents, vasoconstrictors, vasodilators, vitamins, vitamin D derivatives, wound healing agents and wart removers.

In one or more embodiments there is provided a foamable therapeutic composition wherein the dicarboxylic acid ester is present in the composition in an amount sufficient to solubilize the active agent.

In one or more embodiments there is provided a foamable therapeutic composition wherein the active agent is a steroid.

In one or more embodiments there is provided a foamable therapeutic composition wherein the steroid is selected from the group consisting of bydrocortisone, hydroxyltriamcinolone, alpha-methyl dexamethasone, dexamethasone-phosphate, beclomethsone dipropionate, clobetasol valemate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortmate, mepreddisone, paramethasone, prednisolone, prednisone, beclomethasone dipropionate, triamcinolone.

In one or more embodiments there is provided a foamable therapeutic composition wherein the active agent is an immunomodulator.

In one or more embodiments there is provided a foamable therapeutic composition, wherein the immunomodulator is selected from the group consisting of a cyclic peptides, cyclosporine, tacrolimus, tresperimus, pimecrolimus, sirolimus, verolimus, laflunimus, laquinimod and imiquimod.

In one or more embodiments there is provided a foamable therapeutic composition wherein the dicarboxylic acid ester is present in the composition in an amount sufficient to solubilize the immunomodulator.

In one or more embodiments there is provided a foamable therapeutic composition, wherein the dicarboxylic acid ester is diisopropyl adipate.

In one or more embodiments there is provided a composition wherein the surface active agent comprises a non-ionic surfactant that does not contain a polyoxyethylene (POE) moiety.

In one or more embodiments there is provided a composition wherein the surface active agent is selected from the group consisting of a non-ethoxylated sorbitan ester, a glycerol fatty acid ester, a sucrose ester and an alkyl polyglycoside or is selected from the group consisting of sorbitan monopalmitate, sorbitan monostearate, sorbitan tristearate, sorbitan monooleate, sorbitan trioleate, sorbitan monolaurate, sorbitan sesquioleate, glycerol monostearate, glycerol monooleate, sucrose stearate, sucrose distearate, sucrose palmitate sucrose laurate and lauryl diglucoside.

In one or more embodiments there is provided a composition wherein the dicarboxylic acid is azelaic acid.

In one or more embodiments there is provided a composition wherein the dicarboxylic acid is azelaic acid and further comprising an organic solvent comprising capric/caprylic triglyceride.

In one or more embodiments there is provided a composition wherein the dicarboxylic acid is azelaic acid and further comprising an organic solvent comprising capric/caprylic triglyceride and further comprising at least one polar carrier, selected from the group consisting of dimethyl isosorbide, glycerol, propylene glycol, hexylene glycol, terpene-ol, oleyl alcohol, lactic acid and glycolic acid.

In one or more embodiments there is provided a method of treating a disorder of a mammalian subject, comprising:
 administering a foamable therapeutic composition to a target site, the composition comprising a therapeutically effective amount of an active agent; and a beneficially or therapeutically effective concentration of at least one benefit agent, selected from the group consisting of
 i. a dicarboxylic acid; and
 ii. a dicarboxylic acid ester;
wherein the target site is selected from the group consisting of the skin, a body cavity, a mucosal surface, the nose, the mouth, the eye, the ear canal, the respiratory system, the vagina and the rectum.

In one or more embodiments there is provided a method of treating a disorder of a mammalian subject, wherein the disorder is selected from the group consisting of dermatological pain, dermatological inflammation, acne, acne vulgaris, inflammatory acne, non-inflammatory acne, acne fulminans, nodular papulopustular acne, acne conglobata, dermatitis, bacterial skin infections, fungal skin infections, viral skin infections, parasitic skin infections, skin neoplasia, skin neoplasms, pruritis, cellulitis, acute lymphangitis, lymphadenitis, erysipelas, cutaneous abscesses, necrotizing subcutaneous infections, scalded skin syndrome, folliculitis, furuncles, hidradenitis suppurativa, carbuncles, paronychial infections, rashes, erythrasma, impetigo, ecthyma, yeast skin infections, warts, molluscum contagiosum, trauma or injury to the skin, post-operative or post-surgical skin conditions, scabies, pediculosis, creeping eruption, eczemas, psoriasis, pityriasis rosea, lichen planus, pityriasis rubra pilaris, edematous, erythema multiforme, erythema nodosum, granuloma annulare, epidermal necrolysis, sunburn, photosensitivity, pemphigus, bullous pemphigoid, dermatitis herpetiformis, keratosis pilaris, callouses, corns, ichthyosis, skin ulcers, ischemic necrosis, miliaria, hyperhidrosis, moles, Kaposi's sarcoma, melanoma, malignant melanoma, basal cell carcinoma, squamous cell carcinoma, poison ivy, poison oak, contact dermatitis, atopic dermatitis, rosacea, purpura, moniliasis, candidiasis, baldness, alopecia, Behcet's syndrome, cholesteatoma, Dercum disease, ectodermal dysplasia, gustatory sweating, nail patella syndrome, lupus, hives, hair loss, Hailey-Hailey disease, chemical or thermal skin burns, scleroderma, aging skin, wrinkles, sun spots, necrotizing fasciitis, necrotizing myositis, gangrene, scarring, and vitiligo; and wherein the active agent is suitable for treating said disorderm or is selected from the group consisting of chlamydia infection, gonorrhea infection, hepatitis B, herpes, HIV/AIDS, human papillomavirus (HPV), genital warts, bacterial vaginosis, candidiasis, chancroid, granuloma Inguinale, lymphogranuloma venereum, mucopurulent cervicitis (MPC), molluscum contagiosum, nongonococcal urethritis (NGU), trichomoniasis, vulvar disorders, vulvodynia, vulvar pain, yeast infection, vulvar dystrophy, vulvar intraepithelial neoplasia (VIN), contact dermatitis, pelvic inflammation, endometritis, salpingitis, oophoritis, genital cancer, cancer of the cervix, cancer of the vulva, cancer of the vagina, vaginal dryness, dyspareunia, anal and rectal disease, anal abscess/fistula, anal cancer, anal fissure, anal warts, Crohn's disease, hemorrhoids, anal itch, pruritus ani, fecal incontinence, constipation, polyps of the colon and rectum; and wherein the active agent is suitable for treating said disorder.

In one or more embodiments there is provided a method of treating a disorder of a mammalian subject, wherein the disorder is a dermatological disorder, which can be treated by a dicarboxylic acid or dicarboxylic acid ester.

In one or more embodiments there is provided a method of treating a disorder of a mammalian subject, wherein the disorder is a dermatological disorder, which can be treated by a topical steroid, an immunomodulator or an anti-infective agent.

In one or more embodiments there is provided a method of treating a disorder of a mammalian subject, wherein the disorder is selected from atopic dermatitis and psoriasis; and the active agent is selected from (i) steroid; and (ii) a combination of steroid and an additional non-steroidal active agent.

In one or more embodiments there is provided a method of treating a disorder of a mammalian subject, wherein the disorder is selected from psoriasis and atopic dermatitis and the active agent comprises an immunomodulator.

In one or more embodiments there is provided a therapeutic composition comprising: a therapeutically effective amount of an active agent wherein the active agent is substantially insoluble in water; and a beneficially or therapeutically effective concentration of at least one benefit agent, comprising a dicarboxylic acid ester in which the active agent is substantially soluble; wherein the benefit agent, stabilizer and solvent are selected to generate an emulsion that can produce a substantially strong and closed packed barrier between the oil and the water phases whilst maintaining a fluid constitution.

In one or more embodiments there is provided a foamable composition comprising: a liquid dicarboxylic acid ester, said ester having emollient properties; a stabilizer selected from the group consisting of at least one surface-active agent; at least one polymeric agent and mixtures thereof, an active agent, said active agent soluble in or having enhanced penetration due to the dicarboxylic acid; wherein the composition is contained in a pressurized container and further comprises a liquefied hydrocarbon gas propellant at a concentration of about 3% to about 25% by weight of the total composition it is substantially flowable and provides a foam upon release In one or more embodiments the stabilizer comprises a ether-based or ester-based surfactant.

In one or more embodiments the stabilizer comprises an alkyl-derivatized polymer having polymeric emulsifying properties.

In one or more embodiments the composition is an oil in water emulsion.

In one or more embodiments the dicarboxylic acid ester comprises about or more than 50 wt % of the composition.

In one or more embodiments the active agent is otherwise insoluble or unstable, but is solubilized or stabilized by DCA.

In one or more embodiments the composition is substantially free of water

In one or more embodiments the composition is in a non foam state.

In one or more embodiments there is provided a pharmaceutical or cosmetic composition comprising:
a. a benefit agent, selected from the group consisting of
   i. a dicarboxylic acid; and
   ii. a dicarboxylic acid ester;
b. a surface-active agent;
c. about 0.01% to about 5% by weight of at least one polymeric agent selected from the group consisting of a bioadhesive agent, a gelling agent, a film forming agent and a phase change agent; and
d. water.

All % values are provided on a weight (w/w) basis.

Dicarboxylic Acid and Esters Thereof

In an embodiment of the present invention, the organic carrier comprises an ester of a dicarboxylic acid. In the context of the present invention, a dicarboxylic acid is an organic material, having two carboxylic acid moieties on its carbon atom skeleton. They have the general molecular formula HOOC—$(CH_2)_n$—COOH.

Non limiting examples of some elementary dicarboxylic acids (DCA's) are succinic acid, glutaric acid, adipic acid, pimelic acid, suberic acid, azelaic acid, sebacic acid, phthalic acid, isophthalic acid, terephthalic acid.

In an embodiment of the present invention, the dicarboxylic acid is a short-chain dicarboxylic acid. The simplest Short-chain dicarboxylic acid are oxalic acid (n=0), malonic acid (n=1), succinic acid (n=2) and glutaric acid (n=3).

Additional members of dicarboxylic acid group are derived from natural products or from synthesis, having "n" value from 4 up to 21. In one or more embodiments of the present invention, the dicarboxylic acid is selected from the group consisting of adipic acid (hexanedioic acid; n=4), pimelic acid (heptanedioic acid; n=5), suberic acid (octanedioic acid; n=6), azelaic acid (nonanedioic acid; n=7), sebacic acid (decanedioic acid; n=8) and dodecanedioic acid (n=10).

In an additional embodiment, the dicarboxylic acid contains 10 to 32 carbon atoms in their carbon atom skeleton, such as brassylic acid (n=11), thapsic acid (n=14), 14-methylnonacosanedioic acid (C29) and 14,15-dimethyltriacontanedioic acid (C30).

The carbon atom skeleton of the dicarboxylic acid can be saturated or unsaturated, such as in the case of maleic acid and fumaric acid.

In general terms non-esterified dicarboxylic acids are usually solid at ambient temperature. Non limiting examples of solid DCA's are oxalic, malonic glutaric, sebacic, phthalic and azaleic acid. Similarly, in general terms DCA's with short carbon chain skeleton are water soluble, such as oxalic, malonic, and succinic acid. Longer chain DCA's like adipic acid and having up to 10 carbon atoms in the carbon chain are slightly soluble in water. Also non "simple" DCA's are generally solid at ambient temperature, insoluble in water, and are usually more oil soluble than their parent DCA's An ester of a dicarboxylic acid is a chemical compound produced by the reaction between a dicarboxylic acid and at least one alcohol, with the elimination of a molecule of water. The reaction of a dicarboxylic acid with one alcohol molecule results in a mono ester of a dicarboxylic acid. The reaction of a dicarboxylic acid with two alcohol molecules results in a diester of the dicarboxylic acid.

DCA esters are typically hydrophobic and generally insoluble in water. Most simple esters of DCA are liquid. By simple it is meant that the alcohol moiety linked to the DCA is a straight or branched alkyl chain. Examples of liquid simple diesters are dimethyl phthalate, diethyl phthalate, dibutyl phthalate, diethyl sebacate, dibutyl sebacate, and diisopropyl adipate. Aromatic diesters of pthalic, isopthalic and therephalic acids are in the range of slightly soluble to insoluble.

The alcohol molecule, to be linked to the dicarboxylic acid, can be selected from the group of an alkyl an aryl alcohol. Exemplary alcohol, suitable according to the present invention include methyl alcohol, ethyl alcohol, propyl alcohol, isopropyl alcohol, butyl alcohol, isobutyl alcohol, t-butyl alcohol, pentyl alcohol, hexyl alcohol, octyl alcohol, decyl alcohol, capryl alcohol, phenol, benzyl alcohol and the like.

In one or more embodiments, the alcohol is a biologically active alcohol. In an embodiment, biologically active alcohol possesses keratolytic activities. Examples of keratolytically active alcohol suitable according to the present invention include ortho-, meta- and para-hydroxyalkylbenzoate, salicylic acid, ortho-, meta-, and para-dihydroxybenzene, ortho-, meta-, and para-hydroxytoluene, alpha-hydroxy acid, retinol, and derivatives thereof such as provided in U.S. Pat. No. 6,180,669, which is incorporated herein by reference. In another embodiment, the biologically active alcohol is selected from the group consisting of steroidal hormones, steroidal anti-inflammatory agents, vitamin E and vitamin D, such as provided in U.S. Pat. Appl. 20040191196, which is incorporated herein by reference.

In an embodiment of the present invention, the dicarboxylic acid is incorporated in the foamable composition in a safe and effective amount. The term "safe and effective" means an amount of an active agent that exerts a therapeutic effect on a specific disorder, without causing adverse effects that may prohibit the use of said active agent in the treatment of said disorder. The dicarboxylic acid can be incorporated in the foamable composition of the present invention in a concentration between about 0.1% and about 25%, more preferably between about 1% and about 20%.

In an embodiment of the present invention, the dicarboxylic acid is azelaic acid, and its concentration in the composition is between 5% and 25%, or between 10% and 20%.

In one or more embodiments, the dicarboxylic acid is present in the composition in an ionized state. The first and second pKa values for a dicarboxylic acid are different from one another. Depending on the pH of the composition and the specific first and second pKa of the dicarboxylic acid, said dicarboxylic acid can be non-ionized (both carboxy groups are in their acid state); semi-ionized (one carboxy group is in an acid state and the second is in an anionic state); or doubly-ionized, wherein both carboxy groups are anionic. For example, in maleic acid the first pKa is 1.9 and the second pKa is 4.4. Therefore, if the pH of the composition is between about 2 and about 4.3, the maleic acid is mostly semi-ionized and at pH above 4.5 the maleic acid is mostly doubly-ionized. Likewise, in the case of azelaic acid the first pKa is about 4.5 and the second pKa is about 5.3. Therefore, if the pH of the composition is below 4.5, the azelaic acid is non-ionized; between about 4.5 and about 5.3, it is mostly semi-ionized and at a pH above 5.3, the azelaic acid is mostly doubly-ionized.

The ionization state of the dicarboxylic acid has influence on its therapeutic potential. On one hand, if the dicarboxylic acid is doubly anionic, its penetration into the skin will be very low, due to the lipophilic nature of the skin. On the other hand, the non-ionic state is available at very low (acidic) pH values, which can cause skin irritation.

Hence, in one or more embodiments, the pH of the composition is adjusted to a value between the first and second pKa values of the dicarboxylic acid. For example, in the case of azelaic acid, the pH is adjusted in the range from about 2.0 to about 4.5, preferably in the range from about 3.0 to about 4.5. Thus, in an embodiment of the present invention, the dicarboxylic acid is azelaic acid, and the pH of the composition is adjusted in the range from about 4.0 to about 6.0, preferably in the range from about 4.5.0 to about 5.3.

Dicarboxylic acid esters are considered excellent emollients and their inclusion in a composition which is intended for topical application contributes to the overall improvement of skin condition. Emollient dicarboxylic esters typically include an alkyl alcohol moiety, wherein said alkyl alcohol has a carbon chain of at least one or two or more carbon atoms. In certain embodiments, the alkyl alcohol is a branched alkyl, such as isopropyl alcohol; and in other embodiments the alkyl alcohol has a long carbon backbone, e.g., a carbon chain length of 6-18.

Dicarboxylic acid esters can be complex substances. One example is TU 2100 (Nonanedioic acid, bis[(2-(ethoxycarbonyl)phenyl] ester). It is also known as Azelaoyl di(ethyl salicylate) and has a CAS Registry Number: [207972-39-2] and is a solid. TU-2100 is a "non-simple" diester; with a high molecular weight, and a melting point of 34-36, which is relatively low with reference to its molecular weight.

Non-limiting examples of emollient dicarboxylic acid esters include diisobutyl adipate, diisopropyl adipate, diisopropyl sebacate, diisosteary dimer dilinoleate, diisostearyl fumerate, diisopropyl dimerate, diethyl adipate, diethyl sebacate, diethylhexyl adipate, diethylhexyl malate, dioctyl malate, diethyl succinate, and dioctyl sebacate. Other diccarboxylic acid esters are dimethyl phthalate, diethyl phthalate, diethyl sebacate, diisopropyl dimerate, dibutyl sebacate, dibutyl phthalate and dioctyl phthalate. Additionally dicarboxylic acid esters are capable of solubilizing active components which are difficult to dissolve by other oils. Furthermore, certain dicarboxylic acid esters, such as diisopropyl adipate and dimethyl sebacate are known to enhance the skin penetration of active agents. Hence in an embodiment of the present invention, the dicarboxylic acid ester is incorporated in the foamable composition in an amount, suitable to exert its emollient effect, solubilizing effect or skin penetration enhancing effect. In one or more embodiments, the dicarboxylic acid ester is incorporated in the foamable composition of the present invention in a concentration between about 0.1% and about 30%, more preferably between about 1% and about 25%.

In one embodiment, the dicarboxylic acid ester is diisopropyl adipate (DISPA), in an amount between about 0.1% and about 30%, or about 1% and about 25%.

As can be appreciated by the discussion above, there is a varied range of dicarboxylic acids and esters; some are solid, some are liquid, some are water soluble, some are slightly soluble and others are insoluble in water. There is also a varied range of functions and physical properties. Some are active agents and others are solvents and some are penetration enhancers. The challenges of making a uniform solution of solid DCA's without crystal formation or precipitation or a uniform suspension of insoluble agent, or using a DCA to solubilise a substance which is otherwise insoluble or as an emollient or as a penetration enhancer or more than one of them are as varied as their different natures and properties as may be appreciated by a man of the art. In other words each agent has its own properties and challenges which are interrelated to the objectives and other ingredients of the formulation The sensory properties of foams containing a dicarboxylic acid or a dicarboxylic acid ester are favorable, as revealed by consumer panel tests.

Foam Adjuvant

Optionally, the foamable vehicle further includes a foam adjuvant selected from the group consisting of a fatty alcohol having 15 or more carbons in their carbon chain; a fatty acid having 16 or more carbons in their carbon chain; fatty alcohols, derived from beeswax and including a mixture of alcohols, a majority of which has at least 20 carbon atoms in their carbon chain; a fatty alcohol having at least one double bond; a fatty acid having at least one double bond; a branched fatty alcohol; a branched fatty acid and a fatty acid substituted with a hydroxyl group.

Additional Organic Carrier

Optionally, the foamable vehicle further includes at least one additional organic carrier selected from the group consisting of a hydrophobic organic carrier, an emollient and mixtures thereof, at a concentration of about 2% to about 50% by weight. The hydrophobic solvent and/or the emollient can be selected from the group consisting of mineral oil, triglycerides, capric/caprylic triglyceride, alkyl esters of fatty acids such as isopropyl palmitate, isopropyl isostearate, octyl palmitate, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, ricinoleate, isopropyl lanolate, pentaerythrityl tetrastearate, neopentylglycol dicaprylate/dicaprate, isononyl isononanoate, isotridecyl isononanoate, myristyl myristate, triisocetyl citrate, octyl dodecanol, maleated soybean oil, unsaturated or polyunsaturated oils, such as olive oil, corn oil, soybean oil, canola oil, cottonseed oil, coconut oil, sesame oil, sunflower oil, borage seed oil, syzigium *aromaticum* oil, hempseed oil, herring oil, cod-liver oil, salmon oil, flaxseed oil, wheat germ oil, evening primrose oils; essential oils; and silicone oils, such as dimethicone, cyclomethicone, polyalkyl siloxane, polyaryl siloxane, polyalkylaryl siloxane, a polyether siloxane copolymer and a poly(dimethylsiloxane)-(diphenyl-siloxane) copolymer.

In an embodiment of the present invention, the organic carrier is a polypropylene glycol alkyl ether (PPG alkyl ether). PPG alkyl ethers are liquid, water-insoluble propoxylated fatty alcohols, having the molecular formula of $RO(CH_2CHOCH_3)_n$; wherein "R" is a straight-chained or branched $C_4$ to $C_{22}$ alkyl group; and "n" is in the range between 4 and about 50. They are organic liquids that function as skin-conditioning agent in pharmaceutical and cosmetic formulations. Non-limiting exemplary PPG alkyl ethers include PPG stearyl ethers and PPG Butyl Ether. Preferred PPG alky ethers according to the present invention include PPG-15 Stearyl Ether, PPG-2 Butyl Ether, PPG-9-13 Butyl Ether and PPG-40 Butyl Ether.

According to a preferred embodiment, the organic carrier does not contain petrolatum, which is also termed "white petrolatum" and "Vaseline". Petrolatum often forms an impermeable occlusive barrier, so that metabolic products and excreta from damaged tissue are not easily removed or drained away. Furthermore, it is difficult for the active drug dissolved in the carrier to pass through the white petrolatum barrier layer into the treated tissue, so the efficacy of the drug is reduced. An additional disadvantage of petroleum jelly-based products relates to the greasy feeling left following their topical application onto the skin, mucosal membranes and wounds causing inconvenience to the user, thereby decreasing treatment compliance.

Polymeric Agent

The composition of the present invention contains a polymeric agent selected from the group consisting of a bioadhesive agent, a gelling agent, a film forming agent and a phase change agent. A polymeric agent enhances the creation of foam having fine bubble structure, which does not readily collapse upon release from the pressurized aerosol can. The polymeric agent serves to stabilize the foam composition and to control drug residence in the target organ.

Exemplary polymeric agents include, in a non-limiting manner, naturally-occurring polymeric materials, such as locust bean gum, sodium alginate, sodium caseinate, egg albumin, gelatin agar, carrageenin gum, sodium alginate, xanthan gum, quince seed extract, tragacanth gum, guar gum, cationic guars, hydroxypropyl guar gum, starch, amine-bearing polymers such as chitosan; acidic polymers obtainable from natural sources, such as alginic acid and hyaluronic acid; chemically modified starches and the like, carboxyvinyl polymers, polyvinylpyrrolidone, polyvinyl alcohol, polyacrylic acid polymers, polymethacrylic acid polymers, polyvinyl acetate polymers, polyvinyl chloride polymers, polyvinylidene chloride polymers and the like.

Additional exemplary polymeric agents include semi-synthetic polymeric materials such as cellulose ethers, such as methylcellulose, hydroxypropyl cellulose, hydroxypropyl methylcellulose, hydroxyethyl cellulose, hydroxy propylmethyl cellulose, methylhydroxyethylcellulose, methylhydroxypropylcellulose, hydroxyethylcarboxymethylcellulose, carboxymethyl cellulose, carboxymethylcellulose carboxymethylhydroxyethylcellulose, and cationic celluloses, carbomer (homopolymer of acrylic acid is crosslinked with an allyl ether pentaerythritol, an allyl ether of sucrose, or an allyl ether of propylene, such as Carbopol® 934, Carbopol® 940, Carbopo® 941, Carbopol® 980 and Carbopol® 981, pemulen and aluminum starch octenylsuccinate (ASOS). Polyethylene glycol, having molecular weight of 1000 or more (e.g., PEG 1,000, PEG 4,000, PEG 6,000 and PEG 10,000) also have gelling capacity and while they are considered herein as "secondary polar solvents", as detailed herein, they are also considered polymeric agents.

In one or more embodiments the polymeric agents have emulsifying properties. In certain preferred embodiments the polymeric agent is a derivatized hydrophilic polymer with hydrophobic alkyl moieties Other types that may also a similar stabilizing effect are silicone copolymers and derivatized starch ASOS.

Mixtures of the above polymeric agents are contemplated.

The concentration of the polymeric agent should be selected so that the composition, after filling into aerosol canisters, is flowable, and can be shaken in the canister. In one or more embodiments, the concentration of the polymeric agent is selected such that the viscosity of the composition, prior to filling of the composition into aerosol canisters, is less than 12,000 CPs, and more preferably, less than 10,000 CPs.

Surface Active Agent

The composition of the present invention further contains a surface-active agent. Surface-active agents (also termed "surfactants") include any agent linking oil and water in the composition, in the form of emulsion. A surfactant's hydrophilic/lipophilic balance (HLB) describes the emulsifier's affinity toward water or oil. HLB is defined for non-ionic surfactants. The HLB scale ranges from 1 (totally lipophilic) to 20 (totally hydrophilic), with 10 representing an equal balance of both characteristics. Lipophilic emulsifiers form water-in-oil (w/o) emulsions; hydrophilic surfactants form oil-in-water (o/w) emulsions. The HLB of a blend of two emulsifiers equals the weight fraction of emulsifier A times its HLB value plus the weight fraction of emulsifier B times its HLB value (weighted average). In many cases a single surfactant may suffice. In other cases a combination of two or more surfactants is desired. Reference to a surfactant in the specification can also apply to a combination of surfactants or a surfactant system. As will be appreciated by a person skilled in the art which surfactant or surfactant system is more appropriate is related to the vehicle and intended purpose. In general terms a combination of surfactants is usually preferable where the vehicle is an emulsion. In an emulsion environment a combination of surfactants can be significant in producing breakable forms of good quality. It has been further discovered that the generally thought considerations for HLB values for selecting a surfactant or sufactant combination are not always binding for emulsions and that good quality foams can be produced with a surfactant or surfactant combination both where the HLB values are in or towards the lipophilic side of the scale and where the HLB values are in or towards the hydrophilic side of the scale. Surfactants also play a role in foam formation where the foamable formulation is a single phase composition.

According to one or more embodiments the composition contains a single surface active agent having an HLB value between about 2 and 9, or more than one surface active agent and the weighted average of their HLB values is between about 2 and about 9. Lower HLB values may in certain embodiments be more applicable to water in oil emulsions.

According to one or more embodiments the composition contains a single surface active agent having an HLB value between about 7 and 14, or more than one surface active agent and the weighted average of their HLB values is between about 7 and about 14. Mid range HLB values may in certain embodiments be more suitable for oil in water emulsions.

According to one or more other embodiments the composition contains a single surface active agent having an HLB value between about 9 and about 19, or more than one surface active agent and the weighted average of their HLB values is between about 9 and about 19. In a waterless or substantially waterless environment a wide range of HLB values may be suitable.

Preferably, the composition of the present invention contains a non-ionic surfactant. Nonlimiting examples of possible non-ionic surfactants include a polysorbate, polyoxyethylene (20) sorbitan monostearate, polyoxyethylene (20) sorbitan monooleate, a polyoxyethylene fatty acid ester, Myrj 45, Myrj 49, Myrj 52 and Myrj 59; a polyoxyethylene alkyl ether, polyoxyethylene cetyl ether, polyoxyethylene palmityl ether, polyethylene oxide hexadecyl ether, polyethylene glycol cetyl ether, steareths such as steareth 2, brij 21, brij 721, brij 38, brij 52, brij 56 and brij W1, a sucrose ester, a partial ester of sorbitol and its anhydrides, sorbitan monolaurate, sorbitan monolaurate, a monoglyceride, a diglyceride, isoceteth-20 and mono-, di- and tri-esters of sucrose with fatty acids. In certain embodiments, suitable sucrose esters include those having high monoester content, which have higher HLB values.

In certain embodiments with DCA esters as emollient, surfactants are selected which can provide a close packed sufacant layer separating the oil and water phases. To achieve such objectives combinations of at least two surfactants are selected. Preferably, they should be complex emulgators and more preferably they should both be of a similar molecular type. For example, a pair of ethers like steareth 2 and steareth 21, or a pair of esters for example, PEG-40 stearate and polysorbate 80. In Certain circumstances POE esters cannot be used and a combination of sorbitan laurate and sorbitan stearate or a combination of sucrose stearic acid ester mixtures and sodium laurate may be used. All these combinations due to heir versatility and strength may also be used satisfactorily and effectively with solutions of DCA's and with solid/crystalline suspensions, although the amounts and proportion may be varied according to the formulation and its objectives as will be appreciated by a man of the art.

It has been discovered also that by using a derivatized hydrophilic polymer with hydrophobic alkyl moieties as a polymeric emulsifier such as pemulen it is possible to stabilize the emulsion better about or at the region of phase reversal tension. Other types of derivatized polymers like silicone copolymers, derivatized starch [Aluminum Starch Octenylsuccinate (ASOS)]/[DRY-FLO AF Starch], and derivatized dexrin may also a similar stabilizing effect.

A series of dextrin derivative surfactants prepared by the reaction of the propylene glycol polyglucosides with a hydrophobic oxirane-containing material of the glycidyl ether are highly biodegradable. [Hong-Rong Wang and Keng-Ming Chen, Colloids and Surfaces A: Physicochemical and Engineering Aspects Volume 281, Issues 1-3, 15 Jun. 2006, Pages 190-193].

Non-limiting examples of non-ionic surfactants that have HLB of about 7 to about 12 include steareth 2 (HLB-4.9); glyceryl monostearate/PEG 100 stearate (Av HLB-11.2); stearate Laureth 4 (HLB-9.7) and cetomacrogol ether (e.g., polyethylene glycol 1000 monocetyl ether).

Non-limiting examples of preferred surfactants, which have a HLB of 4-19 are set out in the Table below:

| Surfactant | HLB |
|---|---|
| steareth 2 | ~4.9 |
| glyceryl monostearate/PEG 100 stearate | Av~11.2 |
| Glyceryl Stearate | ~4 |
| Steareth-21 | ~15.5 |
| peg 40 stearate | ~16.9 |
| polysorbate 80 | ~15 |
| sorbitan stearate | ~4.7 |
| laureth 4 | ~9.7 |
| Sorbitan monooleate (span 80) | ~4.3 |
| ceteareth 20 | ~15.7 |
| steareth 20 | ~15.3 |
| ceteth 20 | ~15.7 |
| Macrogol Cetostearyl Ether | ~15.7 |
| ceteth 2 (Lipocol C-2) | ~5.3 |
| PEG-30 Dipolyhydroxystearate | ~5.5 |
| sucrose distearate (Sisterna SP30) | ~6 |
| polyoxyethylene (100) stearate | ~18.8 |

More exemplary stabilizing surfactants which may be suitable for use in the present invention are found below.

PEG-Fatty Acid Monoester Surfactants

| Chemical name | Product example name | HLB |
| --- | --- | --- |
| PEG-30 stearate | Myrj 51 | >10 |
| PEG-40 laurate | Crodet L40 (Croda) | 17.9 |
| PEG-40 oleate | Crodet O40 (Croda) | 17.4 |
| PEG-45 stearate | Nikkol MYS-45 (Nikko) | 18 |
| PEG-50 stearate | Myrj 53 | >10 |
| PEG-100 stearate | Myrj 59, Arlacel 165 (ICI) | 19 |

PEG-Fatty Acid Diester Surfactants:

| Chemical name | Product example name | HLB |
| --- | --- | --- |
| PEG-4 dilaurate | Mapeg .RTM. 200 DL (PPG), Kessco .RTM.PEG 200 DL (Stepan), LIPOPEG 2-DL (Lipo Chem.) | 7 |
| PEG-4 distearate | Kessco .RTM. 200 DS (Stepan.sub) | 5 |
| PEG-32 dioleate | Kessco .RTM. PEG 1540 DO (Stepan) | 15 |
| PEG-400 dioleate | Cithrol 4DO series (Croda) | >10 |
| PEG-400 disterate | Cithrol 4DS series (Croda) | >10 |
| PEG-20 glyceryl oleate | Tagat .RTM. O (Goldschmidt) | >10 |

Transesterification Products of Oils and Alcohols

| Chemical name | Product example name | HLB |
| --- | --- | --- |
| PEG-30 castor oil | Emalex C-30 (Nihon Emulsion) | 11 |
| PEG-40 hydrogenated castor oil | Cremophor RH 40 (BASF), Croduret (Croda), Emulgin HRE 40 (Henkel) | 13 |

Polyglycerized Fatty Acids, such as:

| Chemical name | Product example name | LB |
| --- | --- | --- |
| Polyglyceryl-6 dioleate | Caprol .RTM. 6G20 (ABITEC); PGO-62 (Calgene), PLUROL OLEIQUE CC 497 (Gattefosse)Hodag | 8.5 |

PEG-Sorbitan Fatty Acid Esters

| Chemical name | Product example name | HLB |
| --- | --- | --- |
| PEG-20 sorbitan monolaurate | Tween-20 (Atlas/ICI), Crillet 1 (Croda), DACOL MLS 20 (Condea) | 17 |
| PEG-20 sorbitan Monopalmitate | Tween 40 (Atlas/ICI), Crillet 2 (Croda) | 16 |
| PEG-20 sorbitan monostearate | Tween-60 (Atlas/ICI), Crillet 3 (Croda) | 15 |
| PEG-20 sorbitan monooleate | Tween-80 (Atlas/ICI), Crillet 4 (Croda) | 15 |

Polyethylene Glycol Alkyl Ethers

| Chemical name | Product example name | HLB |
| --- | --- | --- |
| PEG-2 oleyl ether | oleth-2 Brij 92/93 (Atlas/ICI) | 4.9 |
| PEG-3 oleyl ether | oleth-3 Volpo 3 (Croda) | <10 |
| PEG-5 oleyl ether | oleth-5 Volpo 5 (Croda) | <10 |
| PEG-10 oleyl ether | oleth-10 Volpo 10 (Croda), Brij 96/97 (Atlas/ICI) | 12 |
| PEG-20 oleyl ether | oleth-20 Volpo 20 (Croda), Brij 98/99 (Atlas/ICI) | 15 |
| PEG-4 lauryl ether | laureth-4Brij 30 (Atlas/ICI) | 9.7 |
| PEG-23 lauryl ether | laureth-23Brij 35 (Atlas/ICI) | 17 |
| PEG-10 stearyl ether | Brij 76 (ICI) | 12 |
| PEG-2 cetyl ether | Brij 52 (ICI) | 5.3 |

Sugar Ester Surfactants

| Chemical name | Product example name | HLB |
| --- | --- | --- |
| Sucrose distearate | Sisterna SP50, Surfope 1811 | 11 |

Sorbitan Fatty Acid Ester Surfactants

| Chemical name | Product example name | HLB |
| --- | --- | --- |
| Sorbitan monolaurate | Span-20 (Atlas/ICI), Crill 1 (Croda), Arlacel 20 (ICI) | 8.6 |
| Sorbitan monopalmitate | Span-40 (Atlas/ICI), Crill 2 (Croda), Nikkol SP-10 (Nikko) | 6.7 |
| Sorbitan monooleate | Span-80 (Atlas/ICI), Crill 4 (Croda), Crill 50 (Croda) | 4.3 |
| Sorbitan monostearate | Span-60 (Atlas/ICI), Crill 3 (Croda), Nikkol SS-10 (Nikko) | 4.7 |

In one or more embodiments the surface active agent is a complex emulgator in which the combination of two or more surface active agents can be more effective than a single surfactant and provides a more stable emulsion or improved foam quality than a single surfactant. For example and by way of non-limiting explanation it has been found that by choosing say two surfactants, one hydrophobic and the other hydrophilic the combination can produce a more stable emulsion than a single surfactant. Preferably, the complex emulgator comprises a combination of surfactants wherein there is a difference of about 4 or more units between the HLB values of the two surfactants or there is a significant difference in the chemical nature or structure of the two or more surfactants.

Specific non limiting examples of surfactant systems are, combinations of polyoxyethylene alkyl ethers, such as Brij 59/Brij 10; Brij 52/Brij 10; Steareth 2/Steareth 20; Steareth 2/Steareth 21 (Brij 72/Brij 721); combinations of polyoxyethylene stearates such as Myrj 52/Myrj 59; combinations of sucrose esters, such as Surphope 1816/Surphope 1807; combinations of sorbitan esters, such as Span 20/Span 80; Span 20/Span 60; combinations of sucrose esters and sorbitan esters, such as Surphope 1811 and Span 60; combinations of liquid polysorbate detergents and PEG compounds, such as Tween 80/PEG-40 stearate; methyl glucaso sequistearate; polymeric emulsifiers, such as Permulen (TRI or TR2); liquid crystal systems, such as Arlatone (2121), Stepan (Mild RM1), Nikomulese (41) and Montanov (68) and the like.

In certain embodiments the surfactant is preferably one or more of the following: a combination of steareth-2 and steareth-21 on their own or in combination with glyceryl monostearate (GMS); in certain other embodiments the surfactant is a combination of polysorbate 80 and PEG-40 stearate. In certain other embodiments the surfactant is a combination of glyceryl monostearate/PEG 100 stearate. In certain other embodiments the surfactant is a combination of two or more of stearate 21, PEG 40 stearate, and polysorbate 80. In certain other embodiments the surfactant is a combination of two or more of laureth 4, span 80, and polysorbate 80. In certain other embodiments the surfactant is a combination of two or more of GMS and ceteareth. In certain other embodiments the surfactant is a combination of two or more of steareth 21, ceteareth 20, ceteth 2 and laureth 4 In certain other embodiments the surfactant is a combination of ceteareth 20 and polysorbate 40 stearate. In certain other embodiments the surfactant is a combination of span 60 and GMS.

In certain other embodiments the surfactant is one or more of sucrose stearic acid esters, sorbitan laureth, and sorbitan stearate.

In one or more embodiments the stability of the composition can be improved when a combination of at least one non-ionic surfactant having HLB of less than 9 and at least one non-ionic surfactant having HLB of equal or more than 9 is employed. The ratio between the at least one non-ionic surfactant having HLB of less than 9 and the at least one non-ionic surfactant having HLB of equal or more than 9, is between 1:8 and 8:1, or at a ratio of 4:1 to 1:4. The resultant HLB of such a blend of at least two emulsifiers is preferably between about 9 and about 14.

Thus, in an exemplary embodiment, a combination of at least one non-ionic surfactant having HLB of less than 9 and at least one non-ionic surfactant having HLB of equal or more than 9 is employed, at a ratio of between 1:8 and 8:1, or at a ratio of 4:1 to 1:4, wherein the HLB of the combination of emulsifiers is preferably between about 5 and about 18.

In certain cases, the surface active agent is selected from the group of cationic, zwitterionic, amphoteric and ampholytic surfactants, such as sodium methyl cocoyl taurate, sodium methyl oleoyl taurate, sodium lauryl sulfate, triethanolamine lauryl sulfate and betaines.

Many amphiphilic molecules can show lyotropic liquid-crystalline phase sequences depending on the volume balances between the hydrophilic part and hydrophobic part. These structures are formed through the micro-phase segregation of two Many amphiphilic molecules can show lyotropic liquid-crystalline phase sequences depending on the volume balances between the hydrophilic part and hydrophobic part. These structures are formed through the micro-phase segregation of two incompatible components on a nanometer scale. Soap is an everyday example of a lyotropic liquid crystal. Certain types of surfactants tend to form lyotropic liquid crystals in emulsions interface (oil-in-water) and exert a stabilizing effect In one or more embodiments the surfactant is a surfactant or surfactant combination is capable of or which tends to form liquid crystals. Surfactants which tend to form liquid crystals may improve the quality of foams. Non limiting examples of surfactants with postulated tendency to form interfacial liquid crystals are: phospholipids, alkyl glucosides, sucrose esters, sorbitan esters.

In one or more embodiments the at least one surface active agent is liquid.

In one or more embodiments the at least one surface active agent is solid, semi solid or waxy.

It should be noted that HLB values may not be so applicable to non ionic surfactants, for example, with liquid crystals or with silicones. Also HLB values may be of lesser significance in a waterless or substantially non-aqueous environment.

In one or more embodiments the surfactant can be, a surfactant system comprising of a surfactant and a co surfactant, a waxy emulsifier, a liquid crystal emulsifier, an emulsifier which is solid or semi solid at room temperature and pressure, or combinations of two or more agents in an appropriate proportion as will be appreciated a person skilled in the art. Where a solid or semi solid emulsifier combination is used it can also comprise a solid or semi solid emulsifier and a liquid emulsifier.

In one or more embodiments of the present invention, the surface-active agent includes at least one non-ionic surfactant. Ionic surfactants are known to be irritants. Therefore, non-ionic surfactants are preferred in applications including sensitive tissue such as found in most mucosal tissues, especially when they are infected or inflamed. Non-ionic surfactants alone can provide formulations and foams of good or excellent quality in the carriers and compositions of the present invention.

Thus, in a preferred embodiment, the surface active agent, the composition contains a non-ionic surfactant. In another preferred embodiment the composition includes a mixture of non-ionic surfactants as the sole surface active agent. Yet, in additional embodiments, the foamable composition includes a mixture of at least one non-ionic surfactant and at least one ionic surfactant in a ratio in the range of about 100:1 to 6:1. In one or more embodiments, the non-ionic to ionic surfactant ratio is greater than about 6:1, or greater than about 8:1; or greater than about 14:1, or greater than about 16:1, or greater than about 20:1. In further embodiments, surface active agent comprises a combination of a non-ionic surfactant and an ionic surfactant, at a ratio of between 1:1 and 20:1

In one or more embodiments of the present invention, a combination of a non-ionic surfactant and an ionic surfactant (such as sodium lauryl sulphate and cocamidopropylbetaine) is employed, at a ratio of between 1:1 and 20:1, or at a ratio of 4:1 to 10:1; for example, about 1:1, about 4:1, about 8:1, about 12:1, about 16:1 and about 20:1 or at a ratio of 4:1 to 10:1, for example, about 4:1, about 6:1, about 8:1 and about 10:1.

In selecting a suitable surfactant or combination thereof it should be borne in mind that the upper amount of surfactant that may be used may be limited by the shakability of the composition. If the surfactant is non liquid, it can make the formulation to viscous or solid. This can be particularly significant if the formulation has high molecular weight, e.g., a high molecular weight PEG or polymeric agents or petroleum or if the surfactants are large. Solvents and polymeric agents which have high molecular weight and are very viscous or solid or waxy (e.g., Peg 1500, 2000, etc. or petrolatum) can exacerbate the effect of a waxy or solid surfactant on shakability or flowability In general terms, as the amount of non-liquid surfactant is increased the shakability of the formulation reduces until a limitation point is reached where the formulation becomes non shakable and unsuitable. Thus in one embodiment, an effective amount of surfactant may be used provided the formulation remains shakable. In other certain exceptional embodiments the upper limit may be determined by flowability such as in circumstances where the composition is marginally or apparently non-shakable. The formulation is sufficiently flowable to be able to flow through an actuator valve and be released and still expand to form a good quality foam.

In certain embodiments of the present invention the amount of surfactant or combination of surfactants is between about 0.05% to about 20%; between about 0.05% to about 15%. or between about 0.05% to about 10%. In a preferred embodiment the concentration of surface active agent is between about 0.2% and about 8%. In a more preferred embodiment the concentration of surface active agent is between about 1% and about 6%.

In some embodiments, it is desirable that the surface active agent does not contain a polyoxyethylene (POE) moiety, such as polysorbate surfactants, POE fatty acid esters, and POE alkyl ethers, because the active agent is incompatible with such surface active agents. For example, the active agent pimecrolimus is not stable the presence of POE moieties, yet benefits greatly from the use of dicarboxylic esters as penetration enhancers. In such cases, alternative surface active agents are employed. In an exemplary manner, POE—free surfactants include non-ethoxylated sorbitan esters, such as sorbitan monopalmitate, sorbitan monostearate, sorbitan tristearate, sorbitan monooleate, sorbitan trioleate, sorbitan monolaurate and sorbitan sesquioleate; glycerol fatty acid esters, such as glycerol monostearate and glycerol monooleate; mono-, di- and tri-esters of sucrose with fatty acids (sucrose esters), sucrose stearate, sucrose distearate sucrose palmitate and sucrose laurate; and alkyl polyglycosides, such as lauryl diglucoside.

If the composition as formulated is a substantially non shakable composition it is nevertheless possible as an exception in the scope of the present invention for the formulation to be flowable to a sufficient degree to be able to flow through an actuator valve and be released and still expand to form a good quality foam. This surprising and unusual exception may be due one or more of a number of factors such as the high viscosity, the softness, the lack of crystals, the pseudoplastic or semi pseudo plastic nature of the composition and the dissolution of the propellant into the composition.

In one or more embodiments of the present invention, the surface-active agent includes mono-, di- and tri-esters of sucrose with fatty acids (sucrose esters), prepared from sucrose and esters of fatty acids or by extraction from sucro-glycerides. Suitable sucrose esters include those having high monoester content, which have higher Phase Inversion and Tension Phase inversion is a factor in the preparation and stabilization of emulsions and can be both an aid and a detriment. Phase inversion involves the change of emulsion type from o/w to w/o or vice versa. Prior to phase inversion occurring there is a tension in the emulsion which if destabilized or driven will lead to phase inversion and if controlled or ameliorated or dissipated will result in a more stable emulsion. The occurrence of phase inversion during preparation can be a sign of instability. If controlled, it can result in a finer product but if due to other factors after the emulsion was prepared it can cause problems. Inversion can occur by for example adding calcium chloride to an o/w emulsion stabilized with sodium stearate to form calcium stearate. Inversion can also occur as the product of changes to the phase-volume ratio. For example if a small amount of water is added to surfactant mixed with oil and agitated aw/o emulsion is formed As the amount of water added is gradually increased a point will be reached where the water and emulsifier envelope the oil as small droplets to form an o/w emulsion. The amount of each ingredient including the surfactants will have their part to play in the phenomenon.

Substantially Alcohol-Free

According to one or more embodiments, the foamable composition is substantially alcohol-free, i.e., free of short chain alcohols. Short chain alcohols, having up to 5 carbon atoms in their carbon chain skeleton and one hydroxyl group, such as ethanol, propanol, isopropanol, butaneol, iso-butaneol, t-butaneol and pentanol, are considered less desirable solvents or polar solvents due to their skin-irritating effect. Thus, the composition is substantially alcohol-free and includes less than about 5% final concentration of lower alcohols, preferably less than about 2%, more preferably less than about 1%.

Substantially Non Aqueous

In certain cases, the active agent degrades in the presence of water, and therefore, in such cases the present of water in the composition is not desirable. Thus, in certain preferred embodiments, the composition is substantially non-aqueous. The term "substantially non-aqueous" or "substantially waterless" is intended to indicate that the composition has a water content below about 5%, preferably below about 2%, such as below about 1.5%. In certain other preferred embodiments the composition is non aqueous or waterless.

By non aqueous or waterless is meant that the composition contains no or substantially no, free or unassociated or absorbed water. It will be understood by a person of the art that the waterless solvents and substances miscible with them of the present invention can be hydrophilic and can contain water in an associated or unfree or absorbed form and may absorb water from the atmosphere and the ability to do so is its hygroscopic water capacity. It is intended that essentially non-aqueous formulations are included within its scope such that the formulations may have present a small amount of water. In some embodiments the composition ingredients are pretreated to reduce, remove or eliminate any residual or associated or absorbed water.

Shakability

'Shakability' means that the composition contains some or sufficient flow to allow the composition to be mixed or remixed on shaking. That is, it has fluid or semi fluid properties. In some very limited cases possibly aided by the presence of silicone it may exceptionally be possible to have a foamable composition which is flowable but not apparently shakable.

Breakability

A breakable foam is one that is thermally stable, yet breaks under sheer force.

The breakable foam of the present invention is not "quick breaking", i.e., it does not readily collapse upon exposure to body temperature environment. Sheer-force breakability of the foam is clearly advantageous over thermally induced breakability, since it allows comfortable application and well directed administration to the target area.

Modulating Agent

The term modulating agent is used to describe an agent which can improve the stability of or stabilize a foamable carrier or composition and or an active agent by modulating the effect of a substance or residue present in the carrier or composition.

In one or more embodiments the modulating agent is used in a water in oil or oil in water emulsion. In one or more other embodiments the modulating agent is used in a unique waterless emulsion.

In certain embodiments the substance or residue may for example be acidic or basic and potentially alter pH in an emulsion environment or it may be one or more metal ions which may act as a potential catalyst in an emulsion environment.

In certain other embodiments the substance or residue may for example be acidic or basic and potentially alter an artificial pH in a waterless or substantially non aqueous environment or it may be one or more metal ions which may act as a potential catalyst in a waterless or substantially non aqueous environment.

In one or more embodiments the modulating agent is used to describe an agent which can affect pH in an aqueous solution. The agent can be any of the known buffering systems used in pharmaceutical or cosmetic formulations as would be appreciated by a man of the art. It can also be an organic acid, a carboxylic acid, a fatty acid an amino acid, an aromatic acid, an alpha or beta hydroxyl acid an organic base or a nitrogen containing compound.

In one or more further embodiments the modulating agent is used to describe an agent, which is a chelating or sequestering or complexing agent that is sufficiently soluble or functional in the solvent to enable it to "mop up" or "lock" metal ions.

In an embodiment modulating agent is used to describe an agent which can effect pH in an aqueous solution the term modulating agent more particularly means an acid or base or buffer system or combinations thereof, which is introduced into or is present in and acts to modulate the ionic or polar characteristics and any acidity or basesity balance of an emulsion carrier, composition, foamable carrier or foamable composition or resultant foam of the present invention.

In other embodiments modulating agent is used to describe an agent which can effect pH in an aqueous solution the term modulating agent more particularly means an acid or base or buffer system or combinations thereof, which is introduced into or is present in and acts to modulate the ionic or polar characteristics and any acidity or basesity balance of a waterless or substantially non aqueous carrier, composition, foamable carrier or foamable composition or resultant foam of the present invention.

The substance or residue can be introduced into the formulation from any one or more of the ingredients, some of which themselves may have acidic or basic properties. For example the polymer or solvent may contain basic residues in which case it may be desirable or beneficial to add an acid. Alternatively the surfactant may contain some acid residues in which case the addition of a base may be desirable and beneficial. In some cases more than one ingredient may contain residues which may ameliorate or compound their significance. For example if one ingredient provided weak acid residues and another stronger acid residues the pH in an emulsion environment (or artificial pH in a waterless environment) should be lower. In contrast if one residue was acid and the other basic the net effect in the formulation may be significantly reduced. In some circumstances the active ingredient may favor an acidic pH or more significantly may need to be maintained at a certain acidic pH otherwise it may readily isomerize, chemically react or breakdown, in which case introducing acidic components such as an acidic polymer might be of help. In an embodiment of the present invention sufficient modulating agent is added to achieve a pH in which the active agent is preferably stable. In another embodiment of the present invention sufficient modulating agent is added to achieve an artificial pH in which the active agent is preferably stable.

The terms pH, pKa, and pKb, buffers and the like are used in classical measurements of an aqueous solution. Such measurements are artificial in a waterless environment. Nevertheless, reference to and description below of such terms are made for convenience and clarity, since such terms are well defined and understood with reference to aqueous solutions and further due to the lack of an appropriate uniform way of describing and identifying the artificial or virtual pH, pK etc in a waterless environment in relation to the present invention. Although predictions of artificial pH can be made using dilution techniques of measurements of waterless formulations diluted in water they are formulation sensitive and specific and have to be carefully calibrated with complex formulas.

Waterless medium can be polar and protic yet it does not conform to classical ionic behavior.

A buffer, as defined by Van Slyke [Van Slyke, *J. Biol. Chem.* 52, 525 (1922)], is "a substance which by its presence in solution increases the amount of acid or alkali that must be added to cause unit change in pH."

A buffer solution is a solution of a definite pH made up in such a way that this pH alters only gradually with the addition of alkali or acid. Such a solution consists of a solution of a salt of the week acid in the presence of the three acid itself. The pH of the solution is determined by the dissociation equilibrium of the free acid.

An acid can be a strong acid or a weak acid. A strong acid is an acid, which is a virtually 100% ionized in solution. In contrast, a week acid is one which does not ionize fully. When it is dissolved in water. The lower the value for pKa, the stronger is the acid and likewise, the higher the value for pKa the weaker is the acid.

A base can be a strong base or a weak base. A strong base is something, which is fully ionic with 100% hydroxide ions. In contrast, a weak base is one which does not convert fully into hydroxide ions in solution. The lower the value for pKb, the stronger is the base and likewise, the higher the value for pKb the weaker is the base.

In one or more embodiments of the present invention the modulating agent comprises an organic compound.

In one or more preferred embodiments of the present invention the chelating agent is selected from the group consisting of ethylenediaminetetraacetic acid (EDTA), diethylenetriaminepentaacetic acid (DTPA), hydroxyethyl-enediaminetriacetic acid (HEDTA), nitrilotriacetic acid (NTA), O,O'-bis(2-aminoethyl)ethyleneglycol-N,N,N',N'-tetraacetic acid (EGTA), trans-1,2-diaminocyclohexane-N,N,N',N'-tetraacetic acid (CyDTA) or a pharmaceutically acceptable salt thereof (normally as a sodium salt), more preferably EDTA, HEDTA and their salts; most preferably EDTA and its salts.

In one or more embodiments of the present invention a preferred non limiting example of the chelating agent is EDTA. Typically, the chelating and sequestering agent is present in the composition at a level of up to about 5.0%, preferably 1.0 percent, by weight, of the composition.

In one or more embodiments of the present invention the modulating agent may also be a preservative or an antioxidant or an ionization agent. Any preservative, antioxidant or ionization agents suitable for pharmaceutical or cosmetic application may be used. Non limiting examples of antioxidants are tocopherol succinate, propyl galate, butylated hydroxy toluene and butyl hydroxy anisol. Ionization agents may be positive or may be negative depending on the environment and the active agent or composition that is to be protected. Ionization agents may for example act to protect or reduce sensitivity of active agents. Non limiting examples of positive ionization agents are benzyl conium chloride, and cetyl pyridium chloride. Non limiting examples of negative ionization agents are sodium lauryl sulphate, sodium lauryl lactylate and phospholipids.

Humectant

A humectant is a substance that helps retain moisture and also prevents rapid evaporation. Non limiting examples are propylene glycol, propylene glycol derivatives, glycerin, hydrogenated starch hydrosylate, hydrogenated lanolin, lanolin wax, D manitol, sorbitol, sodium 2-pyrrolidone-5-carboxylate, sodium lactate, sodium PCA, soluble collagen, dibutyl phthalate, and gelatin. Other examples may be found in the Handbook of Pharmaceutical Additives published by Gower.

Moisturizers

A moisturizer, is a substance that helps retain moisture or add back moisture to the skin. Examples are allantoin, petrolatum, urea, lactic acid, sodium PCV, glycerin, shea butter, caprylic/capric/stearic triglyceride, candelilla wax, propylene glycol, lanolin, hydrogenated oils, squalene, sodium hyaluronate and lysine PCA. Other examples may be found in the Handbook of Pharmaceutical Additives published by Gower.

Pharmaceutical compositions of the present invention may in one or more embodiments usefully comprise in addition a heumectant or a moisturizer or combinations thereof.

Polar Solvent

Optionally, the foamable vehicle further includes at least one polar solvent.

A "polar solvent" is an organic solvent, typically soluble in both water and oil. Certain polar solvents, for example propylene glycol and glycerin, possess the beneficial property of a heumectant.

In one or more embodiments, the polar solvent is a heumectant.

In one or more embodiments, the polar solvent is a polyol. Polyols are organic substances that contain at least two hydroxy groups in their molecular structure.

In one or more embodiments, the polar solvent contains an diol (a compound that contains two hydroxy groups in its molecular structure), such as propylene glycol (e.g., 1,2-propylene glycol and 1,3-propylene glycol), butaneediol (e.g., 1,4-butaneediol), butaneediol (e.g., 1,3-butaneediol and 1,4-butenediol), butynediol, pentanediol (e.g., 1,5-pentanediol), hexanediol (e.g., 1,6-hexanediol), octanediol (e.g., 1,8-octanediol), neopentyl glycol, 2-methyl-1,3-propanediol, diethylene glycol, triethylene glycol, tetraethylene glycol, dipropylene glycol and dibutylene glycol.

In one or more embodiments, the polar solvent contains a triol (a compound that contains three hydroxy groups in its molecular structure), such as glycerin and 1,2,6-Hexanetriol.

Other non-limiting examples of polar solvents include pyrrolidones, (such as N-methyl-2-pyrrolidone and 1-methyl-2-pyrrolidinone), dimethyl isosorbide, 1,2,6-hexapetriol, dimethyl sulfoxide (DMSO), ethyl proxitol, dimethylacetamide (DMAc) and alpha hydroxy acids, such as lactic acid and glycolic acid.

According to still other embodiments, the polar solvent is a polyethylene glycol (PEG) or PEG derivative that is liquid at ambient temperature, including PEG200 (MW (molecular weight) about 190-210 kD), PEG300 (MW about 285-315 kD), PEG400 (MW about 380-420 kD), PEG600 (MW about 570-630 kD) and higher MW PEGs such as PEG 4000, PEG 6000 and PEG 10000 and mixtures thereof.

Polar solvents are known to enhance the penetration of active agent into the skin and through the skin, and therefore, their inclusion in the composition of the present invention can be desirable, despite their undesirable skin drying and irritation potential. There is at one level a commonality between the different polar solvents and their penetration enhancement properties. Lower molecular weight alcohols can sometimes be more potent as a solvent, for example by extracting lipids from the skin layers more effectively, which characteristic can adversely affect the skin structure and cause dryness and irritation. Therefore the selection of lower molecular weight alcohols is ideally avoided.

Polar solvents, such as detailed below possess high solubilizing capacity and contribute to the skin penetration of an active agent. Non limiting examples include dimethyl isosorbide polyols, such as glycerol (glycerin), propylene glycol, hexylene glycol, diethylene glycol, propylene glycol n-alkanols, terpenes, di-terpenes, tri-terpenes, limonene, terpene-ol, 1-menthol, dioxolane, ethylene glycol, other glycols, oleyl alcohol, alpha-hydroxy acids, such as lactic acid and glycolic acid, sulfoxides, such as dimethylsulfoxide (DMSO), dimethylformanide, methyl dodecyl sulfoxide, dimethylacetamide, azone (1-dodecylazacycloheptan-2-one), 2-(n-nonyl)-1,3-dioxolane, alkanols, such as dialkylamino acetates, and admixtures thereof. In certain preferred embodiments, the polar solvent is selected from the group consisting of dimethyl isosorbide glycerol (glycerin), propylene glycol, hexylene glycol, terpene-ol, oleyl alcohol, lactic acid and glycolic acid.

Skin Penetration Enhancer

A "skin penetration enhancer", also termed herein "penetration enhancer," is an organic solvent, typically soluble in both water and oil. Examples of penetration enhancer include polyols, such as glycerol (glycerin), propylene glycol, hexylene glycol, diethylene glycol, propylene glycol n-alkanols, terpenes, di-terpenes, tri-terpenes, terpen-ols, limonene, terpene-ol, 1-menthol, dioxolane, ethylene glycol, hexylene glycol, other glycols, sulfoxides, such as dimethylsulfoxide (DMSO), dimethylformanide, methyl dodecyl sulfoxide, dimethylacetamide, dimethylisosorbide, monooleate of ethoxylated glycerides (with 8 to 10 ethylene oxide units), azone (1-dodecylazacycloheptan-2-one), 2-(n-nonyl)-1,3-dioxolane, esters, such as isopropyl myristate/palmitate, ethyl acetate, butyl acetate, methyl proprionate, capric/caprylic triglycerides, octylmyristate, dodecylmyristate; myristyl alcohol, lauryl alcohol, lauric acid, lauryl lactate ketones; amides, such as acetamide oleates such as triolein; various alkanoic acids such as caprylic acid; lactam compounds, such as azone; alkanols, such as dialkylamino acetates, and admixtures thereof.

According to one or more embodiments, the penetration enhancer is a polyethylene glycol (PEG) or PEG derivative that is liquid at ambient temperature Potent Solvent In one or more embodiments of the present invention, the foamable composition includes a potent solvent, in addition to or in place of one of the hydrophobic solvents, polar solvents or emollients of the composition. A potent solvent is a solvent other than mineral oil that solubilizes a specific active agent substantially better than a hydrocarbon solvent such as mineral oil or petrolatum. For example, a potent solvent solubilizes the active agent 5 fold better than a hydrocarbon solvent; or even solubilizes the active agent 10-fold better than a hydrocarbon solvent.

In one or more embodiments of the present invention, the composition includes at least one active agent in a therapeutically effective concentration; and at least one potent solvent in a sufficient amount to substantially solubilize the at least one active agent in the composition. The term "substantially soluble" means that at least 95% of the active agent has been solubilized, i.e., 5% or less of the active agent is present in a solid state. In one or more embodiments, the concentration of the at least one potent solvent is more than about 40% of the at least one solvent of the composition of the present invention; or even more than about 60%.

Non-limiting examples of pairs of active agent and potent solvent include: Betamethasone valerate: Practically insoluble in mineral oil (<0.01%); soluble more than 1% in glycofurol; Hydrocortisone butyrate: Practically insoluble in mineral oil (<0.01%); soluble more than 1% in glycofurol; Metronidazole: Practically insoluble in mineral oil (<0.01%); soluble more than 1% in dimethyl isosrbide; Ketoconazole: Practically insoluble in mineral oil (<0.01%); soluble more than 1% in glycofurol, propylene glycol and dimethyl isosrbide; Mupirocin: Practically insoluble in mineral oil (<0.01%); soluble more than 1% in glycofurol, hexylene glycol, dimethyl isosorbide, propylene glycol and polyethylene glycol 400 (PEG 400); Meloxicam, a non-steroidal anti-inflammatory agent: Practically insoluble in mineral oil (<0.001%); soluble in propylene glycol: 0.3 mg/mL; and in PEG 400: 3.7 mg/mL; and Progesterone: Practically insoluble in mineral oil (<0.001%); soluble in PEG 400: 15.3 mg/mL.

A non-limiting exemplary list of solvents that can be considered as potent solvents includes polyethylene glycol, propylene glycol, hexylene glycol, butaneediols and isomers thereof, glycerol, benzyl alcohol, DMSO, ethyl oleate, ethyl caprylate, diisopropyl adipate, dimethylacetamide, N-methylpyrrolidone, N-hydroxyethylpyrrolidone, polyvinylpyrrolidone, isosorbide derivatives, such as dimethyl isosorbide, glycofurol and ethoxydiglycol (transcutol) and laurocapram.

The use of a potent solvent in a foam composition provides an improved method of delivering poorly soluble therapeutic agents to a target area. It is known that low drug solubility results in poor bioavailability, leading to decreased effectiveness of treatment. Foam compositions of the present invention, for which the solvent includes a potent solvent, increase the levels of the active agent in solution and thus, provide high delivery and improved therapy.

Potent solvents, as defined herein, are usually liquid. Formulations comprising potent solvents and active agents are generally disadvantageous as therapeutics, since their usage involves unwanted dripping and inconvenient method of application; resulting in inadequate dosing. Surprisingly, the foams of the present invention, which are drip-free, provide a superior vehicle for such active agents, enabling convenient usage and accurate effective dosing.

In one or more embodiments of the present invention the present invention the foamable pharmaceutical composition may additionally include a mixture of two or more of the solvents selected from the group of hydrophobic solvents, silicone oils, emollients, polar solvents and potent solvents in an appropriate proportion as would be appreciated to a person skilled in the art.

In one or more embodiments of the present invention, the PPG alkyl ether may act as a potent solvent Additional Components In an embodiment of the present invention, a composition of the present invention includes one or more additional components. Such additional components include but are not limited to anti perspirants, anti-static agents, buffering agents, bulking agents, chelating agents, cleansers, colorants, conditioners, deodorants, diluents, dyes, emollients, fragrances, hair conditioners, humectants, pearlescent aids, perfuming agents, permeation enhancers, pH-adjusting agents, preservatives, protectants, skin penetration enhancers, softeners, solubilizers, sunscreens, sun blocking agents, sunless tanning agents, viscosity modifiers and vitamins. As is known to one skilled in the art, in some instances a specific additional component may have more than one activity, function or effect.

Propellants

Suitable propellants include volatile hydrocarbons such as butane, propane, isobutane and fluorocarbon gases, or mixtures thereof.

The propellant makes up about 5-25 wt % of the foamable composition. The propellants are used to generate and administer the foamable composition as a foam. The total composition including propellant, foamable compositions and optional ingredients is referred to as the foamable composition.

Alcohol and organic solvents render foams inflammable. It has been surprisingly discovered that fluorohydrocarbon propellants, other than chloro-fluoro carbons (CMOs), which are non-ozone-depleting propellants, are particularly useful in the production of a non-flammable foamable composition. A test according to European Standard prEN 14851, titled "Aerosol containers—Aerosol foam flammability test" revealed that compositions containing an organic carrier that contains a hydrophobic organic carrier and/or a polar solvent, which are detected as inflammable when a hydrocarbon propellant is used, become non-flammable, while the propellant is an HFC propellant.

Such propellants include, but are not limited to, hydrofluorocarbon (HFC) propellants, which contain no chlorine atoms, and as such, fall completely outside concerns about stratospheric ozone destruction by chlorofluorocarbons or other chlorinated hydrocarbons. Exemplary non-flammable propellants according to this aspect of the invention include propellants made by DuPont under the registered trademark Dymel, such as 1,1,1,2 tetrafluorethane (Dymel 134), and 1,1,1,2,3,3,3 heptafluoropropane (Dymel 227). HFCs possess Ozone Depletion Potential of 0.00 and thus, they are allowed for use as propellant in aerosol products.

Notably, the stability of foamable emulsions including HFC as the propellant can be improved in comparison with the same composition made with a hydrocarbon propellant.

In one or more embodiments foamable compositions comprise a combination of a HFC and a hydrocarbon propellant such as n-butanee or mixtures of hydrocarbom propellants such as propane, ispbutane and butane.

Microemulsions and Nanoemulsions

Microemulsions and nanoemulsion are monophasic, transparent (or slightly translucent) dispersions of oil and water. Unlike conventional emulsions, microemulsions and nanoemulsion are thermodynamically stable, making them a favorable vehicle for pharmaceutical compositions, which have to maintain stability for long periods of time. They and a method of manufacture are more particularly described in US2006/0233721 which is incorporated herein by way of reference. As will be appreciated by a man of the art the methodology may be adapted according to the type of carrier composition.

Aging

In order to project the potential shelf life and stability of the compositions and their ingredients particularly active or benefit agents the compositions can subjected to a number of tests, including centrifugation to look for resistance to creaming, phase separation; one or more freeze thaw cycles, standing at room and higher temperatures as an indicator of resistance to aging.

Composition and Foam Physical Characteristics and Advantages

A pharmaceutical or cosmetic composition manufactured using the foamable carrier of the present invention is very easy to use. When applied onto the afflicted body surface of mammals, i.e., humans or animals, it is in a foam state, allowing free application without spillage. Upon further application of a mechanical force, e.g., by rubbing the composition onto the body surface, it freely spreads on the surface and is rapidly absorbed.

The foamable composition of the present invention is stable, having an acceptable shelf-life of at least one year, or preferably, at least two years at ambient temperature, as revealed in accelerated stability tests. The foamable compositions according to the present invention are stable. Following accelerated stability studies, they demonstrate desirable texture; they form fine bubble structures that do not break immediately upon contact with a surface, spread easily on the treated area and absorb quickly.

The composition should also be free flowing, to allow it to flow through the aperture of the container, e.g., and aerosol container, and create an acceptable foam.

Foam quality can be graded as follows:

Grade E (excellent): very rich and creamy in appearance, does not show any bubble structure or shows a very fine (small) bubble structure; does not rapidly become dull; upon spreading on the skin, the foam retains the creaminess property and does not appear watery.

Grade G (good): rich and creamy in appearance, very small bubble size, "dulls" more rapidly than an excellent foam, retains creaminess upon spreading on the skin, and does not become watery.

Grade FG (fairly good): a moderate amount of creaminess noticeable, bubble structure is noticeable; upon spreading on the skin the product dulls rapidly and becomes somewhat lower in apparent viscosity.

Grade F (fair): very little creaminess noticeable, larger bubble structure than a "fairly good" foam, upon spreading on the skin it becomes thin in appearance and watery.

Grade P (poor): no creaminess noticeable, large bubble structure, and when spread on the skin it becomes very thin and watery in appearance.

Grade VP (very poor): dry foam, large very dull bubbles, difficult to spread on the skin.

Topically administrable foams are typically of quality grade E or G, when released from the aerosol container. Smaller bubbles are indicative of more stable foam, which does not collapse spontaneously immediately upon discharge from the container. The finer foam structure looks and feels smoother, thus increasing its usability and appeal.

As further aspect of the foam is breakability. The breakable foam is thermally stable, yet breaks under sheer force. Sheer-force breakability of the foam is clearly advantageous over thermally induced breakability. Thermally sensitive foams immediately collapse upon exposure to skin temperature and, therefore, cannot be applied on the hand and afterwards delivered to the afflicted area.

Another property of the foam is specific gravity, as measured upon release from the aerosol can. Typically, foams have specific gravity of less than 0.12 g/mL; or less than 0.10 g/mL; or less than 0.08 g/mL, depending on their composition and on the propellant concentration.

Pharmaceutical Composition

The foamable carrier of the present invention is an ideal vehicle for active pharmaceutical ingredients and active cosmetic ingredients. In the context of the present invention, active pharmaceutical ingredients and active cosmetic ingredients are collectively termed "active agent" or "active agents."

In one or more embodiments, the dicarboxylic acid or dicarboxylic ester is the active ingredient. It can be used in the formulation as a suspended solid or in solution, alone or in combination with other active agents. As is known to one skilled in the art, in some instances a specific active agent may have more than one activity, function or effect.

In one embodiment, the dicarboxylic acid or dicarboxylic acid ester is useful as an antibiotic, an antifungal agent, a keratolytic agent, an inhibitor of the reduction of testosterone to dihydrotestosterone, an inhibitor of the production of sebum in the sebaceous gland, an anti-acne agent, by way of example. Dicarboxylic acids, and azxelaic acid in particular, may be used for the treatment of diaper rash, hyperpigmentary drmatoses, acne, presbyderma of aging skin, hyperhydrosis, ischthyosis, and wrinkling of the skin, anti-tumor agents (for example, in conjunction with vitamins A, E and D), rosacea, a pigmentation disorder, a cell proliferation abnormality a skin infection and a skin inflammation and treatment of corns and callouses due to the anti-keratolytic effects.

In one or more embodiments, the dicarboxylic acid or dicarboxylic ester is used as a solvent for an active agent or as a penetration enhancer for an active agent.

Suitable active agents for use in conjunction with a dicarboxylic acid or a dicarboxylic ester include, but are not limited to, active herbal extracts, acaricides, age spot and keratose removing agents, allergen, analgesics, local anesthetics, antiacne agents, antiallergic agents, antiaging agents, antibacterials, antibiotics, antiburn agents, anticancer agents, antidandruff agents, antidepressants, antidermatitis agents, antiedemics, antihistamines, antihelminths, antihyperkeratolyte agents, antiinflammatory agents, antiirritants, antilipemics, antimicrobials, antimycotics, antiproliferative agents, antioxidants, anti-wrinkle agents, antipruritics, antipsoriatic agents, antirosacea agents antiseborrheic agents, antiseptic, antiswelling agents, antiviral agents, antiyeast agents, astringents, topical cardiovascular agents, chemotherapeutic agents, corticosteroids, dicarboxylic acids, disinfectants, fungicides, hair growth regulators, hormones, hydroxy acids, immunosuppressants, immunoregulating agents, insecticides, insect repellents, keratolytic agents, lactams, metals, metal oxides, mitocides, neuropeptides, non-steroidal anti-inflammatory agents, oxidizing agents, pediculicides, photodynamic therapy agents, retinoids, sanatives, scabicides, self tanning agents, skin whitening agents, vasoconstrictors, vasodilators, vitamins, vitamin D derivatives, wound healing agents and wart removers. As is known to one skilled in the art, in some instances a specific active agent may have more than one activity, function or effect.

In one or more embodiments, the formulation additionally includes a steroidal anti-inflammatory agent. The dicarboxylic acid ester is present in the composition in an amount sufficient to solubilize the steroid. Exemplary steroidal anti-inflammatory agents include, but are not limited to, corticosteroids such as bydrocortisone, hydroxyltriamcinolone, alpha-methyl dexamethasone, dexamethasone-phosphate, beclomethsone dipropionate, clobetasol valemate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortmate, mepreddisone, paramethasone, prednisolone, prednisone, beclomethasone dipropionate, triamcinolone, and mixtures thereof. In an embodiment of the present invention, the dicarboxylic acid ester is present in the composition in an amount sufficient to solubilize the steroid.

In one embodiment, the formulation additionally includes an immunomodulator. The dicarboxylic acid ester is present in the composition in an amount sufficient to solubilize the immunomodulator. Immunomodulators are chemically or biologically-derived agents that modify the immune response or the functioning of the immune system (as by the stimulation of antibody formation or the inhibition of white blood cell activity). Immunomodulators include, among other options, cyclic peptides, such as cyclosporine, tacrolimus, tresperimus, pimecrolimus, sirolimus (rapamycin), verolimus, laflunimus, laquinimod and imiquimod. Such compounds, delivered in the foam of the present invention, are especially advantageous in skin disorders such as psoriasis, eczema and atopic dermatitis, where the large skin areas are to be treated.

In an embodiment of the present invention, the active agent is selected from a dicarboxylic acid and a dicarboxylic acid ester.

Because of the multiple therapeutic properties of dicarboxylic acids and their respective esters, the combination of such dicarboxylic acids or their respective esters with another active agents can result in a synergistic therapeutic benefit. For example, psoriasis is characterized by a heperkeratinization aspect and an inflammation, and therefore, its treatment can benefit from the combination of a dicarboxylic acid, which is keratolytic and a steroid.

Fields of Applications

The foamable carrier of the present invention is suitable for treating any inflicted surface. In one or more embodiments, foamable carrier is suitable for administration to the skin, a body surface, a body cavity or mucosal surface, e.g., the cavity and/or the mucosa of the nose, mouth, eye, ear, respiratory system, vagina or rectum (severally and interchangeably termed herein "target site").

In one embodiment, the disorder is a dermatological disorder, which can be treated by a dicarboxylic acid.

In another embodiment, the disorder is a dermatological disorder that benefits from the use of a dicarboxylic acid or dicarboxylic ester in conjunction with another active agent. The dicarboxylic acid or dicarboxylic ester may benefit by improving the solubility of the active agent or increasing the penetration of the active agent. The dicarboxylic acid or dicarboxylic ester may also provide a synergistic therapeutic effect in combination with the active agent.

By selecting a suitable active agent, or a combination of two or more active agents, the foamable composition of the present invention is useful in treating an animal or a human patient having any one of a variety of dermatological disorders, including dermatological pain, dermatological inflammation, acne, acne vulgaris, inflammatory acne, non-inflammatory acne, acne fulminans, nodular papulopustular acne, acne conglobata, dermatitis, bacterial skin infections, fungal skin infections, viral skin infections, parasitic skin infections, skin neoplasia, skin neoplasms, pruritis, cellulitis, acute lymphangitis, lymphadenitis, erysipelas, cutaneous abscesses, necrotizing subcutaneous infections, scalded skin syndrome, folliculitis, furuncles, hidradenitis suppurativa, carbuncles, paronychial infections, rashes, erythrasma, impetigo, ecthyma, yeast skin infections, warts, molluscum contagiosum, trauma or injury to the skin, post-operative or post-surgical skin conditions, scabies, pediculosis, creeping eruption, eczemas, psoriasis, pityriasis rosea, lichen planus, pityriasis rubra pilaris, edematous, erythema multiforme, erythema nodosum, granuloma annulare, epidermal necrolysis, sunburn, photosensitivity, pemphigus, bullous pemphigoid, dermatitis herpetiformis, keratosis pilaris, callouses, corns, ichthyosis, skin ulcers, ischemic necrosis, miliaria, hyperhidrosis, moles, Kaposi's sarcoma, melanoma, malignant melanoma, basal cell carcinoma, squamous cell carcinoma, poison ivy, poison oak, contact dermatitis, atopic dermatitis, rosacea, purpura, moniliasis, candidiasis, baldness, alopecia, Behcet's syndrome, cholesteatoma, Dercum disease, ectodermal dysplasia, gustatory sweating, nail patella syndrome, lupus, hives, hair loss, Hailey-Hailey disease, chemical or thermal skin burns, scleroderma, aging skin, wrinkles, sun spots, necrotizing fasciitis, necrotizing myositis, gangrene, scarring, and vitiligo.

Likewise, the foamable composition of the present invention is suitable for treating a disorder of a body cavity or mucosal surface, e.g., the mucosa of the nose, mouth, eye, ear, respiratory system, vagina or rectum. Non limiting examples of such conditions include chlamydia infection, gonorrhea infection, hepatitis B, herpes, HIV/AIDS, human papillomavirus (HPV), genital warts, bacterial vaginosis, candidiasis, chancroid, granuloma Inguinale, lymphogranuloma venereum, mucopurulent cervicitis (MPC), molluscum contagiosum, nongonococcal urethritis (NGU), trichomoniasis, vulvar disorders, vulvodynia, vulvar pain, yeast infection, vulvar dystrophy, vulvar intraepithelial neoplasia (VIN), contact dermatitis, pelvic inflammation, endometritis, salpingitis, oophoritis, genital cancer, cancer of the cervix, cancer of the vulva, cancer of the vagina, vaginal dryness, dyspareunia, anal and rectal disease, anal abscess/fistula, anal cancer, anal fissure, anal warts, Crohn's disease, hemorrhoids, anal itch, pruritus ani, fecal incontinence, constipation, polyps of the colon and rectum.

In an embodiment of the present invention, the disorder is a dermatological disorder, which can be treated by a dicarboxylic acid.

In an embodiment of the present invention, the disorder is a dermatological disorder, which can be treated by a dicarboxylic acid ester.

In an embodiment of the present invention, the disorder is a dermatological disorder, which can be treated by a topical steroid, and the dicarboxylic acid or dicarboxylic ester provides a beneficial effect by increasing the solubility or penetration of the topical steroid.

In an embodiment of the present invention, the disorder is a dermatological disorder, which can be treated by an immunomodulator and the dicarboxylic acid or dicarboxylic ester provides a beneficial effect by increasing the solubility or penetration of the topical immunomodulator.

In an embodiment of the present invention, the disorder is a dermatological disorder, which can be treated by an anti-infective agent, such as an antibacterial agent, and antibiotic, an antifungal agent and an antiviral agent, and the dicarboxylic acid or dicarboxylic ester provides a beneficial effect as an anti-infective agent or by increasing the solubility or penetration of the anti-infective agent.

In an embodiment of the present invention, the disorder is a dermatological disorder, which is common in children. Foam is advantageous in the topical treatment of children, who are sensitive to treatment with a cream or ointment.

In an embodiment of the present invention, the disorder is atopic dermatitis and the active agent is a steroid, further including a dicarboxylic acid (DCA) or DCA ester to stabilize or solubilize the topical steroid.

In an embodiment of the present invention, the disorder is psoriasis and the active agent is a steroid, further including a DCA or DCA ester to stabilize or solubilize the topical steroid.

In an embodiment of the present invention, the disorder is selected from psoriasis and atopic dermatitis and the active agent comprises a steroid and an additional non-steroidal active agent, such as a vitamin D derivative, further including a DCA or DCA ester to stabilize or solubilize the topical steroid and/or non-steroidal active agent.

In an embodiment of the present invention, the disorder is selected from psoriasis and atopic dermatitis and the active agent comprises an immunomodulator, further including a DCA or DCA ester to stabilize or solubilize the immunomodulator.

In an embodiment of the present invention, the composition is useful for the treatment of an infection. In one or more embodiments, the composition is suitable for the treatment of an infection, selected from the group of a bacterial infection, a fungal infection, a yeast infection, a viral infection and a parasitic infection.

In an embodiment of the present invention, the composition is useful for the treatment of wound, ulcer and burn.

The composition of the present invention is also suitable for administering a hormone to the skin or to a mucosal membrane or to a body cavity, in order to deliver the hormone into the tissue of the target organ, in any disorder that responds to treatment with a hormone.

Other foamable compositions are described in: U.S. Publication No. 05-0232869, published on Oct. 20, 2005, entitled NONSTEROIDAL IMMUNOMODULATING KIT AND COMPOSITION AND USES THEREOF; U.S. Publication No. 05-0205086, published on Sep. 22, 2005, entitled RETINOID IMMUNOMODULATING KIT AND COMPOSITION AND USES THEREOF; U.S. Publication No. 06-0018937, published on Jan. 26, 2006, entitled STEROID KIT AND FOAMABLE COMPOSITION AND USES THEREOF; U.S. Publication No. 05-0271596, published on Dec. 8, 2005, entitled VASOACTIVE KIT AND COMPOSITION AND USES THEREOF; U.S. Publication No. 06-0269485, published on Nov. 30, 2006, entitled ANTIBIOTIC KIT AND COMPOSITION AND USES THEREOF; U.S. Publication No. 07-0020304, published on Jan. 25, 2007, entitled NON-FLAMMABLE INSECTICIDE COMPOSITION AND USES THEREOF; U.S. Publication No. 06-0193789, published on Aug. 31, 2006, entitled FILM FORMING FOAMABLE COMPOSITION; U.S. patent application Ser. No. 11/732,547, filed on Apr. 4, 2007, entitled ANTI-INFECTION AUGMENTATION OF FOAMABLE COMPOSITIONS AND KIT AND USES THEREOF; U.S. Provisional Patent Application No. 60/789,186, filed on Apr. 4, 2006, KERATOLYTIC ANTIFUNGAL FOAM; U.S. Provisional Patent Application No. 0/815948, filed on Jun. 23, 2006, entitled FOAMABLE COMPOSITIONS COMPRISING A CALCIUM CHANNEL BLOCKER, A CHOLINERGIC AGENT AND A NITRIC OXIDE DONOR; U.S. Provisional Patent Application No. 60/818,634, filed on Jul. 5, 2006, entitled DICARBOXYLIC ACID FOAMABLE VEHICLE AND PHARMACEUTICAL COMPOSITIONS THEREOF; U.S. Provisional Patent Application No. 60/843,140, filed on Sep. 8, 2006, entitled FOAMABLE VEHICLE AND VITAMIN PHARMACEUTICAL COMPOSITIONS THEREOF, all of which are incorporated herein by reference in their entirety. More particularly any of the active ingredients; the solvents; the surfactants; foam adjuvants; penetration enhancers; humectants; moisturizers; and other excipients as well as the propellants listed therein can be applied herein and are incorporated by reference.

The following examples further exemplify the benefit agent foamable pharmaceutical carriers, pharmaceutical compositions thereof, methods for preparing the same, and therapeutic uses of the compositions. The examples are for the purposes of illustration only and are not intended to be limiting of the invention. Many variations may be carried out by one of ordinary skill in the art and are contemplated within the full scope of the present invention.

Methodology

A general procedure for preparing foamable compositions is set out in WO 2004/037225, which is incorporated herein by reference.

Emulsion Foam

1. Mix oily phase ingredients and heat to 75° C. to melt all ingredients and obtain homogeneous mixture.
2. Mix polymers in water with heating or cooling as appropriate for specific polymer.
3. Add all other water soluble ingredients to water-polymer solution and heat to 75° C.
4. Add slowly internal phase to external phase at 75° C. under vigorous mixing and homogenize to obtain fine emulsion. Alternatively the external phase is added slowly to the internal phase.
5. Cool to below 40° C. and add sensitive ingredients with mild mixing.
6. Cool to room temperature.

Waterless Foam

1. Dissolve the polymers in the main solvent with heating or cooling as appropriate for specific polymer. Add the all other ingredients and heat to 75° C. to melt and dissolve the various ingredients.
2. Cool to below 40° C. and add sensitive ingredients with mild mixing.
3. Cool to room temperature.

Oily Waterless Foam

1. Mix all ingredients excluding polymers and heat to 75° C. to melt and dissolve and obtain homogeneous mixture.
2. Mix well and cool to below 40° C. and add the polymers and sensitive ingredients with moderate mixing.
3. Cool to room temperature.

Oily Foam with Phospholipids and/or Water

1. Swell the phospholipids in the main oily solvent under mixing for at least 20 minutes until uniform suspension is obtained.
2. Add all other ingredients excluding polymers and heat to 75° C. to melt and dissolve and obtain homogeneous mixture.
3. Mix well and cool to below 40° C. and add the polymers and sensitive ingredients with moderate mixing.
4. Cool to room temperature.
5. In case of polymers dissolved in water or organic solvent, dissolve the polymers in the solvent with heating or cooling as appropriate for specific polymer and add to the oily mixture under vigorous mixing at ~40° C.

Canisters Filling and Crimping
Each aerosol canister is filled with PFF and crimped with valve using vacuum crimping machine.
Pressurizing
Propellant Filling
Pressurizing is carried out using a hydrocarbon gas or gas mixture
Canisters are filled and then warmed for 30 sec in a warm bath at 50° C. and well shaken immediately thereafter.
Closure Integrity Test.
Each pressurized canister is subjected to bubble and crimping integrity testing by immersing the canister in a 60° C. water bath for 2 minutes. Canisters are observed for leakage as determined by the generation of bubbles. Canisters releasing bubbles are rejected.
Tests
By way of non limiting example the objectives of hardness, collapse time and FTC stability tests are briefly set out below as would be appreciated by a person of the art.
Hardness
LFRA100 instrument is used to characterize hardness. A probe is inserted into the test material. The resistance of the material to compression is measured by a calibrated load cell and reported in units of grams on the texture analyzer instrument display. Preferably at least three repeat tests are made. The textural characteristics of a dispensed foam can effect the degree of dermal penetration, efficacy, spreadability and acceptability to the user. The results can also be looked at as an indicator of softness. Note: the foam sample is dispensed into an aluminum sample holder and filled to the top of the holder.
Collapse Time
Collapse time (CT) is examined by dispensing a given quantity of foam and photographing sequentially its appearance with time during incubation at 36° C. It is useful for evaluating foam products, which maintain structural stability at skin temperature for at least 1 min.
Viscosity
Viscosity is measured with Brookfield LVDV-II+PRO with spindle SC4-25 at ambient temperature and 10, 5 and 1 RPM. Viscosity is usually measured at 10 RPM. However, at about the apparent upper limit for the spindle of ~>50,000 CP, the viscosity at 1 RPM may be measured, although the figures are of a higher magnitude.

2. Procedure
  2.1. Following preparation of the experimental formulation/s, allow to stand at room temperature for ≥24 h.
  2.2. Handle pentane in the chemical hood. Add to each experimental formulation in a 20-mL glass vial a quantity of pentane equivalent to the specified quantity of propellant for that formulation, mix and allow formulation to stand for at least 1 h and not more than 24 h.
  2.3. Transfer each mixture to 1.5 mL microtubes. Tap each microtube on the table surface to remove entrapped air bubbles.
  2.4. Place visually balanced microtubes in the centrifuge rotor and operate the centrifuge at 3,000 rpm for 10 min or at 1,000 rpm for 10 min.
Intra-Canister Uniformity
  1. Representative product containers are collected, sample test solutions are prepared and the content of the analyte is determined according to standard methods in the art. Variability of content is characterized as percent difference or relative standard deviation, as appropriate, according to the number of samples evaluated.
  2. The results ascertain variability or uniformity within a given container in content of analytes (primarily active pharmaceutical ingredients, but also preservatives) taken from different parts of a pressurized canister drug products
  3. Two full canisters were shaken according to product instructions. About 1-3 g of Foam was dispensed from each canister and discarded. Foam sufficient for two replicate sample solution preparations was then dispensed into a glass beaker. This represents the initial sample. A middle portion is then dispensed from each canister being about half the canister contents. This middle dispensed portion may be discarded or collected for testing purposes, as necessary. Foam sufficient for two replicate sample solution preparations was then dispensed into a glass beaker. This represents the final sample. A small amount of formulation remains in the canister. The foam samples were stirred to remove gas/air bubbles. From both the initial and final foam portions from each canister 4 separate sample solutions are prepared and analyzed, 2 from the initial portion and 2 from the final portion. The percent difference is calculated as follows:

$$\frac{\text{Difference between content determined in initial \& final portions}}{\text{Mean of content of initial \& final portions}} \times 100$$

FTC (Freeze Thaw Cycles)
To check the foam appearance under extreme conditions of repeated cycles of cooling, heating, (first cycle) cooling, heating (second cycle) etc., commencing with −100° C. (24 hours) followed by +400° C. (24 hours) measuring the appearance and again repeating the cycle for up to three times.
Creaming by Centrifugation:
1. Principle of test
  The centrifugation used in this procedure serves as a stress condition simulating the aging of the liquid dispersion under investigation. Under these conditions, the centrifugal force applied facilitates the coalescence of dispersed globules or sedimentation of dispersed solids, resulting in loss of the desired properties of the formulated dispersion.
and the intra canister uniformity evaluated from the results.
Stock Compositions
Non-limiting examples of how stock solutions are made up with and without API. Other stock solutions may be made using the same methodology by simply varying adding or omitting ingredients as would be appreciated by one of the ordinary skills in the art.

EXAMPLES

The invention is described with reference to the following examples. This invention is not limited to these examples and experiments. Many variations will suggest themselves and are within the full intended scope of the appended claims.

Section A—Aqueous

A1—Emollient Formulations

A1—Example 1—Vehicle Composition Containing Diisopropyl Adipate (DISPA)

The following foamable vehicles were prepared and the quality of the resultant foam was ascertained.

| PHASE | Ingredient | GOG 08 % w/w | GOG 09 % w/w | GOG 10 % w/w | GOG 11 % w/w |
|---|---|---|---|---|---|
| Oil Phase (A) | Capric/caprylic triglyceride | | | 10.00 | 10.00 |
| | Diisopropyladipate (DISPA) | 20.00 | 20.00 | 20.00 | 20.00 |
| | Benzyl alcohol | 2.00 | 2.00 | 2.00 | 2.00 |
| | Oleyl alcohol | 20.00 | 20.00 | 10.00 | 10.00 |
| | PPG 15 stearyl ether | 2.00 | 2.00 | 2.00 | 2.00 |
| | Sorbitan laurate | | | | 1.50 |
| | Sorbitan stearate | 4.00 | 4.00 | 2.00 | 2.00 |
| | Stearic acid | 4.00 | 4.00 | 2.00 | |
| | Stearyl alcohol | | | | 3.00 |
| | Pemulen TR2 | 0.05 | | 0.05 | |
| Water Phase (B) | Hydroxypropyl methyl cellulose | | | | 0.15 |
| | Xanthan gum | | | | 0.15 |
| | Sucrose ester | 2.00 | 2.00 | 1.00 | 2.00 |
| | Propylene glycol | 8.00 | 8.00 | 8.00 | 8.00 |
| | Glycerin | 5.00 | 5.00 | 5.00 | 8.00 |
| | TEA | 0.10 | 0.10 | 0.10 | |
| | Water | 37.85 | 32.90 | 37.85 | 31.20 |
| | Foam quality | E | E | G | E |
| | Emulsion stability (10000 RPM) | Stable | Stable | Stable | Stable |

Notes:
Compositions GOG 08 and GOG 09 contain 20% DISPA and 20% oleyl alcohol to provide (1) high emolliency; (2) high solubilizing capacity of an oil-soluble active agent; and (3) enhanced skin delivery of an active agent.
Compositions GOG 10 and GOG 11 contain 20% DISPA, 20% oleyl alcohol and 10% capric/caprylic triglyceride to provide (1) enhanced emolliency; (2) high solubilizing capacity of an oil-soluble active agent; and (3) enhanced skin delivery of an active agent.
The compositions contain about 30% water. Therefore, they provide high skin barrier build-up effect.
The compositions are oil in water emulsions, despite the fact that there is oil more than water in the formulation. Oil in water emulsion is maintained and stabiized by selecting a surfactant that favors oil in water emulsions over water in oil emulsions. Hence, the skin feeling of the composition is favorable.
The surfactants, sorbitan laurate, sorbitan stearate and sucrose esters, are POE-free and hence this formulation may be used with active agents that are not compatible with POE.
The compositions can be used as lotions for topical therapy of an inflammatory skin diorder.
In order to create a foamable composition, the composition is filled into an aerosol canister and pressurized using a liquefied or gas propellant can be added at a concentration of about 3% to about 25%.

A1—Example 2—Vehicle Composition Containing Diisopropyl Adipate (DISPA)

The following foamable vehicles were prepared and the quality of the resultant foam was ascertained.

| PHASE | Ingredient | GOG 13 % w/w | GOG 14 % w/w | GOG 15 % w/w |
|---|---|---|---|---|
| Oil Phase (A) | Capric/caprylic triglyceride | 10.00 | 10.00 | 10.00 |
| | Diisopropyladipate | 20.00 | | |
| | Dimethyl sebacate | | 20.00 | |
| | Dioctyl malate | | | 20.00 |
| | Benzyl alcohol | 2.00 | 2.00 | 2.00 |
| | Oleyl alcohol | 10.00 | 10.00 | 10.00 |
| | PPG 15 stearyl ether | 2.00 | 2.00 | 2.00 |
| | Sorbitan laurate | | 2.00 | 2.00 |
| | Sorbitan stearate | 2.00 | | |
| | Stearic acid | | | 1.20 |
| | Stearyl alcohol | 3.00 | 1.00 | |
| Water Phase (B) | Hydroxypropyl methyl cellulose | 0.15 | 0.15 | 0.15 |
| | Xanthan gum | 0.15 | 0.15 | 0.15 |
| | Sucrose ester HLB 16 | | | |
| | Sucrose ester HLB 11 | 3.00 | 2.00 | 2.00 |
| | Propylene glycol | 17.70 | 17.70 | 17.70 |
| | Glycerin | | | |
| | TEA | | | 0.06 |
| | Water | 30.00 | 33.00 | 32.74 |
| | Foam quality | E | G | E |
| | Emulsion stability (10000 RPM) | Stable | Stable | Stable |

Notes:
Composition GOG 13 contains 20% DISPA, 10% oleyl alcohol and 10% capric/caprylic triglyceride, to provide (1) enhanced emolliency; (2) high solubilizing capacity of an oil-soluble active agent; and (3) enhanced skin delivery of an active agent.
Composition GOG 14 contains 20% dietthyl sebacate, 10% oleyl alcohol and 10% capric/caprylic triglyceride, to provide (1) enhanced emolliency; (2) high solubilizing capacity of an oil-soluble active agent; and (3) enhanced skin delivery of an active agent.
Composition GOG 15 contains 20% dioctyl malate, 10% oleyl alcohol and 10% capric/caprylic triglyceride, to provide (1) enhanced emolliency; (2) high solubilizing capacity of an oil-soluble active agent; and (3) enhanced skin delivery of an active agent.
The compositions contain about 30% water. Therefore, they provide high skin barrier build-up effect
The compositions are oil in water emulsions, despite the fact that there is oil more than water in the formulation. Hence, the skin feeling of the composition is favorable.
The surfactants are POE-free: sorbitan laurate, sorbitan stearate and sucrose esters.
The compositions can be used as lotions for topical therapy of an inflammatory skin diorder.
In order to create a foamable composition, the composition is filled into an aerosol canister and pressurized using a liquefied or gas propellant can be added at a concentration of about 3% to about 25%.

A1—Example 3—Vehicle Compositions Containing 10% to 50% Diisopropyl Adipate (DISPA) as Solvent The following foamable vehicles were prepared and the quality of the resultant foam was ascertained.

|  | DCA001 | DCA002 | DCA003 | DCA011 |
|---|---|---|---|---|
| diisopropyl adipate (DISPA) | 10.00 | 20.00 | 30.00 | 40.00 |
| Steareth 2 | 3.06 | 3.67 | 4.89 | 4.89 |
| Steareth 21 | 1.94 | 2.33 | 3.11 | 3.11 |
| Carboxy methyl cellulose | 0.50 | 0.50 | 0.50 | 0.50 |
| Water purified | 84.50 | 73.50 | 61.50 | 51.50 |
| Total | 100.00 | 100.00 | 100.00 | 100.00 |
| Propellant propane, isobutene and butane mixture | 8.00 | 8.00 | 8.00 | 8.00 |
| Appearance: |  |  |  |  |
| foam quality | E | E | E | E |
| color | White | White | White | White |
| odor | No odor | No odor | No odor | No odor |
| density | 0.049 | 0.045 | 0.064 |  |
| collapse time |  | >300 | >300 |  |
| Hardness |  | 18.76 | 31.77 |  |

Excellent foam formulations were prepared with DISPA, surfactant, and a nominal amount of polymeric agent.

In foamable compositions using less than 40 wt % DISPA, no solvent other than water is required to make foamable composition with resultant excellent foams. The use of a combination of ether-based or ester-based surfactants was found to be useful in forming excellent foams with a minimal number of ingredients. Without being bound by any particular theory or mode of operation, it is believed that the use of non-ionic surfactants with significant hydrophobic and hydrophilic components, increase the emulsifier or foam stabilization characteristics of the composition. Similarly, without being bound by any particular theory or mode of operation, using combinations of surfactants with high and low HLB's to provide a relatively close packed surfactant layer may strengthen the emulsion.

Visual test after addition of water indicated that DCA011 is an oil in water emulsion.

A1—Example 4—Minimal Vehicle Compositions, Containing 40% Diisopropyl Adipate (DISPA) with and without Polymer The following foamable vehicles were prepared and the quality of the resultant foam was ascertained.

|  | DCA011 | DCA011A |
|---|---|---|
| diisopropyl adipate (DISPA) | 40.00 | 40.00 |
| Steareth 2 | 4.89 | 4.89 |
| Steareth 21 | 3.11 | 3.11 |
| Carboxy methyl cellulose | 0.50 |  |
| Water purified | 51.50 | 52.00 |
| Total | 100.00 | 100.00 |
| Propellant propane, isobutene and butane mixture | 8.00 | 8.00 |
| Appearance: |  |  |
| foam quality | E | E |
| color | White | White |
| odor | No odor | No odor |

Polymeric agents are introduced to improve foam. Surprisingly, it was possible to prepare excellent foam formulations without a polymeric agent from DISPA, surfactant, and water (and without a foam adjuvant or another solvent). This is especially surprising as the use of water in the composition is understood to benefit from the use of a polymeric agent that can thicken or increase the viscosity of the compositions and improve the resultant foam strength.

As in Example 3 and in Example 6, the combination of ether-based or ester-based surfactants was found to be useful in forming excellent foams with a minimal number of ingredients.

A1—Example 5—Vehicle Compositions Containing about 50% Diisopropyl Adipate (DISPA) with Polymer The following foamable vehicles were prepared and the quality of the resultant foam was ascertained.

|  | DCA012 | DCA013 |
|---|---|---|
| diisopropyl adipate (DISPA) | 46.00 | 50.00 |
| Steareth 2 | 4.58 |  |
| Steareth 21 | 2.92 |  |
| Isoceteth 20 |  | 3.00 |
| Pemulen TR2 |  | 0.22 |
| TEA |  | 0.12 |
| Carboxy methyl cellulose | 0.50 |  |
| Water purified | 46.00 | 46.66 |
| Total | 100.00 | 100.00 |
| Propellant propane, isobutene and butane mixture | 8.00 | 8.00 |
| Appearance: |  |  |
| foam quality | E | E |
| color | White | White |
| odor | No odor | No odor |

Increasing the amount of DISPA above 46% resulted in a poor foam and precipitation in formulations containing a polymer. Changing the surfactant to GMS eliminated the precipitation but the foam remained poor. Replacing the carboxy methyl cellulose polymeric agent with carbopol did not result in any improvement.

Surprisingly, removal of the polymer at 50% DISPA, and steareth 21 and steareth 2 improved the foam quality but did not eliminate the precipitation.

However, by changing the surfactants and polymeric agents it was possible to increase the level of the DISPA and achieve excellent foams without precipitation.

A combination of ether-based or ester-based surfactants was found to be useful in forming excellent foams with a minimal number of ingredients It has been discovered also that by using a derivatized hydrophilic polymer with hydrophobic alkyl moieties as a polymeric emulsifier it is possible to stabilize the emulsion better about or at the region of phase reversal tension. Other types of derivatized polymers like silicone copolymers, derivatized starch and derivatized dexrin may also a similar stabilizing effect.

A1—Example 6—Vehicle Compositions Containing 60% Diisopropyl Adipate (DISPA) without Polymer The following foamable vehicles were prepared and the quality of the resultant foam was ascertained.

|  | DCA028 | DCA029 | DCA030 | DCA031 |
|---|---|---|---|---|
| diisopropyl adipate |  | 60.00 |  | 60.00 |
| diethyl sebacate | 60.00 |  | 60.00 |  |
| Steareth 2 |  |  | 3.00 | 3.00 |
| Steareth 21 |  |  | 2.00 | 2.00 |
| PEG-40 Stearate | 4.00 | 4.00 |  |  |
| Polysorbate 80 | 2.00 | 2.00 |  |  |
| Water purified | 34.00 | 34.00 | 35.00 | 35.00 |
| Total | 100.00 | 100.00 | 100.00 | 100.00 |
| Propellant (1681) | 8.00 | 8.00 | 8.00 | 8.00 |
| Appearance: |  |  |  |  |
| foam quality | E | E | E | E |
| color | White | White | White | White |
| odor | No odor | No odor | No odor | No odor |
| 1000 rpm for 10 mins | stable | stable | stable | stable |
| 3000 rpm for 10 mins | 80% | 80% | stable | 75% |
| % creaming |  |  |  |  |

DCA 028-80% Creaming, 029-80% Creaming, 030-Homogenous, 031-75% Creaming at 3K.

More surprisingly, by removal of the polymer and by reducing the levels of steareth 21 and steareth 2 (ethers) (by about 40 to 50%) it was possible to obtain excellent foams without precipitation at 60% DISPA and at 60% diethyl sebacate.

Without being bound to any particular theory the physical change in the formulation may be due to DISPA reaching a concentration where phase reversal from o/w to w/o emulsion is possible. Also at this concentration range of DISPA removal of the polymeric agent, which itself can absorb water may—without being bound by any theory—have resulted in additional water being available and perhaps reducing internal emulsion tensions including any resulting from the presence of the polymeric agent and thereby unexpectedly resulting in improved foam quality even though polymeric agents are normally added to strengthen foam quality. Also as the concentration of DISPA increased and consequently the amount of water decreased it appears that the amount of surfactant required reduction as the external water phase is thinner.

It has also been discovered by using a different surfactant (ester based in place of an ether based) system it was possible to achieve compositions that can generate good quality foam and without precipitation with 60% DISPA or 60% diethyl sebacate in the absence of polymer. Addition of small amounts of xantham gum and methocel with 60% DISPA and the ester based surfactants resulted in poor foam.

It further appears to be the case that—without being limited by any theory—for any given emulsion system as the oil phase is increased with a corresponding decrease in the water phase the internal tension or pressure for phase reversal will increase and the point at which the phase reversal can occur can be retarded by selective use of non traditional derivatized polymeric agents with emulsifying properties, such as permulen that can stabilize the formulation and push back the point at which pressure for phase reversal might otherwise occur.

Surprisingly it was observed that more traditional polymeric agents like carboxy methyl cellulose or carbopol or combinations like xantham gum and methocel can interfere with foam formulation at higher levels of dicarboxylic esters—all these formulations were examined by conductivity, by water addition test and by microscopic examination and were found to be oil in water emulsions despite the fact that the amount of oil phase was approximately double that of the aqueous phase.

A1—Example 7—Vehicle Compositions Containing 10% to 45% Diethyl Sebacate

The following foamable vehicles were prepared and the quality of the resultant foam was ascertained.

|  | DCA004 | DCA005 | DCA006 | DCA024 | DCA025 |
|---|---|---|---|---|---|
| diethyl sebacate | 10.00 | 20.00 | 30.00 | 40.00 | 45.00 |
| Steareth 2 | 4.00 | 5.00 | 5.33 | 6.00 | 6.00 |
| Steareth 21 | 2.00 | 2.50 | 2.67 | 3.00 | 3.00 |
| Carboxy methyl cellulose | 0.50 | 0.50 | 0.50 | 0.50 | 0.50 |
| Water purified | 83.50 | 72.00 | 61.50 | 50.50 | 45.50 |
| Total | 100.00 | 100.00 | 100.00 | 100.00 | 100.00 |
| Propellant (1681) | 8.00 | 8.00 | 8.00 | 8.00 | 8.00 |
| Appearance: |  |  |  |  |  |
| foam quality | E | E | E | E | E |
| color | White | White | White | White | White |
| odor | No odor | No odor | No odor | No odor | No odor |
| density |  | 0.065 | 0.063 | 0.063 |  |
| collapse time |  | >300 | >300 | >300 |  |
| Hardness |  | 17.23 | 24.67 | 27.39 |  |

Excellent foam formulations were prepared with diethyl sebacate, surfactant, a nominal amount of polymeric agent and water (and without any foam adjuvant or another solvent).

A1—Example 8—DISPA Formulation to Provide Stable Environment for Pimecrolimus

Part 1—Composition of Placebo or Stock Formulation PIMF-001P

| Material | % w/w |
|---|---|
| Caprylic/capric triglyceride | 10.00 |
| Diisopropyl adipate (DISPA) | 20.00 |
| Oleyl alcohol | 10.00 |
| PPG-15 stearyl ether | 2.00 |
| Stearic acid | 1.20 |
| Sorbitan laurate | 2.00 |
| Benzyl alcohol | 2.00 |
| Methocel A4M (methylcellulose) | 0.15 |
| Xanthan gum | 0.15 |

-continued

| Material | % w/w |
|---|---|
| Sucrose stearic acid esters, mixture | 2.00 |
| Propylene glycol | 17.70 |
| Water purified | 32.74 |
| Trolamine (TEA) | 0.06 |
| Total | 100.00 |
| Propellant | 8.00 |

Pimecrolimus is sensitive to polyethylene glycol polymers so it was necessary to develop formulations with emulsifying agents other than for example Twin, Myrj, or Brij surfactants, which are mainstream surfactants for pharmaceutical formulations. The combination of sorbitan laurate with sucrose stearic acid esters was found to be effective. Pimecrolimus is insoluble in water but is soluble in DISPA.

Part 2—Pimecrolimus Content Determined by HPLC in PFF and Foam Formulation

Samples at Various Times and Storage Conditions

The formulations were comprised of 98.8%; 98.6% and 98.4% stock plus 1.2%, 1.4% and 1.6% pimecrolimus respectively.

| Sample name | | Zero time | 14 days, 50° C., glass vials, PFF | 30 days, 40° C., Foam | 30 days, 50° C. glass vials, PFF | 30 days, 50° C. canisters PFF |
|---|---|---|---|---|---|---|
| PIM 1.2%: | Result 1 | 1.12 | 1.14 | 1.22 | 1.05 | 1.13 |
| batch PIMF001-060620 | Result 2 | 1.12 | 1.13 | 1.22 | 1.05 | 1.13 |
| | Average | 1.12 | 1.14 | 1.22 | 1.05 | 1.13 |
| PIM 1.4%: | Result 1 | 1.45 | 1.31 | 1.41 | 1.39 | 1.37 |
| batch PIMF002-060620 | Result 2 | 1.41 | 1.33 | 1.41 | 1.39 | 1.37 |
| | Average | 1.41 | 1.32 | 1.41 | 1.39 | 1.37 |
| PIM 1.6%: | Result 1 | 1.58 | 1.5 | 1.59 | 1.56 | 1.55 |
| batch PIMF003-060620 | Result 2 | 1.58 | 1.5 | 1.59 | 1.56 | 1.56 |
| | Average | 1.58 | 1.5 | 1.59 | 1.56 | 1.56 |

As can be seen from the above there is no significant breakdown of the active agent after a month when solubilized in DISPA.

Part 3—Physical Properties of PFF and Foam Preparations

| | PFF | | | | |
|---|---|---|---|---|---|
| Formula Name | Centrifugation, 3000 rpm | Centrifugation, 10,000 rpm | Foam Appearance | | |
| | | | Quality | Color | Odor |
| PIMF001 | stable | 80% creaming | good | white | no odor |
| PIMF002 | stable | stable | good | white | no odor |
| PIMF003 | stable | 95% creaming | excellent | white | no odor |

The basic formulation is a liquid emulsion which is inherently not stable with a tendency to cream or separate. Two contradictory forces had to be overcome to produce a good to excellent stable foam. One is to have a liquid formulation that stabilizes the active agent and the other is to have a thick almost solid like constitution which resists or retards creaming and or separation. Nevertheless, by introducing into the formulation a mixture of non-poly ethylene glycol polymer surfactants, which can produce a strong and closed packed barrier between the oil and the water that stabilizes the emulsion, together with polymeric agents that retard creaming and or separation whilst maintaining a fluid constitution, it was possible to stabilize the foam and active agent.

Microscopic examination disclosed that there were no crystals and that Pimecrolimus was solubilized.

A2—Suspensions

A2—Example 9—Dicarboxylic Acid Composition

The following foamable vehicles were prepared and the quality of the resultant foam was ascertained.

Part A—Formulation

| Ingredient | % w/w |
|---|---|
| Azelaic Acid | 15.00 |
| Water | 51.90 |
| Caprylic/Capric triglyceride | 10.87 |
| Propylene glycol | 10.87 |
| Dimethyl isosorbide | 5.44 |
| PEG-40 stearate | 2.83 |
| Cetostearyl alcohol | 1.09 |
| Polysorbate 80 | 0.98 |
| Glyceryl stearate | 0.54 |
| Xanthan gum | 0.27 |
| Methylcellulose A4M | 0.11 |
| Benzoic acid | 0.10 |
| NaOH (18% Solution) | to pH = 4.5 |
| Total: | 100 |

Notes

The composition contains azelaic acid as a benefit agent, which is suitable for treating a skin disorder, selected from acne, rosacea, a pigmentation disorder, a cell proliferation abnormality a skin infection and a skin inflammation.
The composition contains about 10% capric/caprylic triglyceride to provide emolliency and about 10% propylene glycol and 10% dimethyl isosorbide, to provide (1) enhanced emolliency; (2) improved solubilizing capacity of the azelaic acid; and (3) enhanced skin delivery.
The compositions contain about 50% water. Therefore, they provide high skin barrier build-up effect.
The composition can be used as a cream/lotion for topical therapy of a skin diorder.
In order to create a foamable composition, the composition is filled into an aerosol canister and pressurized using a liquefied or gas propellant can be added at a concentration of about 3% to about 25%.

Part B—12 Month Stability Test

| | | | T-12 | |
|---|---|---|---|---|
| Test parameter | | T-0 | upright | inverted |
| API* assay % amount of label by HPLC (%) | | 99.3 | 100.5 | 101.7 |
| % w/w | | 14.90 | 15.07 | 15.26 |
| Product content uniformity (Intra canister) of API (%) | | 1.79 | 0.10 | 0.88 |

*API = active pharmaceutical ingredient

The total amount of active agent at T-0 and at T-12 months as a percentage of 100% of ingredient that should be present according to the label and as a percentage in the formulation w/w, respectively was determined. As can be seen, no reduction in API content was observed within the limits of detection and that the content remained uniform. The differences between samples taken from the top of the canisters and from samples taken from the bottom of the canisters were not significant and were well within the acceptable range.

Furthermore, the formulation comprising active ingredient azaleic acid—despite being a suspension and subject to graviational effect—was able to withstand sedimentation and degredation such that it has remained stable and uniformly distributed in the formulation as a suspension over a prolonged period of 12 months, whilst remaining flowable and shakable.

Example 10—Additional Dicarboxylic Acid Compositions

The following foamable vehicles were prepared and the quality of the resultant foam was ascertained.

| Formulation: | AZL018 % w/w | AZL034 % w/w | AZL035 % w/w | AZL036 % w/w | AZL037 % w/w | AZL038 % w/w | AZL039 % w/w |
|---|---|---|---|---|---|---|---|
| Azelaic Acid | 15.00 | 15.00 | 15.00 | 15.00 | 15.00 | 15.00 | 15.00 |
| Caprylic/capric triglyceride | 5.00 | 10.00 | 5.00 | 5.00 | 5.00 | 5.00 | 10.00 |
| Cetostearyl alcohol | 0.90 | 1.00 | 1.00 | 1.00 | 1.00 | 1.00 | 1.00 |
| Glyceryl stearate | 0.45 | 0.50 | 0.50 | 0.50 | 0.50 | 0.50 | 0.50 |
| Cholesterol | 1.00 | — | — | — | — | 1.00 | — |
| Benzoic acid | — | 0.20 | — | 0.20 | 0.20 | 0.20 | — |
| Benzyl alcohol | 1.00 | — | 1.00 | — | — | — | 1.00 |
| PEG-40 stearate | — | 2.60 | 2.60 | 2.60 | 2.60 | 2.60 | 2.60 |
| Methylcellulose | — | 0.10 | 0.10 | 0.10 | 0.10 | 0.10 | 0.10 |
| Hydroxypropyl methylcellulose | 0.10 | — | — | — | — | — | — |
| Xanthan gum | 0.25 | 0.10 | 0.25 | 0.10 | 0.25 | 0.10 | 0.10 |
| Polysorbate 80 | 0.90 | 0.90 | 0.90 | 0.90 | 0.90 | 0.90 | 0.90 |
| EDTA disodium dehydrate | 0.10 | — | — | — | — | — | — |
| PEG-400 | — | — | — | — | 5.00 | — | — |
| Dimethyl isosorbide | 10.00 | — | — | 5.00 | — | — | 5.00 |
| 50% phosphotidylcholine in propylene glycol | — | 2.80 | 2.80 | — | 2.80 | — | 2.80 |
| propylene glycol | 6.00 | 5.00 | 10.00 | 10.00 | — | — | — |
| Sodium hydroxide | to pH = 4.5 | to pH = 4.5 | to pH = 5.3 | to pH = 4.5 | to pH = 4.5 | to pH = 4.5 | to pH = 5.3 |
| Propellant (butane + isobutane + propane) | 8.00 | 8.00 | 8.00 | 8.00 | 8.00 | 8.00 | 8.00 |
| Purified water | to 100 | to 100 | to 100 | to 100 | to 100 | to 100 | to 100 |

Example 11—Compositions with Azalaic Acid with and without Different Polymeric Agents The following foamable vehicles were prepared and the quality of the resultant foam was ascertained.

| | DCA021 | DCA023 | DCA023A | DCA026 | DCA026a |
|---|---|---|---|---|---|
| Isopropyl myristate | | | | 11.00 | 11.00 |
| MCT oil | | 35.00 | 35.00 | | |
| Azelaic acid | 20.00 | 15.00 | 15.00 | 15.00 | 15.00 |
| Propylene glycol | 30.00 | | | | |
| Steareth 2 | | 8.00 | 8.00 | | |
| Steareth 21 | | 2.00 | 2.00 | | |
| PEG-40 Stearate | | | | 4.00 | 6.00 |
| Polysorbate 80 | 30.00 | | | 1.40 | 2.10 |
| Xanthan gum | 0.30 | | | 0.27 | |
| Methocel A4M | 0.30 | | | 0.11 | |
| Carboxy methyl cellulose | | 0.50 | | | |
| Water purified | 19.40 | 39.50 | 40.00 | 68.22 | 65.90 |
| Total | 100.00 | 100.00 | 100.00 | 100.00 | 100.00 |
| Propellant (propane, isobutene and butane mixture | 8.00 | 8.00 | 8.00 | 8.00 | 8.00 |
| Appearance: | | | | | |
| foam quality | G-E | G-E | G-E | E | E |
| color | White | White | White | White | White |
| odor | No odor | No odor | No odor | No odor | No odor |
| Microscope | Crystals | Crystals | Crystals | Crystals | Crystals |

Good to excellent foam formulations were prepared with azelaic acid, surfactant, polymeric agent, and either another oil or propylene glycol water (and without any foam adjuvant). Reducing the levels of azelaic acid to lower levels eliminated the appearance of crystals (See below).

Surprisingly, it was possible to prepare good to excellent foam after removal of the polymeric agent. Thus, the presence of a polymeric agent, is surprisingly not essential for foam quality. Nonetheless, polymeric agents may still contribute to and can be significant with respect to foam and active agent stability.

A3—in Solution

Example 12—Azalaic Acid Composition

The following foamable vehicles were prepared and the quality of the resultant foam was ascertained.

|  | DCA022 |
|---|---|
| Azelaic acid | 6.00 |
| Propylene glycol | 50.00 |
| Polysorbate 80 | 20.00 |
| Xanthan gum | 0.30 |
| Methocel A4M | 0.30 |
| Water purified | 23.40 |
| Total | 100.00 |
| Propellant ) propane, isobutene and butane mixture | 8.00 |
| Appearance: | |
| foam quality | G-E |
| Color | White |
| Odor | No odor |
| Microscope | No crystals |

Lower azaleic acid levels provide a soluble composition. No solids or precipitates are observed. No crystals were observed at the level of microscopic examination. By no crystals means the ingredients dissolve and it is not a suspension.

Example 13—Compositions with Diethyl Salicylates Azelate (TU-2100)

|  | DCA016 | DCA017 | DCA016A |
|---|---|---|---|
| PPG 15-Stearyl Ether (PPG) | 40.00 |  | 40.00 |
| Isopropyl myristate (IPM) |  | 40.00 |  |
| TU-2100 | 10.00 | 10.00 | 10.00 |
| Steareth 2 | 6.00 | 4.95 | 6.00 |
| Steareth 21 | 1.50 | 3.00 | 1.50 |
| Carboxy methyl cellulose | 0.50 | 0.50 |  |
| Water purified | 42.00 | 41.55 | 42.50 |
| Total | 100.00 | 100.00 | 100.00 |
| Propellant propane, isobutene and butane mixture | 8.00 | 8.00 | 8.00 |
| Appearance: | | | |
| foam quality | G-E | G- | G-E |
| color | White | White | White |
| odor | No odor | No odor | No odor |
| Microscope | No crystals | No crystals | No crystals |

When medium chain triglycerides were used as the emollient the formulation was poor. However, when they were substituted by PPG or IPM the foam quality increased substantially. Without being bound by any particular theory this may be because the formulations are close to phase reversal and or is due to internal tensions.

Good to excellent foam formulations were prepared with TU-2100, PPG or IPM, surfactant, polymeric agent, and water (and without any foam adjuvant). Surprisingly a good to excellent foam was produced even after removal of polymer.

Section B—Non Aqueous

B1—Example 14—PEG Based Non Aqueous Formulations with TU 2100

The following foamable vehicles were prepared and the quality of the resultant foam was ascertained.

|  | DCA014 | DCA014A | DCA014B |
|---|---|---|---|
| TU-2100 | 10.00 | 10.00 | 10.00 |
| PEG 400 | 87.50 | 85.00 | 88.00 |
| Steareth 2 | 2.00 | 5.00 |  |
| Klucel EF | 0.50 |  | 2.00 |
| Total | 100.00 | 100.00 | 100.00 |
| Propellant propane, isobutene and butane mixture | 8.00 | 8.00 | 8.00 |
| Appearance: | | | |
| foam quality | G-E | G-E | G-E |
| Color | White | White | White |
| Odor | No odor | No odor | No odor |
| Microscope | No crystals | No crystals | No crystals |

Surprisingly it was possible to make non aqueous PEG based minimal foam compositions of good to excellent quality with a) active ingredient, PEG, a single surfactant and optionally a polymeric agent and also with b) active ingredient, PEG, and a polymeric agent.

B2—Example 15—PG Based Non Aqueous Formulation with TU 2100 and with Azaleic Acid The following foamable vehicles were prepared and the quality of the resultant foam was ascertained.

|  | DCA015 | DCA020 |
|---|---|---|
| TU-2100 | 10.00 |  |
| Azelaic acid |  | 9.00 |
| PEG 400 |  |  |
| Propylene glycol | 87.50 | 88.50 |
| Steareth 2 | 2.00 | 2.00 |
| Klucel EF | 0.50 | 0.50 |
| Total | 100.00 | 100.00 |
| Propellant propane, isobutene and butane mixture | 8.00 | 8.00 |
| Appearance: | | |
| foam quality | G-E | G-E |
| color | White | White |
| odor | No odor | No odor |
| Microscope | crystals | No crystals |

Surprisingly it was possible to make non aqueous PG based minimal foam compositions of good to excellent quality with active ingredient, PG, a single surfactant and a polymeric agent. Whilst TU 2100 was not soluble in the non aqueous PG based composition, azelaic acid was soluble.

What is claimed is:

1. A method of treating acne in a mammalian subject comprising administering to an afflicted body surface of the subject a foam comprising a therapeutically effective amount of a retinoid, wherein the foam is formed from a foamable carrier and a liquified or compressed propellant, the foamable carrier comprising:
   i. a dicarboxylic acid ester;
   ii. about 0.1% to about 5% by weight of the carrier of at least one surface-active agent;
   iii. about 2% to about 50% by weight of the carrier of at least one hydrophobic solvent;
   iv. water; and
   v. a retinoid,
   wherein the foamable carrier does not comprise a polymeric gelling agent.

2. The method of claim 1, wherein the mammalian subject is a human.

3. The method of claim 2, wherein the carrier is an emulsion.

4. The method of claim 3, wherein the dicarboxylic acid ester is about 5% to about 10% by weight of the carrier.

5. The method of claim 4, wherein the dicarboxylic acid ester is diisopropyl adipate and the at least one hydrophobic solvent is mineral oil.

6. The method of claim 5, wherein the at least one surface-active agent has a hydrophilic/lipophilic balance (HLB) value of between about 9 and about 14.

* * * * *